(12) United States Patent
Gahler et al.

(10) Patent No.: US 8,597,709 B2
(45) Date of Patent: *Dec. 3, 2013

(54) DIETARY SUPPLEMENT AND METHODS OF USE

(75) Inventors: Roland Gahler, Burnaby (CA); Michael Lyon, Nanaimo (CA); Nicole Lee, Coquitlam (CA)

(73) Assignee: InovoBiologic Inc., Calgary (CA)

( * ) Notice: Subject to any disclaimer, the term of this patent is extended or adjusted under 35 U.S.C. 154(b) by 1180 days.

This patent is subject to a terminal disclaimer.

(21) Appl. No.: 11/830,615

(22) Filed: Jul. 30, 2007

(65) Prior Publication Data

US 2008/0027024 A1    Jan. 31, 2008

Related U.S. Application Data

(63) Continuation-in-part of application No. 11/400,768, filed on Apr. 7, 2006.

(60) Provisional application No. 60/670,944, filed on Apr. 12, 2005.

(51) Int. Cl.
*A23L 1/06* (2006.01)
*A23L 1/30* (2006.01)

(52) U.S. Cl.
USPC ............. 426/573; 426/96; 426/285; 426/648; 424/489

(58) Field of Classification Search
USPC ........................................................ 426/573
See application file for complete search history.

(56) References Cited

U.S. PATENT DOCUMENTS

| | | | |
|---|---|---|---|
| 3,856,945 A | | 12/1974 | Sugiyama et al. |
| 3,950,547 A | * | 4/1976 | Lamar et al. ..................... 426/74 |
| 4,350,679 A | * | 9/1982 | Mizuno et al. ................. 424/456 |
| 4,676,976 A | | 6/1987 | Toba |
| 4,707,376 A | | 11/1987 | Muraoka |
| 4,734,287 A | | 3/1988 | Singer |
| 4,882,160 A | | 11/1989 | Yang et al. |
| 4,894,250 A | | 1/1990 | Musson |

(Continued)

FOREIGN PATENT DOCUMENTS

| | | |
|---|---|---|
| CA | 2310513 A1 | 11/2001 |
| CA | 2 410 556 A1 | 12/2001 |

(Continued)

OTHER PUBLICATIONS

Alvarez-Manceñido, F., et al., "Konjac Glucomannan and Konjac Glucomannan/Xanthan Gum Mixtures as Excipients for Controlled Drug Delivery Systems. Diffusion of Small Drugs," International Journal of Pharmaceutics 349(1-2):11-18, Feb. 2008.

(Continued)

*Primary Examiner* — Elizabeth Gwartney
(74) *Attorney, Agent, or Firm* — Christensen O'Connor Johnson Kindness PLLC

(57) ABSTRACT

One aspect of the invention provides dietary fiber compositions comprising effective amounts of glucomannan, xanthan gum, and alginate to produce a desired viscosity. The invention also provides food products comprising an effective amount of a dietary fiber composition. In other aspects, the invention provides methods for preparing a dietary fiber composition or a food product comprising a dietary fiber composition and methods for promoting satiety, promoting weight loss, lowering blood glucose levels, or lowering blood cholesterol levels in a mammal.

35 Claims, 26 Drawing Sheets

*POST-MEAL PLASMA GLUCOSE RESPONSE*

(56) References Cited

U.S. PATENT DOCUMENTS

| | | | |
|---|---|---|---|
| 5,049,401 A | 9/1991 | Harada | |
| 5,633,030 A | 5/1997 | Marrs et al. | |
| 5,731,029 A * | 3/1998 | Karwowski et al. | 426/646 |
| 6,130,321 A | 10/2000 | Johnson et al. | |
| 6,210,686 B1 | 4/2001 | Bell | |
| 6,511,683 B1 | 1/2003 | Gahler et al. | |
| 6,733,769 B1 | 5/2004 | Ryan | |
| 6,774,111 B1 | 8/2004 | Wolf | |
| 7,067,498 B2 | 6/2006 | Wolf | |
| 7,326,404 B2 | 2/2008 | Vuksan | |
| 8,062,686 B2 | 11/2011 | Gahler | |
| 2002/0122865 A1* | 9/2002 | Boyer et al. | 426/590 |
| 2005/0020535 A1 | 1/2005 | Vuksan | |

FOREIGN PATENT DOCUMENTS

| | | |
|---|---|---|
| CA | 2604253 A1 | 10/2006 |
| EP | 0 290 251 A1 | 11/1988 |
| GB | 2 349 570 A | 8/2000 |
| GB | 2 349 570 A | 11/2000 |
| JP | 62014751 A | 1/1987 |
| JP | 62029947 A | 2/1987 |
| JP | 08301770 A2 | 11/1996 |
| JP | 10028554 A | 2/1998 |
| JP | 2002209554 A | 7/2002 |
| JP | 2002218945 A | 8/2002 |
| JP | 2002218945 A2 | 8/2002 |
| JP | 2007-82415 A | 4/2007 |
| KR | 2090193 A | 11/2002 |
| KR | 4040890 A | 5/2004 |
| WO | 90/07880 A1 | 7/1990 |
| WO | 95/05939 A1 | 3/1995 |
| WO | 95/06417 A1 | 3/1995 |
| WO | 95/12620 A1 | 5/1995 |
| WO | 99/38393 A2 | 8/1999 |
| WO | 00/18365 A2 | 4/2000 |
| WO | 0067799 A1 | 11/2000 |
| WO | WO 01/91586 A2 | 12/2001 |
| WO | 2005020718 A1 | 3/2005 |
| WO | 2005/092124 A1 | 10/2005 |
| WO | WO 2005/092124 A1 | 10/2005 |
| WO | 2006108283 A1 | 10/2006 |

OTHER PUBLICATIONS

Andallu, B., et al., "Effects of Mulberry (*Morus indica* L.) Therapy on Plasma and Erythrocyte Membrane Lipids in Patients With Type 2 Diabetes," Clinica Chimica Acta 314(1-2)0:47-53, Dec. 2001.

Anderson, D.M.W., et al., "Dietary Effects of Sodium Alginate in Humans," Food Additives and Contaminants 8(3):237-248, May-Jun. 1991.

Aoyama, Y., et al., "Effect on Liver and Serum Lipids in Rats of Dietary Additions of Fibers and Cholestyramine to a Cystine-Excess Diet," Agricultural and Biological Chemistry 52(11):2811-2816,1988.

Arvill, A., and L. Bodin, "Effect of Short-Term Ingestion of Konjac Glucomannan on Serum Cholesterol in Healthy Men," American Journal of Clinical Nutrition 61(3):585-589, Mar. 1995.

Birketvedt, G.S., et al., "Experiences With Three Different Fiber Supplements in Weight Reduction," Medical Science Monitor 11(1):PI5—PI8, Jan. 2005.

Blackwood, A.D., et al., "Dietary Fibre, Physicochemical Properties and Their Relationship to Health," Journal of The Royal Society for the Promotion of Health 120(4):242-247, Dec. 2000.

Blundell, J.E., and V.J. Burley, "Satiation, Satiety and the Action of Fibre on Food Intake," International Journal of Obesity 11(Suppl. 1):9-25, 1987.

Booth, A.N., et al., "Physiologic Effects of Three Microbial Polysaccharides on Rats," Toxicology and Applied Pharmacology 5:478-484, Jul. 1963.

Bosscher, D., et al., "Effect of Thickening Agents, Based on Soluble Dietary Fiber, on the Availability of Calcium, Iron, and Zinc From Infant Formulas," Nutrition 17(7/8):614-618, Jul. 2001.

Brand, J.C., et al., "Low-Glycemic Index Foods Improve Long-Term Glycemic Control in NIDDM," Diabetes Care 14(2):95-101, Feb. 1991.

Breitman, P.L., et al., "Relationship Between Meal Viscosity and Appetite Control and Food Intake in Adolescents," presented at the CDA/CSEM Canadian Diabetes Association Professional Conference and Annual Meetings, Quebec City, Canada, Oct. 27-30, 2004, 1 page.

Brown, L., et al., "Cholesterol-Lowering Effects of Dietary Fiber: A Meta-Analysis," American Journal of Clinical Nutrition 69(1):30-42, Jan. 1999.

Cameron-Smith, D., et al., "Effect of Soluble Dietary Fibre on the Viscosity of Gastrointestinal Contents and the Acute Glycaemic Response in the Rat" British Journal of Nutrition 71(4):563-571, Apr. 1994.

Chen, H.-L., et al., "Konjac Supplement Alleviated Hypercholesterolemia and Hyperglycemia in Type 2 Diabetic Subjects—A Randomized Double-Blind Trial," Journal of the American College of Nutrition 22(1):36-42, Feb. 2003.

Chiasson, J.-L., et al., "The Effect of Acarbose on Insulin Sensitivity in Subjects With Impaired Glucose Tolerance," Diabetes Care 19(11):1190-1193, Nov. 1996.

Dea, I.C.M., and E.R. Morris, "Synergistic Xanthan Gels," in P.A. Sandford and A. Laskin (eds.), "Extracellular Microbial Polysaccharides," ACS Symposium Series, vol. 45, American Chemical Society, Washington, D.C., Jun. 1977, pp. 174-182.

Doi, K., "Effect of Konjac Fibre (Glucomannan) on Glucose and Lipids," European Journal of Clinical Nutrition 49(Suppl. 3):S190-S197, Oct. 1995.

Doi, K., et al., "Treatment of Diabetes With Glucomannan (Konjac Mannan)," Lancet 1(8123):987-988, May 1979.

Eastwood, M.A., et al., "The Dietary Effects of Xanthan Gum in Man," Food Additives and Contaminants 4(1):17-26, Jan.-Mar. 1987.

Ebihara, K., et al., "Effect of Konjac Mannan, a Water-Soluble Dietary Fiber on Plasma Glucose and Insulin Responses in Young Men Undergone Glucose Tolerance Test," Nutrition Reports International 23(4):577-583, Apr. 1981.

Long, F., and S. Peng, "Effects of Refined Konjac Meal on Zinc, Iron and Calcium Absorption Rates," Yingyang Xuebao [Acta Nutrimenta Sinica] 15(1):73-78, Mar. 1993.

Ferrannini, E., and S. Camastra, "Relationship Between Impaired Glucose Tolerance, Non-Insulin-Dependent Diabetes Mellitus and Obesity," European Journal of Clinical Investigation 28(Suppl. 2):3-7, Sep. 1998.

Frost, G., et al., "Insulin Sensitivity in Women at Risk of Coronary Heart Disease and the Effect of a Low Glycemic Diet," Metabolism 47(10):1245-1251, Oct. 1998.

Howarth, N.C., et al., "Dietary Fiber and Weight Reduction," Nutrition Reviews 59(5):129-139, May 2001.

Huang, C.-Y., et al., "Effect of Konjac Food on Blood Glucose Level in Patients With Diabetes," Biomedical and Environmental Sciences 3(2):123-131, Jun. 1990.

Jenkins, A., et al., "Importance of Administration Mode of Viscous Fibre on Post-Prandial Glycemia," presented at the CDA/CSEM Canadian Diabetes Association Professional Conference and Annual Meetings, Quebec City, Canada, Oct. 27-30, 2004, 2 pages.

Jenkins, A., et al., "Improved Metabolic Control After Long Term Treatment With American Ginseng and Konjac Mannan Fiber in Type 2 Diabetes," presented at the CDA/CSEM Canadian Diabetes Association Professional Conference and Annual Meetings, Ottawa, Oct. 15-18, 2003, 1 page.

Jenkins, A., et al., "Reduction in Second Meal Glycemia With Glucomannan Viscous Fibre but Not American Ginseng in Type 2 Diabetes," presented at the CDA/CSEM Canadian Diabetes Association Professional Conference and Annual Meetings, Edmonton, Canada, Oct. 19-22, 2005, 1 page.

Jenkins, A., et al., "Reduction of HbA1c After Long Term Administration of American Ginseng and Konjac Mannan Fiber in Type 2 Diabetes," Diabetes 52(6):A386, Jun. 2003 [Abstract].

Jenkins, D.J.A., et al., "Dietary Fibres, Fibre Analogues, and Glucose Tolerance: Importance of Viscosity," British Medical Journal 1(6124):1392-1394, May 1978.

(56) References Cited

OTHER PUBLICATIONS

Jenkins, D.J.A., et al., "Guar Gum in Hyperlipidaemia," Lancet 2(7999):1351, Dec. 1976.
Jenkins, D.J.A., et al., "Implications of Altering the Rate of Carbohydrate Absorption From the Gastrointestinal Tract," Clinical and Investigative Medicine 18(4):296-302, Aug. 1995.
Jenkins, D.J.A., et al., "Viscous and Nonviscous Fibres, Nonabsorbable and Low Glycaemic Index Carbohydrates, Blood Lipids and Coronary Heart Disease," Current Opinion in Lipidology 11(1):49-56, Feb. 2000.
Keithley, J., and B. Swanson, "Glucomannan and Obesity: A Critical Review," Alternative Therapies in Health and Medicine 11(6):30-34, Nov./Dec. 2005.
Kikunaga, S., et al., "The Bioavailability of Magnesium From Wakame (Undaria pinnatifida) and Hijiki (Hijikia fusiforme) and the Effect of Alginic Acid on Magnesium Utilization of Rats," Plant Foods for Human Nutrition 53(3):265-274, 1999.
Kimura, Y., et al., "Effects of Soluble Sodium Alginate on Cholesterol Excretion and Glucose Tolerance in Rats," Journal of Ethnopharmacology 54(1):47-54, Oct. 1996.
Kodama, T., et al., "Hypocholesterolemic Mechanisms of Non-Nutritive Polysaccharides (Konjac Mannan, Pectin and Carboxymethyl Cellulose) in Foods," Journal of the Japanese Society of Food and Nutrition 25(8):603-608, 1972.
Konishi, F., et al., "Hypertrophic Effect of Unavailable Carbohydrate on Cecum and Colon in Rats," Journal of Nutritional Science and Vitaminology (Tokyo) 30(4):373-379, Aug. 1984.
Krauss, R.M., et al., "AHA Dietary Guidelines: Revision 2000: A Statement for Healthcare Professionals From the Nutrition Committee of the American Heart Association," Circulation 102(18):2284-2299, Oct. 2000.
Laifer, S., "New Findings on Fiber: Research Confirms Benefits of Fiber for Weight Loss, Lower Cholesterol, and Reduced Blood Glucose," Life Extension 11(5):34-41, May 2005.
Loening-Baucke, V., et al., "Fiber (Glucomannan) Is Beneficial in the Treatment of Childhood Constipation," Pediatrics 113(3):e259-e264, Mar. 2004.
Ludwig, D.S., et al., "Dietary Fiber, Weight Gain, and Cardiovascular Disease Risk Factors in Young Adults," JAMA 282(16):1539-1546, Oct. 1999.
Marciani, L., et al., "Effect of Meal Viscosity and Nutrients on Satiety, Intragastric Dilution, and Emptying Assessed by MRI," American Journal of Physiology. Gastrointestinal and Liver Physiology 280(6):G1227-G1233, Jun. 2001.
Marlett, J.A., et al., "Position of the American Dietetic Association: Health Implications of Dietary Fiber," Journal of the American Dietetic Association 102(7):993-1000, Jul. 2002.
Matsuda, M., and R.A. DeFronzo, "Insulin Sensitivity Indices Obtained From Oral Glucose Tolerance Testing," Diabetes Care 22(9):1462-1470, Sep. 1999.
Matsuura, Y., "Degradation of Konjac Glucomannan by Enzymes in Human Feces and Formation of Short-Chain Fatty Acids by Intestinal Anaerobic Bacteria," Journal of Nutritional Science and Vitaminology (Tokyo) 44(3):423-436, Jun. 1998.
Mayer, J., "Regulation of Energy Intake and the Body Weight: The Glucostatic Theory and the Lipostatic Hypothesis," Annals of the New York Academy of Sciences 63(1):15-43, Jul. 1955.
McCarty, M.F., "Glucomannan Minimizes the Postprandial Insulin Surge: A Potential Adjuvant for Hepatothermic Therapy," Medical Hypotheses 58(6):487-490, Jun. 2002.
Morgan, L.M., et al., "The Effect of Soluble- and Insoluble-Fibre Supplementation on Post-Prandial Glucose Tolerance, Insulin, and Gastric Inhibitory Polypeptide Secretion in Healthy Subjects," British Journal of Nutrition 64(1):103-110, Jul. 1990.
Nilson, H.W., and J.A. Wagner, "Feeding Tests With Some Algin Products," Proceedings of the Society for Experimental Biology and Medicine 76(4):630-635, Apr. 1951.

Ohta, A., et al., "The Alginate Reduce the Postprandial Glycaemic Response by Forming a Gel With Dietary Calcium in the Stomach of the Rat," International Journal for Vitamin and Nutrition Research 67(1):55-61, 1997.
Oketani, Y., et al., "Toxicity Studies on Glucomannan (1) Acute Toxicity Study in Mice and Rats," Oyo Yakuri (Applied Pharmacology) 27:127-131, 1984.
Oku, T., et al., "Mechanism of Inhibitory Effect of Unavailable Carbohydrate on Intestinal Calcium Absorption," Journal of Nutrition 112(3):410-415, Mar. 1982.
Osilesi, O., et al., "Use of Xanthan Gum in Dietary Management of Diabetes Mellitus1-3," American Journal of Clinical Nutrition 42(4):597-603, Oct. 1985.
Paradossi, G., et al., "Xanthan and Glucomannan Mixtures: Synergistic Interactions and Gelation," Biomacromolecules 3(3):498-504, May-Jun. 2002.
Pénicaud, L., "Brain Glucose Sensing Mechanism and Glucose Homeostasis," Current Opinion in Clinical Nutrition and Metabolic Care 5(5):539-543, Sep. 2002.
Pittler, M.H., and E. Ernst, "Guar Gum for Body Weight Reduction: Meta-Analysis of Randomized Trials," American Journal of Medicine 110(9):724-730, Jun. 2001.
Renard, E. et al., "Noninsulin-Dependent Diabetes and Glucose Intolerance: Effect of Glucomannan Fibers on Glycemia and Insulinemia," La Semaine des Hôpitaux de Paris 67(6):153-157, Feb. 1991.
Salmerón, J., et al., "Dietary Fiber, Glycemic Load, and Risk of NIDDM in Men," Diabetes Care 20(4):545-550, Apr. 1997.
Sandberg, A.-S., et al., "Alginate, Small Bowel Sterol Excretion, and Absorption of Nutrients in Ileostomy Subjects," American Journal of Clinical Nutrition 60(5):751-756, Nov. 1994.
Schultes, B., et al., "Modulation of Hunger by Plasma Glucose and Metformin," Journal of Clinical Endocrinology & Metabolism 88(3):1133-1141, Mar. 2003.
Seal, C.J., and J.C. Mathers, "Comparative Gastrointestinal and Plasma Cholesterol Responses of Rats Fed on Cholesterol-Free Diets Supplemented With Guar Gum and Sodium Alginate," British Journal of Nutrition 85(3):317-324, Mar. 2001.
Shatwell, K.P., et al., "Influence of the Acetyl Substituent on the Interaction of Xanthan With Plant Polysaccharides—III. Xanthan—Konjac Mannan Systems," Carbohydrate Polymers 14:131-147, 1991.
Shima, K., et al., "Effect of Dietary Fiber, Konjac Mannan and Guar Gum, on Absorbtion of Sulfonylurea in Man," Nutrition Reports International 26(2):297-302, Aug. 1982.
Stevens, J., et al., "Effect of Psyllium Gum and Wheat Bran on Spontaneous Energy Intake," American Journal of Clinical Nutrition 46(5):812-817, Nov. 1987.
Tako, M., "Binding Sites for Mannose-Specific Interaction Between Xanthan and Galactomannan, and Glucomannan," Colloids and Surfaces B: Biointerfaces 1(2):125-131, Jul. 1993.
Tako, M., "Synergistic Interaction Between Xanthan and Konjac Glucomannan in Aqueous Media," Bioscience, Biotechnology, and Biochemistry 56(8):1188-1192, Aug. 1992.
Torsdottir, I., et al., "A Small Dose of Soluble Alginate-Fiber Affects Postprandial Glycemia and Gastric Emptying in Human With Diabetes," Journal of Nutrition 121(6):795-799, Jun. 1991.
Tye, R.J., "Konjac Flour: Properties and Applications," Food Technology 45(3):82-92, Mar. 1991.
Venter, C.S., et al., "The Effects of the Dietary Fibre Component Konjac-Glucomannan on Serum Cholesterol Levels of Hypercholesterolaemic Subjects," Human Nutrition: Food Sciences and Nutrition 41F(1):55-61, 1987.
Villareal, D.T., et al., "Obesity in Older Adults: Technical Review and Position Statement of the American Society for Nutrition and NAASO, The Obesity Society," American Journal of Clinical Nutrition 82(5):923-934, Nov. 2005.
Viola, S., et al., "Effect of Pectin and Algin Upon Protein Utilization, Digestibility of Nutrients and Energy in Young Rats," Nutrition Report International 1(6):367-375, Jun. 1970.

(56) References Cited

OTHER PUBLICATIONS

Vuksan, V., et al., "3-Week Consumption of a Highly Viscous Dietary Fibre Blend Results in Improvements in Insulin Sensitivity and Reductions in Body Fat," presented at the 64th Annual Meeting of the American Diabetes Association, Orlando, Florida, Jun. 4-8, 2004, 2 pages.

Vuksan, V., et al., "Chronic Feeding of Konjac-Mannan (KJM) Fibre Improves Postprandial Glycemia in Insulin Resistance," FASEB Journal 14(4):A727, Mar. 2000 (Abstract 503.7).

Vuksan, V., et al., "Konjac-Mannan (Glucomannan) Improved Glycemia and Other Associated Risk Factors for Coronary Heart Disease in Type 2 Diabetes," Diabetes Care 22(6):913-919, 1999.

Vuksan, V., et al., "Konjac-Mannan and American Ginsing: Emerging Alternative Therapies for Type 2 Diabetes Mellitus," Journal of the American College of Nutrition 20(5):370S-380S, Oct. 2001.

Vuksan, V., et al., "Low Dose of a Highly Viscous Fiber Blend Reduces Postprandial Blood Glucose, Glycemic Index and Increases Satiety in Healthy Individuals," presented at the Natural Health Products Research Society of Canada (NHPRSC) National Research Conference, Montreal, Feb. 20-22, 2004, 1 page.

Walsh, D.E., et al., "Effect of Glucomannan on Obese Patients: A Clinical Study," International Journal of Obesity 8(4):289-293, Jan. 1984.

Williams, J.A., et al., "Inclusion of Guar Gum and Alginate Into a Crispy Bar Improves Postprandial Glycemia in Humans," Journal of Nutrition 134(4):886-889, Apr. 2004.

Wolever, T.M.S., et al., "Beneficial Effect of a Low Glycaemic Index Diet in Type 2 Diabetes," Diabetic Medicine 9(5):451-458, Jun. 1992.

Woodard, G., et al., "Xanthan Gum: Safety Evaluation by Two-Year Feeding Studies in Rats and Dogs and a Three-Generation Reproduction Study in Rats," Toxicology and Applied Pharmacology 24(1):30-36, Jan. 1973.

Wu, J. and S.-S. Peng, "Comparison of Hypolipidemic Effect of Refined Konjac Meal With Several Common Dietary Fibers and Their Mechanisms of Action," Biomedical and Environmental Sciences 10(1):27-37, Mar. 1997.

Yip, I., et al., "Liquid Meal Replacements and Glycemic Control in Obese Type 2 Diabetes Patients," Obesity Research 9(Suppl. 4):341S-347S, Nov. 2001.

Ylönen, K., et al., "Associations of Dietary Fiber With Glucose Metabolism in Nondiabetic Relatives of Subjects With Type 2 Diabetes," Diabetes Care 26(7):1979-1985, Jul. 2003.

Zhang, M.-Y., et al., "The Effect of Foods Containing Refined Konjac Meal on Human Lipid Metabolism," Biomedical and Environmental Sciences 3(1):99-105, Mar. 1990.

Ramsden, L., "Plant and Algal Gums and Mucilages," in P. Tomasik (ed.), Chemical and Functional Properties of Food Saccharides, CRC Press, Boca Raton, Florida, 2004, 5 pages.

Murray, M., "PGX™—New WellBetX™ Approach to Appetite and Blood Sugar Control," Natural Factors Nutritional Products, Dec. 3, 2003, 2-page brochure.

"SlimStyles™ PGX™," Natural Factors Nutritional Products, Jul. 30, 2004, 2-page brochure.

"Slim Styles™: The Revolutionary SlimStyles™ Diet!" Natural Factors Nutritional Products, Apr. 21, 2004, 2-page brochure.

"Superfibre May Be Answer to Battle of the Bulge," CTV.ca, Oct. 29, 2004, <http://www.ctv.ca/servlet/ArticleNews/story/CTVNews/1098979803173_94389003/?hub=Health> [retrieved Nov. 12, 2008], 2 pages.

"Dieters—Say Good-Bye to Unhealthy Diet Fads," SlimStyles with PGX, News Release, Jul. 22, 2004, <http://www.slimstyles.com/articlesJul22-04.htm> [retrieved Nov. 12, 2008], 2 pages.

"Obesity Overburdens Canada's Healthcare System," SlimStyles with PGX, News Release, Jun. 30, 2004, <http://www.slimstyles.com/articlesJun30-04.htm> [retrieved Nov. 12, 2008], 2 pages.

"Solving Syndrome X," Dr. Murray's Natural Facts, Newsletter, Feb. 11, 2004, <http://doctormurray.com/newsletter/2-11-2004.htm> [retrieved Nov. 12, 2008], 4 pages.

"Novel Fiber Limits Sugar Absorption," LE (Life Extension) Magazine, Sep. 2004, 17 pages.

Doi, K., et al., "Effect of Glucomannan (Konjac Fiber) on Glucose and Lipid Metabolism in Normal and Diabetic Subjects," in J.S. Melish et al. (eds.), "Genetic Environmental Interaction in Diabetes Mellitus: Proceedings of the Third Symposium on Diabetes Mellitus in Asia and Oceania, Honolulu, Feb. 6-7, 1981," International Congress Series No. 549, Excerpta Medica, Amsterdam, 1982, pp. 306-312.

Salmerón, J., et al., "Dietary Fiber, Glycemic Load, and Risk of Non-Insulin-Dependent Diabetes Mellitus in Women," JAMA 277(6):472-477, Feb. 1997.

Ludwig, D.S., et al., "High Glycemic Index Foods, Overeating, and Obesity," Pediatrics 103(3):e26, Mar. 1999, 6 pages.

Vicenzi, M., et al., "Effectiveness of High Viscosity Glucommanan in Biscuit Form (Dicoman Biscuits) to Induce Delayed Gastric Emptying in Obese Patients," Clinical Dietology 17:423-428, 1990 [with English translation].

Andallu, B., et al., "Effect of Mulberry (Morus indica L.) Therapy on Plasma and Erythrocyte Membrane Lipids in Patients With Type 2 Diabetes," Clinica Chimica Acta 314:47-53, 2001.

Aro, A., et al., "Improved Diabetic Control and Hypocholesterolaemic Effect Induced by Long-Term Dietary Supplementation With Guar Gum in Type 2 (Insulin-Independent) Diabetes," Diabetologia 21:29-33, 1981.

Birketvedt, G.S., et al., "Experiences With Three Different Fiber Supplements in Weight Reduction," Medical Science Monitor 11(1):p. 15-p. 18, 2005.

Jenkins, A., et al., "Effects of Different Fibres (Non-Starch Polysaccharides) on Bowel Habits in Healthy Individuals," presented at the Federation of American Societies for Experimental Biology, Washington, DC, 2006.

Jenkins, A., et al., "Importance of Administration Mode of Viscous Fiber on Postprandial Glycemia," presented at the 8th Annual Canadian Diabetes Associaton/Canadian Society of Endocrinology and Metabolism Professional Conference, Quebec City, Canada, Oct. 2004.

Jenkins, A.L., "Determination of Glycemic Index Lowering Potential of PGX® in Liquid and Solid Food Formulations," unpublished research report, Glycemic Index Laboratories, Toronto, Canada, Aug. 2, 2006, pp. 1-9.

Jenkins, A.L., et al., "Effect of American Ginseng and Konjac Mannan Fibre on Postprandial Glucose, Insulin, GIP, and GLP-1 Response in Type 2 Diabetes," presented at the Federation of American Societies for Experimental Biology, Washington, DC, 2006.

Jenkins, D.J.A., et al., "Assessment of the Longer-Term Effects of a Dietary Portfolio of Cholesterol-Lowering Foods in Hypercholesterolemia," American Journal of Clinical Nutrition 83:582-591, 2006.

Jenkins, D.J.A., et al., "Treatment of Diabetes With Guar Gum. Reduction of Urinary Glucose Loss in Diabetics," Lancet 8042:779-780, 1977.

Laiper, S., "New Findings on Fiber," Life Extension, May 2005, pp. 34-41.

Ludwig, D.S., et al., "High Glycemic Index Foods, Overeating, and Obesity," Pediatrics 103(3):1-6, 1999.

Marciani, L., et al., "Effect of Meal Viscosity and Nutrients on Satiety, Intragastric Dilution, and Emptying Assessed by MRI," American Journal of Physiology—Gastrointestinal and Liver Physiology 280:G1227-G1233, 2001.

"Novel Fiber Limits Sugar Absorption," LE Magazine (LifeExtension), Sep. 2004, pp. 1-19, <http://www.lef.org/magazine/mag2004_all.html> [retrieved Nov. 2, 2006].

Schultes, B., et al., "Modulation of Hunger by Plasma Glucose and Metformin," Journal of Clinical Endocrinology and Metabolism 88(3):1133-1141, 2003.

Villareal, D.T., et al., "Obesity in Older Adults: Technical Review and Position Statement of The American Society for Nutrition and NAASO, the Obesity Society," American Journal of Clinical Nutrition 82:923-934, 2005.

Vuksan, V., et al., "Beneficial Effects of Viscous Dietary Fiber From Konjac-Mannan in Subjects With the Insulin Resistance Syndrome," Diabetes Care 23(1):9-14, 2000.

(56) References Cited

OTHER PUBLICATIONS

Vuksan, V. et al., "Exceptionally Low Blood Glucose Response of Konjac-Mannan (Glucomannan) Fiber Blend Enriched Biscuits in Normal and Diabetic Volunteers," unpublished research paper, University of Toronto, St. Michael's Hospital, and "Dicofarm" Spa, Rome, Italy, Nov. 5, 1989, pp. 1-21.

Vuksan, V., et al., "The Effect of 2 Particle Sizes of the Viscous Fiber Blend on the Postprandial Glycemic Response Among Healthy Individuals, in Solid and Liquid Meals," unpublished research paper, University of Toronto and St. Michael's Hospital, Apr. 10, 2006, pp. 1-13.

Yip, I., et al., "Liquid Meal Replacements and Glycemic Control in Obese Type 2 Diabetes Patients," *Obesity Research 9* (Suppl. 4):341S-347S, 2001.

Ylönen, K., et al., "Associations of Dietary Fiber With Glucose Metabolism in Nondiabetic Relatives of Subjects With Type 2 Diabetes," *Diabetes Care 26*(7):1979-1985, 2003.

Notice of Allowance dated Sep. 30, 2011, from U.S. Appl. No. 11/400,768, filed Apr. 7, 2006, now U.S. Patent No. 8,062,686.

Extended European Search Report, mailed Jan. 17, 2012, issued in corresponding European Application No. EP 06 72 1805, filed Apr. 10, 2006, 11 pages.

Kiefer, D., "Novel Fiber Limits Sugar Absorption," Life Extension Magazine, Sep. 2004, pp. 25-37.

Vuksan, V., et al., "Viscosity Rather Than Quantity Determines Lipid Lowering Effects of Dietary Fiber in Individuals Consuming Typical North American Diet," FASEB Journal (Meeting Abstract Supplement) 20(5, Pt. 2):A1027, Mar. 1, 2006.

Supplementary European Search Report, mailed Jan. 17, 2012, issued in corresponding European Application No. EP 08 78 3306, filed Jul. 29, 2008, 12 pages.

Notice of Reasons for Rejection mailed Apr. 18, 2013, issued in corresponding Japanese Application No. JP 2010-518466, filed Jul. 29, 2008, 7 pages.

Extended European Search Report mailed Jan. 22, 2013, issued in corresponding European Application No. EP 12179593.4, filed Jul. 29, 2008, 6 pages.

Extended European Search Report mailed Feb. 14, 2013, issued in corresponding European Application No. EP 12179590.0, filed Jul. 29, 2008, 7 pages.

\* cited by examiner

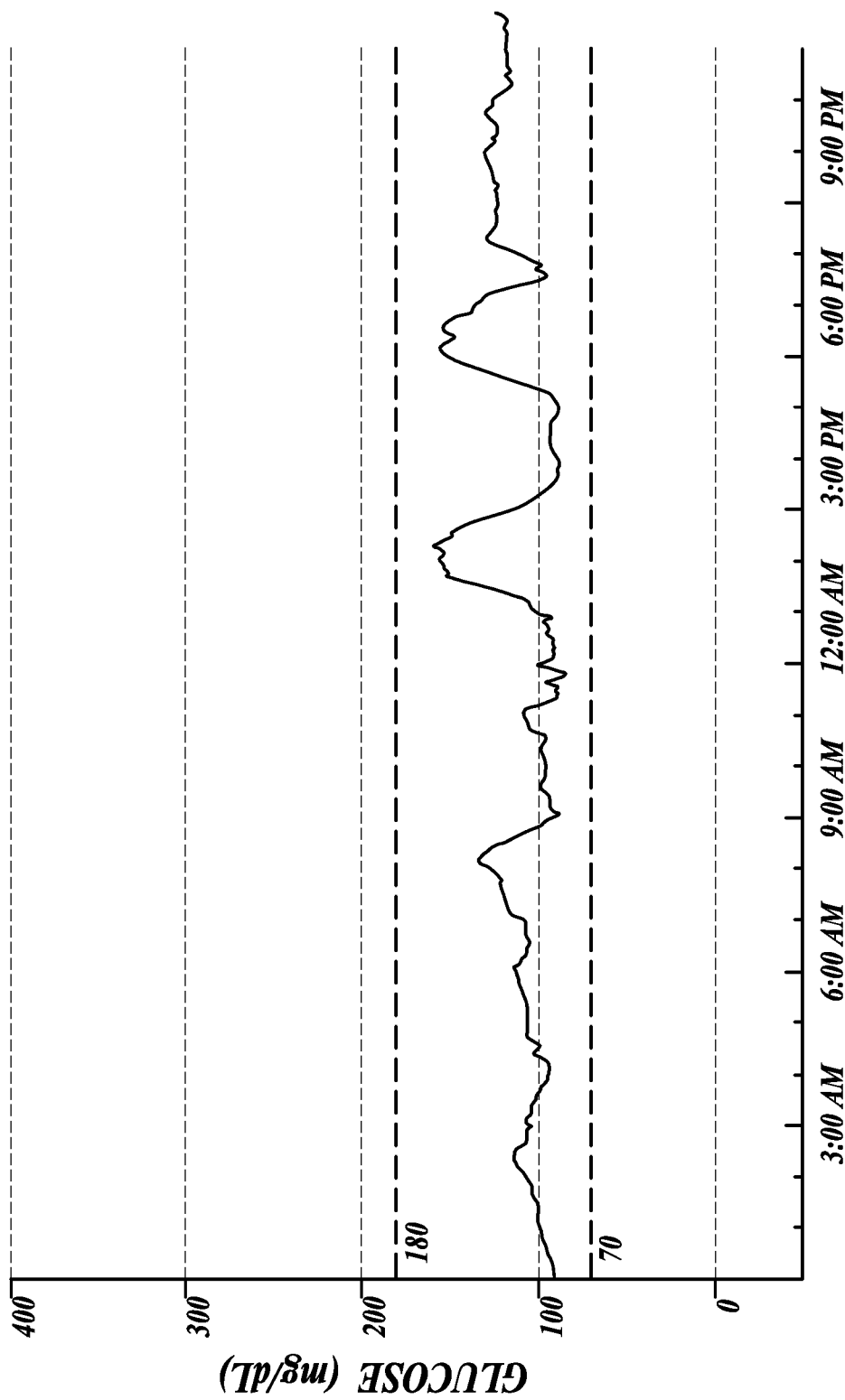

DIETARY SUPPLEMENT AND METHODS OF USE

CROSS-REFERENCES TO RELATED APPLICATIONS

This application is a continuation-in-part of U.S. application Ser. No. 11/400,768, filed Apr. 7, 2006, which claims the benefit of U.S. Provisional Application No. 60/670,944, filed Apr. 12, 2005, incorporated by reference herein.

FIELD OF THE INVENTION

The invention relates to dietary fiber compositions and their use to suppress appetite, promote weight loss, and to lower blood glucose and cholesterol levels.

BACKGROUND

Obesity and metabolic syndrome, conditions that may lead to the development of Type 2 diabetes, have become more and more common. It has been found that such conditions are due to increasing insulin resistance of the cells. Diabetic conditions are traditionally managed with insulin injections and various pharmaceuticals to regulate blood sugars. However, diet and weight loss play a major role in correcting many metabolic abnormalities associated with diabetes (Yip et al., *Obesity Res.* 9:341S-347S (2001)). Intake of foods with a high glycemic index is known to lead to overeating and obesity (Ludwig et al., *Pediatrics* 103 (3):E26 (1999)). Therefore, it is preferable that any agent used in the management of diabetic conditions as well as weight loss be low in glycemic index. It is most preferable if such agents reduce the glycemic index of foods.

A reduction in carbohydrate intake is also required in successful management of diabetic conditions. Diet counseling is helpful, but diabetics experience more food cravings as they experience more frequent states of hypoglycemia (Strachan et al., *Physiol. Behav.* 80(5):675-82 (2004)). Additionally, therapies lowering blood glucose levels in diabetic patients are often associated with the undesirable side effect of body weight gain (Schultes et al., *J. Clin. Endocrinol. Metabol.* 88(3):1133-41 (2003)). It has been reported that diets high in soluble fiber may reduce the risk of diabetes through increased insulin sensitivity (Ylonen et al., *Diabetes Care* 26:1979-85 (2003)). This may result from the possible role of dietary fiber in blood sugar regulation. It has also been reported that high viscosity meals produce a greater sense of fullness compared to low viscosity meals (Marciani et al., *Am. J. Physiol. Gastrointest. Liver Physiol.* 280:G1227-33 (2001)).

Thus, there is a need for dietary fiber compositions that assist in the management of diabetic conditions by lowering blood sugar levels and promoting satiety. The present invention addresses this need and others.

SUMMARY

One aspect of the invention provides dietary fiber compositions. Typically, the dietary fiber compositions comprise effective amounts of glucomannan, xanthan gum, and alginate to produce a desired viscosity. In some embodiments, the dietary fiber composition has a viscosity of at least 2,000 centipoise after 15 minutes under gastric conditions. In some embodiments, the dietary fiber composition has a viscosity of at least 10,000 centipoise after 15 minutes under intestinal conditions. Some embodiments of the dietary fiber composition comprise from about 48% to about 90% (w/w) glucomannan, from about 5% to about 20% (w/w) xanthan gum, and from about 5% to about 30% (w/w) alginate.

In some embodiments, the invention provides a dietary fiber composition comprising effective amounts of glucomannan, xanthan gum, and alginate to produce an initial viscosity of from about 1 to about 3,000 centipoise and at least a three-fold increase in viscosity within 15 minutes after ingestion in a mammalian subject.

In some embodiments, the invention provides food products comprising an effective amount of a dietary fiber composition comprising glucomannan, xanthan gum, and alginate. Exemplary food products include, but are not limited to, dietary supplements and meal replacements. In some embodiments, the food product comprises from about 2% to about 10% (w/w) of the dietary fiber composition and the dietary fiber composition comprises from about 48% to about 90% (w/w) glucomannan, from about 5% to about 20% (w/w) xanthan gum, and from about 5% to about 30% (w/w) alginate.

Another aspect of the invention provides a method for preparing a dietary fiber composition. In some embodiments, the methods comprise the step of combining glucomannan, xanthan gum, and alginate to provide a dietary fiber composition comprising effective amounts of glucomannan, xanthan gum, and alginate. In some embodiments, the methods further comprise the step of granulating the dietary fiber composition. The dietary fiber composition prepared according to the methods of the invention may comprise from about 48% to about 90% (w/w) glucomannan, from about 5% to about 20% (w/w) xanthan gum, and from about 5% to about 30% (w/w) alginate. In some embodiments, the methods for preparing a dietary fiber composition comprise the step of granulating the composition.

In another aspect, the present invention provides methods of reducing the initial viscosity of a dietary fiber composition comprising glucomannan, comprising the step of granulating the dietary fiber composition.

In another aspect, the invention provides methods of reducing the initial viscosity of a dietary fiber composition comprising glucomannan and xanthan, comprising the step of adding an effective amount of alginate to the composition.

A further aspect of the invention provides methods for promoting satiety, promoting weight loss, lowering blood glucose levels, or lowering blood cholesterol levels in a mammal. In some embodiments, the methods comprise the step of administering to a mammal an amount of a dietary fiber composition effective to promote satiety, to promote weight loss, to lower blood glucose levels, or to lower blood cholesterol levels in the mammal, wherein the dietary fiber composition comprises glucomannan, xanthan gum, and alginate. The dietary fiber composition administered according to these methods may comprise between about 48% and about 70% (w/w) glucomannan, between about 11% and about 13% (w/w) xanthan gum, and between about 9% and about 17% (w/w) alginate.

In another aspect, the invention provides a dietary fiber composition comprising a fiber blend comprising from about 48% to about 90% (w/w) glucomannan, from about 5% to about 20% (w/w) xanthan gum, and from about 5% to about 30% (w/w) alginate, and at least one lipid or blend thereof, wherein the lipid or blend thereof comprises at least 20% w/w of the total dietary fiber composition.

In another aspect, the invention provides a dietary fiber composition comprising (a) a fiber blend comprising glucomannan, xanthan gum, and alginate; and (b) at least one lipid or blend thereof; wherein the fiber blend and the at least one lipid are each present at an amount sufficient to allow the dietary fiber composition to exhibit a viscosity in water of from about 1 to about 3,500 centipoise after five minutes and at least a 5-fold increase in viscosity within 15 minutes after exposure to gastric conditions.

In another aspect, the present invention provides a food product comprising from 2.5 g to 7.5 g of a fiber blend per 50 g available carbohydrate of the food product, wherein the fiber blend comprises from about 48% to about 90% (w/w) glucomannan, from about 5% to about 20% (w/w) xanthan gum, and from about 5% to about 30% (w/w) alginate.

In yet another aspect, the present invention provides a method for reducing the glycemic index of a food product, the method comprising adding to the food product prior to consumption a dietary fiber blend in an amount effective to reduce the glycemic index of the food product by at least 5 glycemic index units, wherein the fiber blend comprises from about 48% to about 90% (w/w) glucomannan, from about 5% to about 20% (w/w) xanthan gum, and from about 5% to about 30% (w/w) alginate.

In another aspect, the present invention provides a method of reducing the glycemic volatility in a subject in need thereof, comprising administering to the subject in need thereof a fiber blend comprising from about 48% to about 90% (w/w) glucomannan, from about 5% to about 20% (w/w) xanthan gum, and from about 5% to about 30% (w/w) alginate. In some embodiments, this aspect of the invention includes (a) measuring a subject with a continuous glucose monitoring system for a designated time period to determine the baseline glycemic volatility of the subject; and (b) administering a effective dosage of a fiber blend to the subject, the fiber blend comprising from about 48% to about 90% (w/w) glucomannan, from about 5% to about 20% (w/w) xanthan gum, and from about 5% to about 30% (w/w) alginate for a time period effective to reduce the glycemic volatility of the subject as compared to the baseline glycemic volatility measured in step (a).

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

As shown in FIG. 13, addition of VFB to cornflakes, rice, turkey dinner, or yogurt resulted in a 26%, 45%, 24%, and 9% reduction in meal GI, respectively. The percent reductions observed in the GI for cornflakes and rice meals when adding VFB were statistically significant ($p<0.00001$), as described in EXAMPLE 13;

As shown in FIG. 14, addition of VFB reduced the glycemic index of all the granolas, with statistically significant reductions observed, irrespective of the type of granola used (p<0.0001), as described in EXAMPLE 14;

FIG. 19C shows a CGMS graph over a 24-hour period of a non-diabetic subject (ID:1146) prior to treatment with a low glycemic index diet (baseline);

DETAILED DESCRIPTION

Figure 1:
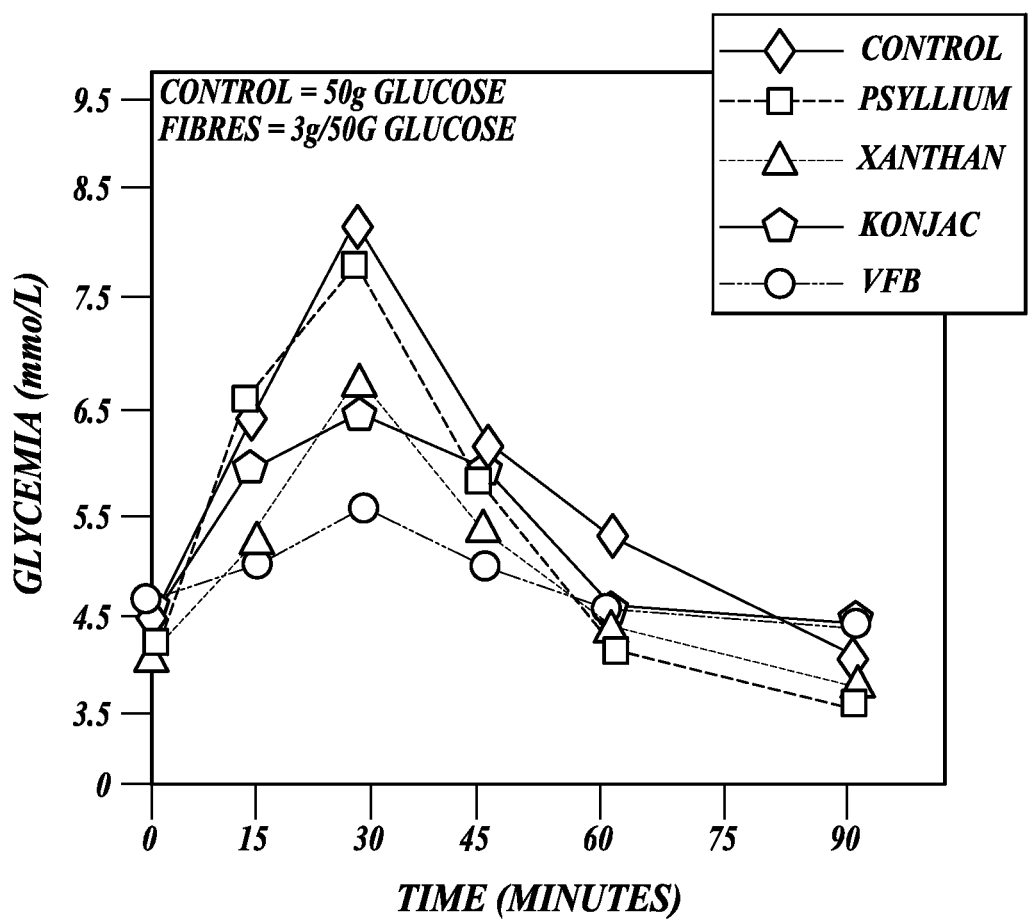
FIG. 1 illustrates the effect of different sources of soluble fibers and viscous fiber blend (VFB) on the glycemic response to a 50 g oral glucose load, as described in EXAMPLE 2.

In one aspect, the invention provides dietary fiber compositions comprising glucomannan, xanthan gum, and alginate. As used herein, "glucomannan" refers to a water-soluble dietary fiber with β-(1,4)-linked-D-mannose and β-(1,4)-linked-D-glucose residues in approximately 3:1 ratio and various α-linked galactose end groups. It is most commonly isolated from konjac root (Amorphophallus konjac) but can also be isolated from other plant sources. "Xanthan gum" refers to a heteropolysaccharide containing glucose, mannose, potassium or sodium glucuronate, acetate, and pyruvate. "Alginate" refers to a mixed polymer of mannuronic and guluronic acid.

The dietary fiber compositions of the invention comprise effective amounts of glucomannan, xanthan gum, and alginate. As used herein, an "effective amount" refers to an amount that produces the desired viscosity. Effective amounts of glucomannan, xanthan gum, and alginate are proportionate amounts of each of these components that produce the desired viscosity when combined. Effective amounts of the dietary fiber composition are amounts of the composition that produce the desired viscosity when ingested. The proportions of glucomannan, xanthan gum, and alginate in the dietary compositions are generally selected to produce a fiber blend that has an initial viscosity that is palatable, but that increases in viscosity substantially over a 15- to 60-minute time period and that maintains or increases in viscosity under gastric or intestinal conditions. As used herein, the term "initial viscosity that is palatable" refers to a range of viscosity from about 1 centipoise to about 3,000 centipoise. Liquids with a viscosity of greater than about 3,000 centipoise are difficult to ingest and are therefore considered to be non-palatable. As used herein, "initial viscosity" refers to the viscosity of the dietary composition in a 100-fold (w/w) excess of water at a temperature between about 4° C. to about 25° C., for example, between about 16° C. and about 25° C., or equivalent conditions. "Viscosity under gastric conditions" refers to the viscosity of the dietary composition in a 70-fold (w/w) excess of gastric fluid at a temperature between about 16° C. and about 25° C., or equivalent conditions. "Gastric fluid" refers to a solution having a pH of about 1.2 that is made by dissolving 2.0 g of NaCl and 3.2 g of pepsin in 7.0 mL of HCl and sufficient water to make 100 mL (see United States Pharmacopoeia). Gastric conditions may be simulated by adding 10 drops of phosphoric acid to 200 g of distilled water. "Viscosity under intestinal conditions" refers to the viscosity of the dietary composition in a 70-fold (w/w) excess of simulated intestinal fluid at a temperature between about 16° C. and about 25° C. or equivalent conditions. "Simulated intestinal fluid" refers to a solution having a pH between about 7.5 and about 8.0 that is made as follows: 6.8 g of monobasic potassium phosphate is dissolved in 250 mL of water and mixed; 190 mL of 0.2 N NaOH and 400 mL of water are added. This is followed by adding 10.0 g of pancreatin, mixing, adjusting the solution with 0.2 N NaOH to a pH of 7.5±0.1, and diluting with water to 1,000 mL (see United States Pharmacopoeia).

In some embodiments, the dietary fiber composition has an initial viscosity of between about 1 centipoise (cps) and about 3,000 cps (such as from about 200 cps to about 1,000 cps or from about 400 cps to about 1,000 cps). In some embodiments, the dietary fiber composition has a viscosity under gastric conditions of between about 600 cps and about 5000 cps (such as from about 1,000 cps to about 5,000 cps or from about 1,000 cps to about 3,000 cps) after about 30 minutes. In some embodiments, the dietary fiber composition has a viscosity under intestinal conditions of between about 1,500 cps and about 8,000 cps (such as from about 2,000 cps to about 6,000 cps or from about 2,500 cps to about 6,000 cps) after about 30 minutes. In some embodiments, the dietary fiber composition comprises effective amounts of glucomannan, xanthan gum, and alginate to produce an initial viscosity of from about 1 to about 3,000 cps and a least a three-fold increase in viscosity within 15 minutes after ingestion by a mammalian subject, as described in EXAMPLE 1.

The proportions of glucomannan, xanthan gum, and alginate in the dietary fiber compositions may be from about 48% to about 90% of glucomannan (such as from about 60% to about 80%, or from about 60% to about 90%, or from about 65% to about 75%, or from about 50% to about 80%, or from about 50% to about 70%, or about 70%), from about 5% to about 20% of xanthan gum (such as from about 10% to about 20% or from about 11% to about 13%, or from about 13% to about 17%, or about 13%, or about 17%), and from about 5% to about 30% of alginate (such as from about 10% to about 20% or from about 13% to about 17%, or about 13%, or about 17%). In some embodiments, proportions of glucomannan, xanthan gum, and alginate in the dietary compositions are about 70% glucomannan, from about 13% to about 17% xanthan, and from about 13% to about 17% alginate, as described in EXAMPLES 1 and 8.

In some embodiments, the dietary fiber compositions are granulated. As used herein, "granulation" refers to any process of size enlargement in which small particles are gathered together into larger, permanent aggregates. Granulation may be accomplished by agitation in mixing equipment, by compaction, extrusion, or globulation. The dietary fiber compositions may be granulated using various mesh sizes. The term "mesh" refers to the size of the particle as determined by its ability to pass through a screen having holes of defined dimensions. The mesh sizes used herein are Tyler equivalents, as set forth in Table 21-12 of the *Chemical Engineers Handbook* ($5^{th}$ ed., Perry & Chilton, eds.). The larger the granulation (i.e., the smaller the mesh size) of the dietary fiber composition, the longer it takes for a desired viscosity to be attained, as shown in EXAMPLE 1. In some embodiments, the dietary fiber composition is granulated using a combined mesh size by separating granulated materials by their particle size, then recombining the particle-size separated granules to give the desired viscosity profile. For example, a combined mesh size of 30 to 60 is obtained by combining granules of 30 mesh (about 600 microns), granules of about 40 mesh (about 400 microns), and granules of about 60 mesh (250 microns).

The dietary fiber compositions of the invention are prepared in a form suitable for oral use according to any method known in the art for the manufacture of oral compositions. For example, the dietary fiber compositions may be prepared as tablets, troches, lozenges, aqueous or oily suspensions, dispersible/dispensable powders or granules (e.g., powders and granules that may be sprinkled on food), emulsions, hard or soft capsules, syrups, elixirs or enteral formulas, or controlled-release compositions. For oral consumption, the dietary compositions may be added to a food or a beverage. For example, a powdered form of the dietary composition may be mixed with an ingestible liquid to form an aqueous beverage or mixed with cookie batter prior to baking. An exemplary formulation of the dietary fiber composition is as hard gelatin capsules, each capsule comprising about 500 mg of the dietary fiber composition.

The dietary fiber compositions of the invention may further comprise additional components. For example, the dietary fiber compositions may additionally comprise magnesium stearate, rice flour, xylitol, lecithin, medium chain triglycerides, flavors, stevia, and/or syloid silica. An exemplary dietary composition comprises about 48% (w/w) glucomannan, about 11% (w/w) xanthan gum, about 9% (w/w) alginate, about 31% (w/w) rice flour, and about 1% (w/w) magnesium stearate. Exemplary dietary fiber compositions are described in EXAMPLES 1, 4, and 5.

In some embodiments, the dietary fiber compositions may include mulberry extract. Mulberry leaf has been shown to possess therapeutic effects on hypoglycemia (see, e.g., *Clin. Chim. Acta* 314 (1-2):47-53). Therefore, the addition of mulberry extract may enhance the effect of the dietary fiber composition in the regulation of blood sugar levels. However, the addition of mulberry extract dilutes the concentration of the dietary fibers in the compositions and reduces the viscosity of the overall composition. Therefore, in some embodiments, the dietary fiber compositions of the invention do not include mulberry extract or contain less than 3.5% of mulberry extract.

The dietary fiber compositions of the invention may be consumed before a meal, during a meal, or after a meal. The dietary fiber compositions of the invention control hunger and induce satiety by providing high viscosity in the gastrointestinal tract. The blend of fibers maintains high viscosities under both the acidic conditions of the stomach and the alkaline conditions in the intestines. The dietary fiber compositions of the invention further assist in the management of diabetic conditions by lowering blood glucose levels.

Another aspect of the invention provides food products comprising an effective amount of a dietary fiber composition comprising glucomannan, xanthan gum, and alginate. The food products of the invention may be dietary supplements or meal replacements. In some embodiments, the food products are provided as shakes or smoothies. Typically, the food products of the invention comprise from about 2% to about 30% (such as from about 2% to about 20%, or from about 5% to about 15%, or from about 2% to about 10%) of a dietary fiber composition comprising glucomannan, xanthan gum, and alginate. Typically, the food products comprise between about 2 grams and about 15 grams of the dietary fiber per serving (such as between about 3 to 8 grams or between about 3 and about 6 grams per serving). In some embodiments, the food products of the invention comprise about 9% (w/w) of a dietary fiber composition comprising glucomannan, xanthan gum, and alginate, as described in EXAMPLES 3 and 7.

The food products of the invention may further contain additional components such as proteins or amino acids, carbohydrates, lipids, vitamins, minerals and cofactors, natural or artificial flavors, dyes or other coloring additives, and preservatives. The term "vitamins" includes, but is not limited to, thiamin, riboflavin, nicotinic acid, panthothenic acid, pyridoxine, biotin, folic acid, vitamin B12, lipoic acid, ascorbic acid, vitamin A, vitamin D, vitamin E, and vitamin K. Also included within the term "vitamins" are cofactors and coenzymes such as coenzymes include thiamine pyrophosphates (TPP), flavin mononucleotide (FMM), flavin adenine dinucleotide (FAD), nicotinamide adenine dinucleotide (NAD), nicotinamide adenine dinucleotide phosphate (NADP) Coenzyme A (CoA) pyridoxal phosphate, biocytin, tetrahydrofolic acid, coenzyme B12, lipoyllysine, 11-cis-retinal, and 1,25-dihydroxycholecalciferol. The term "vitamins" also includes choline, carnitine, and alpha, beta, and gamma carotenes. The term "minerals" refers to inorganic substances, metals, and the like, required in the human diet, including, but not limited to, calcium, iron, zinc, selenium, copper, iodine, magnesium, phosphorus, chromium, manganese, potassium, and the like, and mixtures thereof. The mineral may be in the form of a salt, an oxide, or a chelated salt.

Coloring agents include, but are not limited to, titanium dioxide and dyes suitable for food such as those known as FD&C dyes and natural coloring agents such as grape skin extract, beet red powder, beta-carotene, annatto, carmine, tumeric, chlorophyll, and paprika. The amount of coloring used may range from about 0.0% to about 3.5% dry weight of the total composition, depending on the saturation of the color.

Flavors incorporated in the composition may be chosen from synthetic flavor oils and flavoring aromatics and/or natural oils, extracts from plants, leaves, flowers, and fruits, and combinations thereof. These may include, but are not limited to, cinnamon oil, oil of wintergreen, peppermint oils, clove oil, bay oil, anise oil, eucalyptus, thyme oil, cedar leaf oil, oil of nutmeg, oil of sage, oils of citrus fruits (including, but not limited to, lemon and orange) oil of bitter almonds and cassia oil. Suitable flavors include, but are not limited to, vanilla, chocolate, mocha, coffee, ice cream, citrus (including lemon, orange, grape, lime, and grapefruit), apple, pear, peach, mango, strawberry, raspberry, cherry, plum, pineapple, and apricot. The amount of flavoring may depend on a number of factors, including the organoleptic effect desired. Flavors may be present in an amount ranging from about 0% to about 10.0% dry weight based upon the dry weight of the composition. Exemplary food products of the invention are provided in EXAMPLES 2, 3, and 7.

In some embodiments, the food products of the invention do not include bilberry extract, lutein, and/or taurine. Some embodiments of the invention provide food products containing less than 28 g of whey protein or less than 8.9 g of fructose. Some embodiments of the invention provide food products containing more than 0.9 g of medium chain triglycerides.

In a further aspect, the invention provides methods for preparing a dietary fiber composition and methods of preparing a food product comprising a dietary fiber composition. In some embodiments, the methods of preparing a dietary fiber composition comprise the step of combining effective amounts of glucomannan, xanthan gum, and alginate to produce an initial viscosity of from about 1 to about 3,000 centipoise and at least a three-fold increase in viscosity within 15 minutes after ingestion. In some embodiments, the methods of preparing a dietary fiber composition further comprise the step of granulating the dietary fiber composition.

In some embodiments, the methods of preparing a food product comprising a dietary fiber composition comprise the step of adding an effective amount of a dietary fiber composition comprising glucomannan, xanthan gum, and alginate to a food product. The food products of the invention may be consumed once or several times a day.

In another aspect, the invention provides methods of reducing the initial viscosity of a dietary fiber composition comprising glucomannan. In some embodiments, the method includes the step of granulating the dietary fiber composition comprising glucomannan to produce a composition that has a reduced viscosity. In some embodiments, the dietary fiber further comprises xanthan gum and/or alginate. In some embodiments, the method includes the step of adding an amount of alginate to the composition comprising glucomannan effective to reduce the initial viscosity of the composition, while allowing the composition to increase in viscosity over time, such as after a period of about 120 minutes.

Yet another aspect of the invention provides methods for promoting satiety, promoting weight loss, lowering blood glucose levels, or lowering blood cholesterol levels in a mammal. In some embodiments, the methods comprise administering to a mammal an amount of a dietary fiber composition effective to promote satiety in the mammal, wherein the dietary fiber composition comprises glucomannan, xanthan gum, and alginate. In some embodiments, the methods comprise administering to a mammal an amount of a dietary fiber composition effective to promote weight loss in the mammal, wherein the dietary fiber composition comprises glucomannan, xanthan gum, and alginate. In some embodiments, the methods comprise administering to a mammal an amount of a dietary fiber composition effective to lower blood glucose levels in the mammal, wherein the dietary fiber composition comprises glucomannan, xanthan gum, and alginate. In some embodiments, the methods comprise administering to a mammal an amount of a dietary fiber composition effective to lower blood cholesterol levels in the mammal, wherein the dietary fiber composition comprises glucomannan, xanthan gum, and alginate.

Exemplary dietary fiber compositions for use in the methods of the invention are as described above. The dietary fiber compositions may be administered in any form. For example, they may be administered as capsules or they may be administered in a food product.

Exemplary methods of the invention are described in EXAMPLES 2 and 3. As shown in EXAMPLES 2 and 3, the methods of the invention produce significant increases in insulin sensitivity, reduce body fat, and promote satiety and weight loss.

In another aspect, the present invention provides a dietary fiber composition comprising a fiber blend comprising from about 48% to about 90% (w/w) glucomannan, from about 5% to about 20% (w/w) xanthan gum, and from about 5% to about 30% (w/w) alginate, and at least one lipid or blend thereof, wherein the lipid or blend thereof comprises at least 20% w/w of the dietary fiber composition.

As described in EXAMPLES 9 and 10, and TABLES 28-31, the addition of a lipid or blend thereof to the various embodiments of dietary fiber compositions of the invention is effective to delay the viscous effects of the fiber blend in water, which is useful to prevent choking during oral administration in a subject, while allowing for a high viscosity within a short time under gastric conditions (in vivo conditions post-consumption).

The fiber blend comprising from about 48% to about 90% (w/w) glucomannan, from about 5% to about 20% (w/w) xanthan gum, and from about 5% to about 30% (w/w) alginate is described supra.

As used in accordance with this embodiment of the invention, a lipid is defined as a substance such as a fat, oil or wax that dissolves in alcohol but not in water. As used herein, the terms "fat" and "oil" are used interchangeably and comprise fatty acids.

In some embodiments, the lipid for use in the composition comprises a fat selected from the group consisting of a dairy fat (e.g., milk fat, butter fat), an animal fat (e.g., lard) or a vegetable fat (e.g., coconut oil, cocoa butter, or palm oil).

In some embodiments, the lipid for use in the composition comprises an edible oil or a mixture of oils. Such oils include vegetable oils (e.g., canola oil, soybean oil, palm kernel oil, olive oil, safflower oil, sunflower seed oil, flaxseed (linseed) oil, corn oil, cottonseed oil, peanut oil, walnut oil, almond oil, grape seed oil, evening primrose oil, coconut oil, borage oil and blackcurrant oil); marine oils (e.g., fish oils and fish liver oils), or a mixture thereof.

In some embodiments, the lipid for use in the composition comprises oils containing medium-chain triglycerides, such as coconut oil, palm kernel oil and butter or medium-chain triglycerides in purified form.

In some embodiments, the dietary fiber composition comprises an amount of dietary fiber mixture (VFB) in the range of from about 0.01% to about 80% of the total composition (w/w/) and an amount of lipid in the range of from 20% to about 99.99% (w/w). For example, in certain embodiments the ratio of VFB to lipid comprises, (in a weight to weight ratio) 5:95; 10:90; 20:80; 30:70; 40:60; 50:50; 60:40; 70:30; or 80:20.

In some embodiments, the dietary fiber blend for use in the dietary fiber composition comprises from about 50% to about 80% (w/w) glucomannan, from about 10% to about 20% (w/w) xanthan gum, and from about 10% to about 20% (w/w) alginate.

In some embodiments, the dietary fiber blend for use in the dietary fiber composition comprises from about 60% to about 80% (w/w) glucomannan, from about 10% to about 20% (w/w) xanthan gum, and from about 10% to about 20% (w/w) alginate.

In some embodiments, the dietary fiber blend for use in the dietary fiber composition comprises about 70% (w/w) glucomannan, from about 13% to about 17% (w/w) xanthan gum, and from about 13% to about 17% (w/w) alginate.

In one particular embodiment, the dietary fiber composition comprises a dietary fiber mixture (VFB) comprising 70% glucomannan, 13% xanthan and 17% alginate, and a medium chain triglyceride (MCT) at a ratio of 53:47 (w/w).

In some embodiments, the dietary fiber composition further comprises an outer soft gelatin capsule comprising a combination of gelatin, glycerin, and water, as described in EXAMPLE 9.

The dietary fiber composition comprising a fiber blend comprising from about 48% to about 90% (w/w) glucomannan, from about 5% to about 20% (w/w) xanthan gum, and from about 5% to about 30% (w/w) alginate, and at least one lipid or blend thereof can be manufactured by first producing the fiber blend using methods described herein, followed by the addition of the oil (or mixture thereof), and mixing the fiber blend and oil. An exemplary method of producing a dietary fiber composition is described in EXAMPLE 9.

Various embodiments of the dietary fiber blend, as described herein, may be included in food products, either liquid or solid, resulting in a reduced glycemic index of the food product. As described in EXAMPLES 11 to 14 and FIGS. 12 to 14, the benefits of the dietary fiber composition are realized in various types of foods, including without limitation, drinks mixed with the dietary fiber composition, granola, bread, rice, yogurt, cornflakes, turkey, margarine, milk. As described in EXAMPLE 13, the addition of the dietary fiber blend reduced the glycemic index of all of the test meals tested. For example, the addition of the dietary fiber blend to cornflakes, rice, turkey, or yogurt resulted in a 26%, 45%, 24%, and 9% reduction in the meal glycemic index, respectively, without reducing the palatability of the various foods tested.

In accordance with the foregoing, in another aspect, the present invention provides a food product comprising from 2.5 g to 7.5 g of a dietary fiber blend per 50 g available carbohydrate of the food product, wherein the dietary fiber blend comprises from about 48% to about 90% (w/w) glucomannan, from about 5% to about 20% (w/w) xanthan gum, and from about 5% to about 30% (w/w) alginate.

The dietary fiber blend may be combined with any type of food product, including solid, liquid, or semi-solid food products. Exemplary solid food products include, but are not limited to grains (e.g., rice, cereal (hot or cold)), granola, oatmeal, baked goods (bread, cookies, muffins, cakes and others), pasta (including noodles made with rice or other grains); meat (e.g., poultry, beef, pork, fish), dairy products (e.g., milk, yogurt, cheese, ice cream, butter, and margarine). Exemplary liquid or semi-liquid food products include, but are not limited to, meal replacement drinks, fruit juices, soups (including dry soup mixes), dietary supplements, and smoothies.

The dietary fiber blend may be added to the food product prior to consumption using any suitable method. For example, the dietary fiber blend may be baked into the food product, may be mixed with the food product, or sprinkled onto the food product.

In another aspect, the present invention provides a method of reducing the glycemic volatility in a subject in need thereof, comprising administering to the subject in need thereof a fiber blend comprising from about 48% to about 90% (w/w) glucomannan, from about 5% to about 20% (w/w) xanthan gum, and from about 5% to about 30% (w/w) alginate.

The Glycemic Volatility refers to the collective of increased frequency of blood sugar excursions, the rapid nature of the rise and fall of blood sugar and the amount of time spent above an ideal blood sugar level as increased glycemic volatility (in comparison to normal subjects with low glycemic volatility), as measured over time in a subject. The Glycemic Volatility can be measured using a commercially available continuous glucose monitoring system, such as CGMS MiniMed, Medtronic, Inc.

Figure 15:
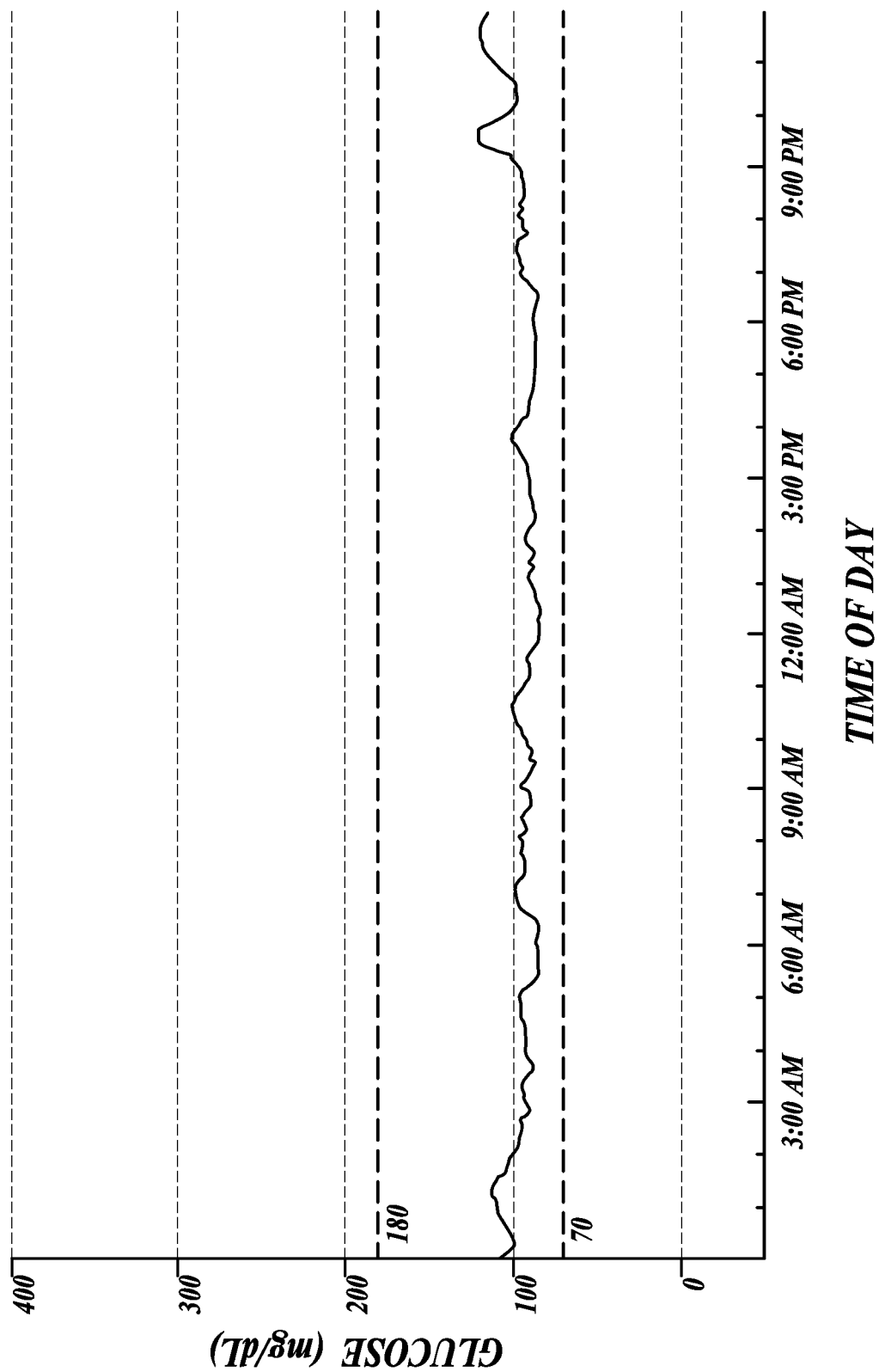
FIG. 15 shows a representative continuous glucose monitoring system (CGMS) graph measuring normal glycemic volatility in a non-obese, non-diabetic subject over a 24-hour period.
Figure 16A:
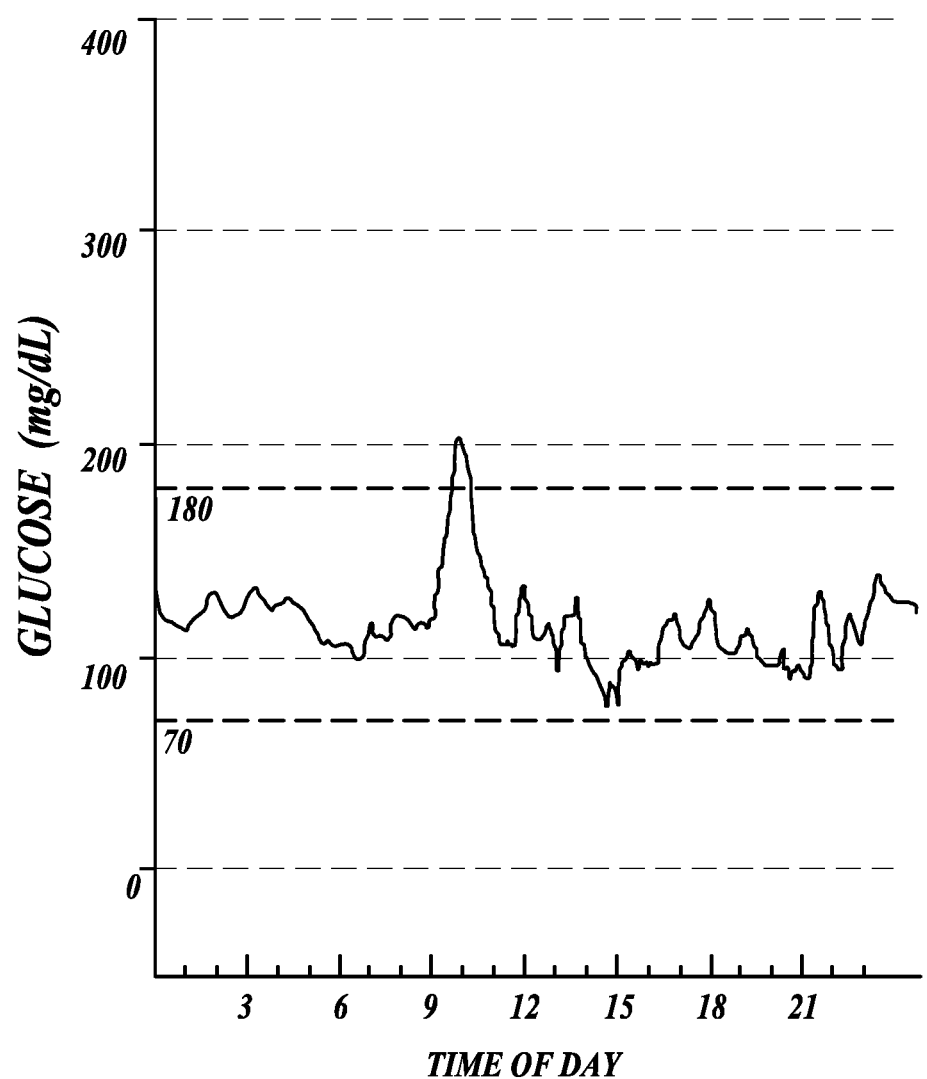
FIG. 16A shows a CGMS graph for an obese, non-diabetic subject (ID:10) measured over a 24-hour period prior to treatment with VFB (baseline)
Figure 16B:
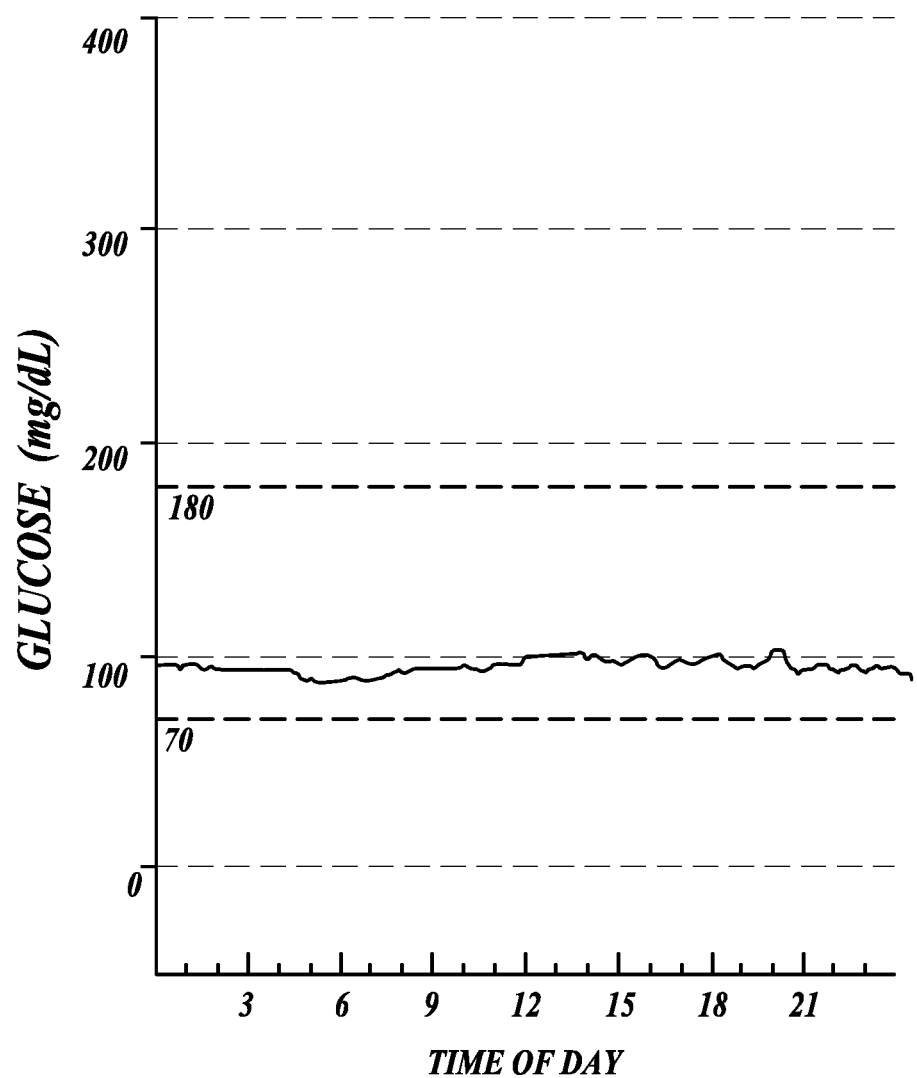
FIG. 16B shows a CGMS graph for the subject (ID:10) shown in FIG. 16A after 5 weeks of consumption of VFB (10-15 g/day)
Figure 17A:
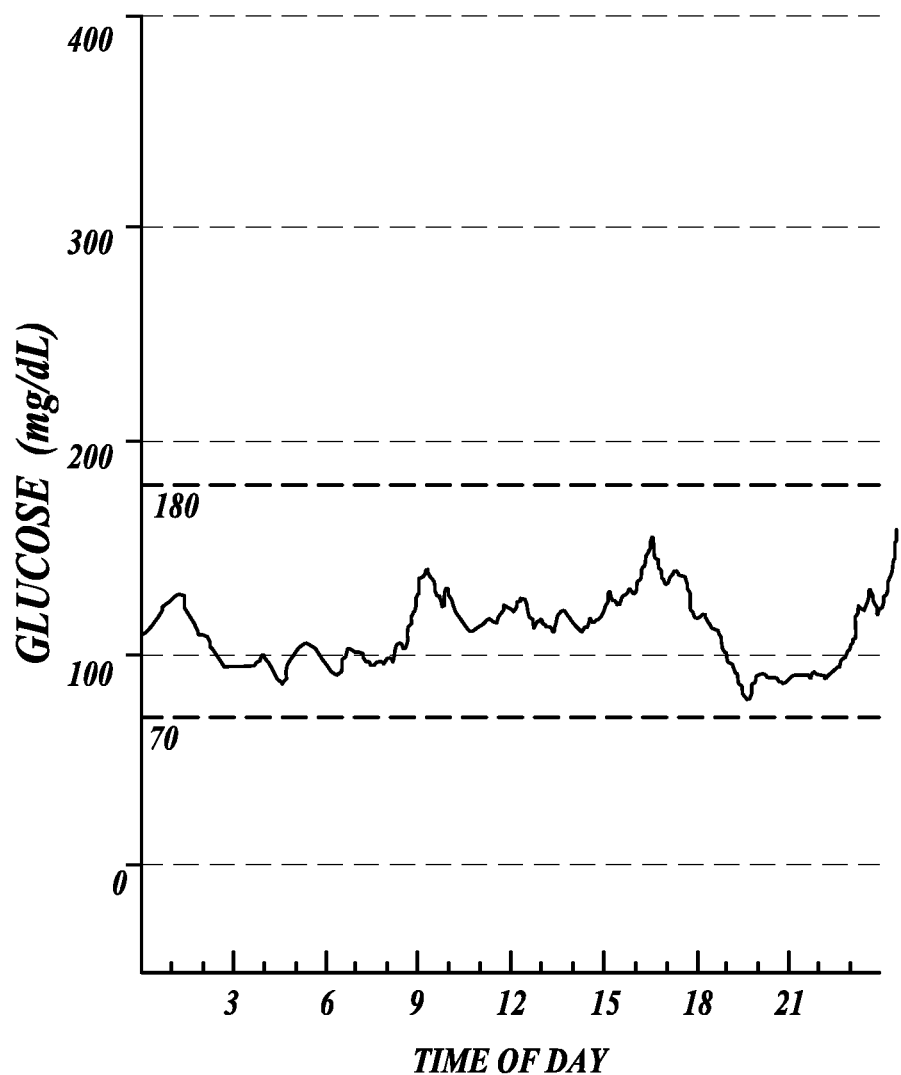
FIG. 17A shows a CGMS graph for a non-diabetic subject (ID:90) measured over a 24-hour period prior to treatment with VFB (baseline)
Figure 17B:
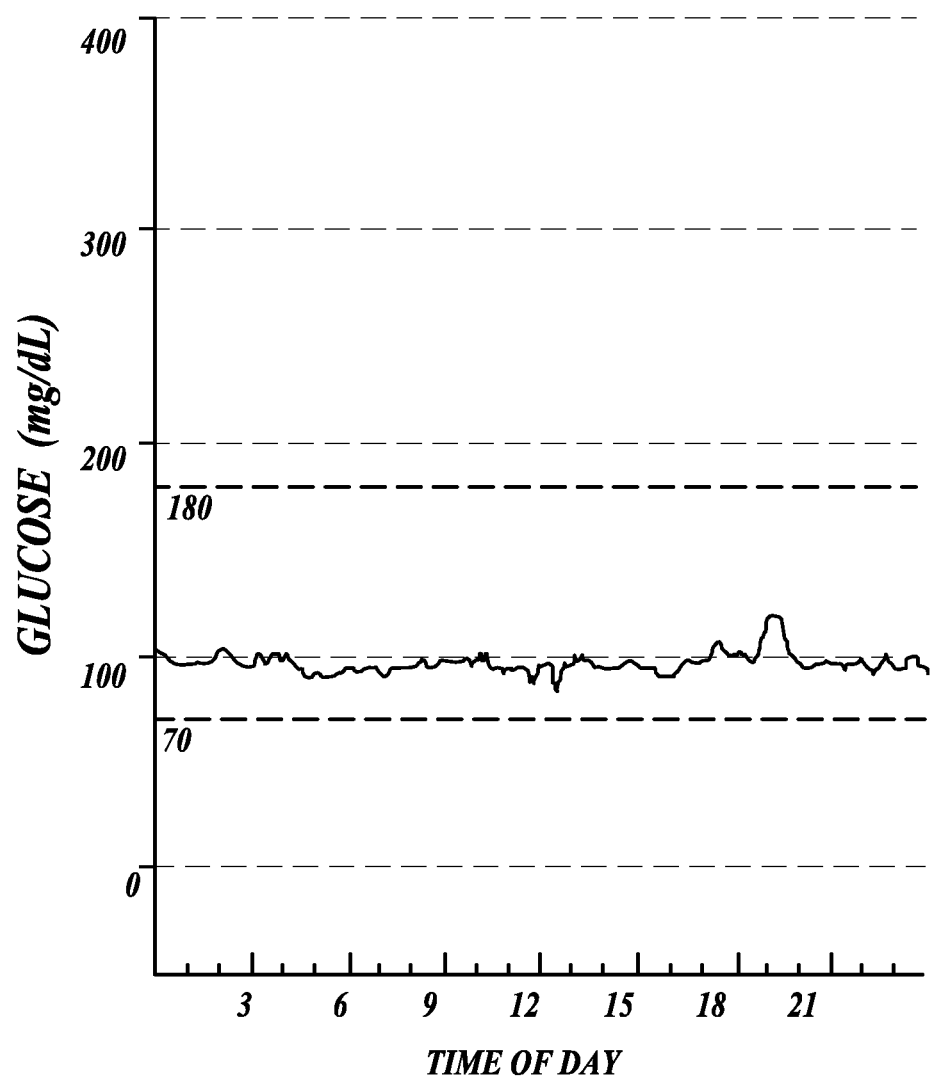
FIG. 17B shows a CGMS graph for the same subject ID:90 shown in FIG. 17A after 5 weeks of consumption of VFB (10-15 g/day)
Figure 18A:
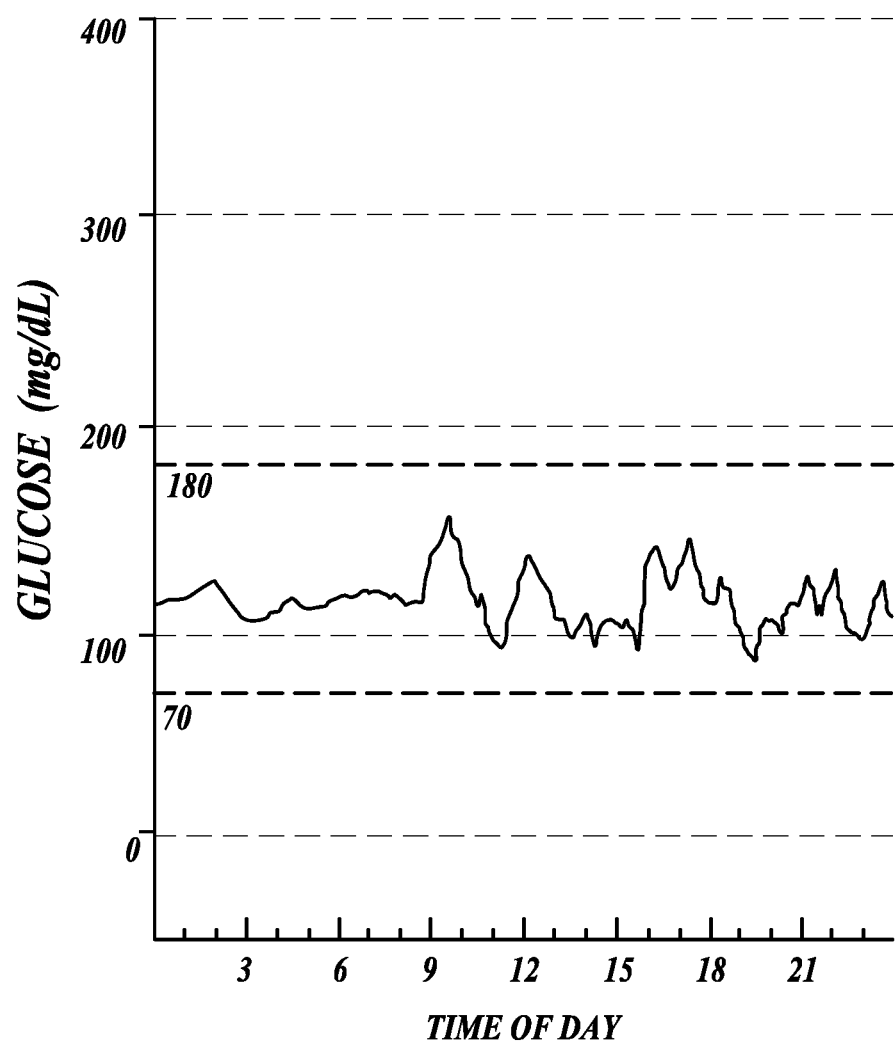
FIG. 18A shows a CGMS graph for a non-diabetic subject (ID:20) measured over a 24-hour period prior to treatment with VFB (baseline)
Figure 18B:
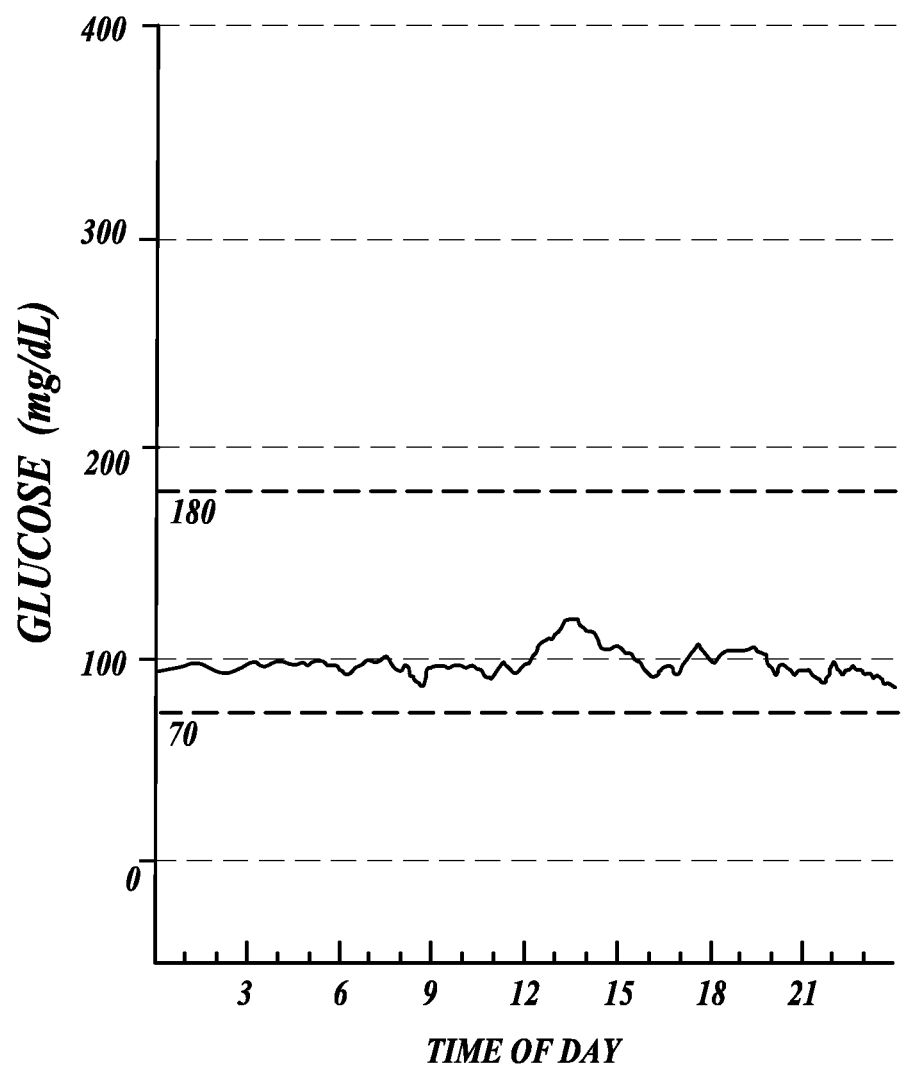
FIG. 18B shows a CGMS graph for the same subject ID:20 shown in FIG. 18A after 5 weeks of consumption of VFB (10-15 g/day)

Blood glucose levels in normal human subjects (non-obese, non-diabetic) are between 70 mmol/L to 120 mmol/L, with a low glycemic volatility (only very modest fluctuations from the average over a 24-hour period) as shown in FIG. 15. In contrast, as demonstrated in EXAMPLE 16, overweight subjects (based on a BMI from 25-30), and obese subjects (based on a BMI over 30) exhibit increased glycemic volatility (in comparison to normal subjects). As shown in FIGS. 16A, 17A, and 18A, the baseline glycemic volatility of three different obese subjects has peak blood glucose levels exceeding 120 mmol/L. As described in EXAMPLE 16 and illustrated in FIGS. 16B, 17B and 18B, the present inventors have discovered that treatment of obese subjects having increased glycemic volatility with a dietary fiber blend (VFB) comprising from about 48% to about 90% (w/w) glucomannan, from about 5% to about 20% (w/w) xanthan gum, and from about 5% to about 30% (w/w) alginate, is effective to reduce the obese subject's glycemic volatility as compared to the pre-treatment baseline glycemic volatility. For example, as shown in FIG. 16B, FIG. 17B and FIG. 18B, after treatment with 5 g to 15 g of VFB per day over at least a 4-week period (such as at least 5 weeks or at least 6 weeks), the glycemic volatility was reduced with peak glucose levels reduced to below 120 mmol/L. The VFB was surprisingly effective and found to be superior than a low glycemic index diet, as further described in EXAMPLE 16.

The glycemic volatility (GV) can be described by the following equations:

$$Gv_1 = \sum_{1\ to\ i} \left| \frac{B_i - B_{i-1}}{t_i - t_{i-1}} \right| \quad \text{(Eq. 1)}$$

$$Gv_2 = \sum_{1\ to\ i} \frac{(B_i - BL) - |B_i - BL| + |B_i - BU| + (B_i - BU)}{2t} \quad \text{(Eq. 2)}$$

Where
$B_i$ is the blood glucose level measured at any given point by the CGMS
$t_i$ is the time at which Bi is measured
t is the total time during which blood glucose level is measured by the CGMS
BL is the lowest normal blood glucose level in normal subjects, which, in most cases, is 70 mmol/L
BU is the highest normal blood glucose level in normal subjects, which, in most cases, is 120 mmol/L The $Gv_1$ equation shown above (Eq. 1) describes the slope of a CGMS graph and provides a measure of speed and frequency of the fluctuations of blood glucose in a subject over a given time period. An increased $Gv_1$ value is indicative of increased glycemic volatility in the subject. In some embodiments of the method, the $Gv_1$ can be calculated for one or more normal individuals (non-diabetic and normal weight) to obtain a $Gv_1$ reference value and the $Gv_1$ reference value can be compared to the $Gv_1$ value from a test subject, wherein a $Gv_1$ value from the test subject that is increased as compared to the reference $Gv_1$ value from the reference value is indicative of increased glycemic volatility in the test subject.

The $Gv_2$ equation shown above (Eq. 2) is a measure of the magnitude of blood glucose fluctuations outside the normal range (e.g., above 120 mmol/L and below 70 mmol/L) in a CGMS graph over a given time period. An increased $Gv_2$ value is indicative of increased glycemic volatility. In some embodiments of the method, the $Gv_2$ can be calculated for one or more normal individuals (non-diabetic and normal weight) to obtain a $Gv_2$ reference value and the $Gv_2$ reference value can be compared to the $Gv_2$ value from a test subject, wherein a $Gv_2$ value from the test subject that is increased as compared to the reference $Gv_2$ value is indicative of increased glycemic volatility in the test subject.

In some embodiments, this aspect of the invention includes (a) measuring a subject with a continuous glucose monitoring system for a designated time period to determine the baseline glycemic volatility of the subject; and (b) administering a effective dosage of a fiber blend to the subject, the fiber blend comprising from about 48% to about 90% (w/w) glucomannan, from about 5% to about 20% (w/w) xanthan gum, and from about 5% to about 30% (w/w) alginate for a time period effective to reduce the glycemic volatility of the subject as compared to the baseline glycemic volatility measured in step (a). The baseline glycemic volatility measurements may be determined using the continuous glucose monitoring system, using the GV equations (Eq. 1 and/or Eq. 2) as described above.

The continuous glucose monitoring system may be used for a designated time period sufficient to determine the glycemic volatility, such as, for example, at least 12 hours, at least 15 hours, at least 24 hours, or longer. The glycemic volatility of the subject after treatment with the fiber blend may also be determined using the continuous glucose monitoring system, using the GV equations (Eq. 1 and/or Eq. 2) as described above.

In some embodiments, the dosage of the fiber blend is from at least from 5.0 g to 15.0 g VFB per day or greater, such as from 10.0 to 15.0 g VFB per day (e.g., 5.0 g/day, 6.0 g/day, 7.0 g/day, 8.0 g/day, 9.0 g/day, 10.0 g/day, 11.0 g/day, 12.0 g/day, 13.0 g/day, 14.0 g/day or 15.0 g/day). The fiber blend may be administered as a powder stirred into a liquid, in a capsule, or sprinkled, baked or mixed into a food product, as described herein.

In accordance with the methods of this aspect of the invention, the dosage of VFB is typically administered for at least 4 weeks, such as at least 5 weeks, at least 6 weeks or longer.

In some embodiments, the dietary fiber blend comprises from about 50% to about 80% (w/w) glucomannan, from about 10% to about 20% (w/w) xanthan gum, and from about 10% to about 20% (w/w) alginate.

In some embodiments, the dietary fiber blend comprises from about 60% to about 80% (w/w) glucomannan, from about 10% to about 20% (w/w) xanthan gum, and from about 10% to about 20% (w/w) alginate.

In some embodiments, the dietary fiber blend comprises about 70% (w/w) glucomannan, from about 13% to about 17% (w/w) xanthan gum, and from about 13% to about 17% (w/w) alginate.

In some embodiments, the dietary fiber blend further comprises at least one lipid or blend thereof, wherein the lipid or blend thereof comprises at least 20% w/w of the total dietary fiber composition.

In one particular embodiment, the dietary fiber blend comprises 70% glucomannan, 13% xanthan and 17% alginate, and a medium chain triglyceride (MCT) at a ratio of 53:47 (w/w).

As used herein, the term "subject in need thereof" refers to any mammalian subject with increased glycemic volatility as compared to a normal (non-diabetic, non-obese and non-overweight) subject of the same species, including for example, overweight non-diabetic subjects (based on a BMI from 25-30), obese non-diabetic subjects (based on a BMI over 30), and type II diabetic subjects.

In some embodiments, the method of this aspect of the invention may be used to treat a non-diabetic obese subject having a baseline glycemic volatility with peak glucose levels exceeding 120 mmol/L and wherein treatment with the fiber blend reduces the glycemic volatility to a peak glucose level below 120 mmol/L, as described in EXAMPLE 16 and shown in FIGS. 16A-18B.

In some embodiments, the method of this aspect of the invention may be used to treat a diabetic obese subject having a baseline glycemic volatility with peak glucose levels exceeding 220 mmol/L and wherein treatment with the fiber blend reduces the glycemic volatility to a peak glucose level below 220 mmol/L, as described in EXAMPLE 16 and shown in FIG. 20A and FIG. 20B.

The following examples merely illustrate the best mode now contemplated for practicing the invention, but should not be construed to limit the invention Example 1

This example describes the selection of fibers in an exemplary dietary fiber composition, referred to as a viscous fiber blend (VFB), which provides desirable viscosity profiles under gastric and intestinal conditions.

In formulating VFB, the main objective was to produce a fiber blend that would increase in viscosity substantially over a 30- to 60-minute time period. To enhance palatability, it is desirable for the initial viscosity of the fiber blend to be thinner and for the maximum thickness of the fiber blend to occur in the stomach and intestines of the subject. Therefore, in selecting fibers, the blend also had to maintain or, more desirably, increase in viscosity under both gastric (acidic) and intestinal conditions. The high viscosity at this point in the digestive system would contribute to a feeling of fullness and also help with blood sugar regulation by modulating carbohydrate absorption.

TABLE 1 shows the viscosity of different fibers tested separately: galactomannan (greater than 80% pure from fenugreek, made by FenuLife), glucomannan (greater than 80% pure from Konjac root), guar gum (commercially sourced galactomannan extract of *Cyamopsis tetragonoloba*), xanthan gum (commercially sourced extracellular heteropolysaccharide from *Xanthomonas* bacteria), alginate (commercially sourced medium viscosity sodium alginate from *Ascophyllum nodosum*, and commercial fiber (consisting of 69% glucomannan, 17% xanthan, 9% carrageenan, and 8% guar, supplied by Dr. Vuksan, and described in U.S. Patent Application Publication No. 2005/0020535). Two grams of each fiber composition were blended with 200 g of water. Viscosity measurements (in centipoise) were recorded at several time intervals.

TABLE 1

Viscosity Results of Fibers Analyzed Separately

| | Viscosity (centipoise) at Different Time Points(minutes) | | | | | | | | | | |
|---|---|---|---|---|---|---|---|---|---|---|---|
| | 5 | 10 | 15 | 20 | 25 | 30 | 45 | 60 | 75 | 90 | 120 |
| Galactomannan (FenuLife) | 0 | 0 | 50 | 50 | 100 | 200 | 300 | 400 | 450 | 550 | 600 |
| Xanthan | 1400 | 1250 | 1200 | 1300 | 1250 | 1150 | 1150 | 1100 | 1100 | 1100 | 1000 |
| Guar Gum | 2950 | — | 3600 | 3750 | 3800 | 3800 | 3850 | 3850 | 4000 | 3950 | 3950 |
| Glucomannan | 4900 | — | 33,000 | 35750 | 38000 | 38750 | 40500 | 43000 | 42500 | 43250 | 44000 |
| Commercial Fiber | 550 | 800 | 1000 | 1100 | 1150 | — | 1350 | 1550 | 1550 | 1750 | 1900 |
| Alginate | 0 | 0 | 0 | 0 | 0 | 0 | 0 | 0 | 0 | 0 | 0 |

Alginate and galactomannan were the least viscous. Xanthan and guar gum reached their maximum thickness almost immediately. Glucomannan displayed a substantial increase in viscosity over time. However, it seemed excessively thick for our purposes, so we analyzed how glucomannan reacted in combination with other less viscous fibers. Viscosity results for combined fiber blends are shown in TABLE 2.

TABLE 2

Viscosity Results of Fibers Analyzed in Combination

| | Viscosity (centipoise) at Different Time Points(minutes) | | | | | | | | | | |
|---|---|---|---|---|---|---|---|---|---|---|---|
| | 5 | 10 | 15 | 20 | 25 | 30 | 45 | 60 | 75 | 90 | 120 |
| Glucomannan/Alginate (50:50) | 200 | 400 | 700 | 1100 | 1500 | 2000 | 3050 | 3800 | 4200 | 4700 | 5400 |
| Glucomannan/Xanthan (50:50) | 1150 | 1300 | 1100 | 1150 | 1150 | 1050 | 1050 | 1100 | 1100 | 1100 | 1100 |
| Glucomannan/Galactomannan (50:50) | 1050 | — | 2100 | 3900 | 4600 | 4750 | 5400 | 5600 | 5800 | 5850 | 5950 |
| Guar Gum/Alginate (50:50) | 450 | 700 | 950 | 1100 | 1250 | 1350 | 1550 | 1700 | 1750 | 1820 | 1900 |
| Glucomannan/Alginate (75:25) | 900 | 2200 | 3900 | — | 4700 | 5450 | 9500 | 14500 | 15600 | 15800 | 16300 |

Alginate, xanthan and galactomannan had a strong, thinning effect in combination with glucomannan. Xanthan's property of immediately reaching maximum viscosity carried over when combined with glucomannan. The drawback with this blend is that the initial viscosity was too thick and it did not continue to thicken over time. The alginate and glucomannan blend preserved the characteristic of glucomannan in that it continued to thicken over time. However, the initial viscosity was a bit too watery and it thickened too rapidly. The guar gum and alginate blend did not produce adequate viscosity.

From these results, it was determined that glucomannan was a desirable ingredient for the fiber blend due to its high viscosity property. It also had a very smooth texture that enhanced palatability. Alginate helped moderate the strong thickening characteristic of glucomannan and it also achieved a more palatable viscosity during the initial stages of ingestion. Xanthan, too, was selected as part of the blend since it was the only fiber that seemed to curb and thin out glucomannan near the end of the viscosity test (30-60 minutes). Guar gum and galactomannan did not exhibit any new properties that would contribute to the quality of VFB; therefore, they were not selected as part of the fiber blend.

Figure 7:
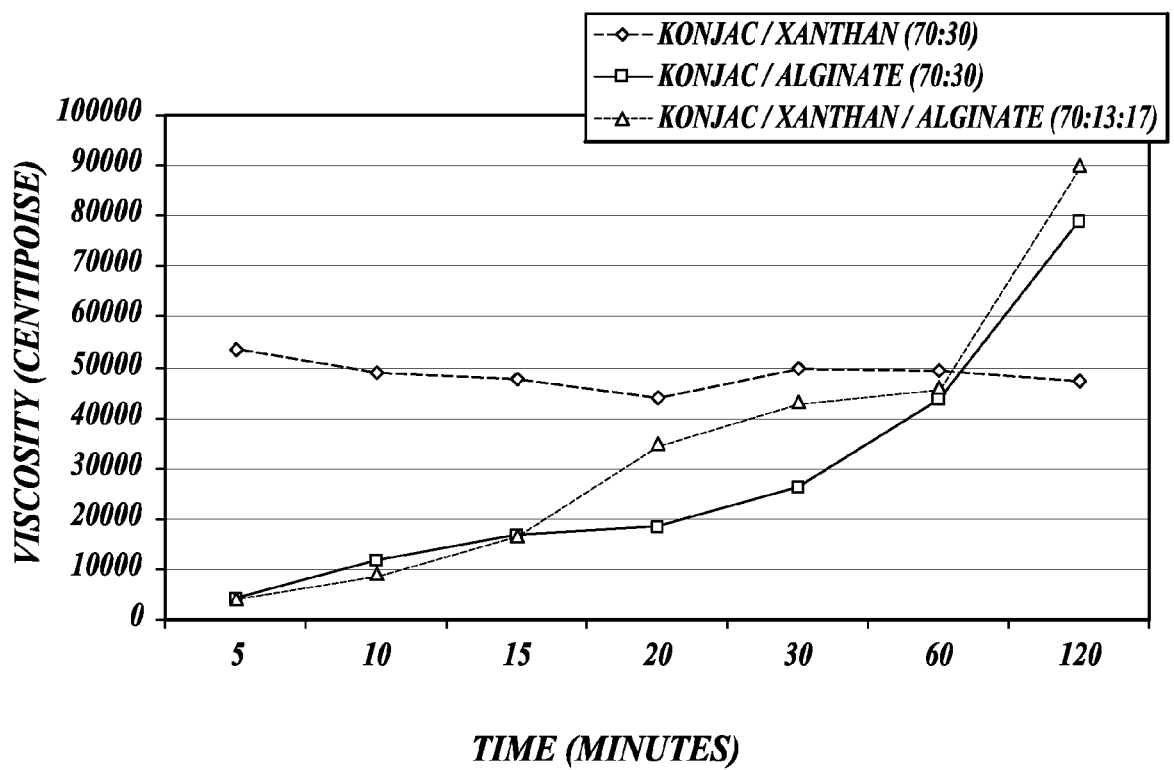
FIG. 7 graphically illustrates the viscosity profile of various fiber blends over time in distilled water, as described in EXAMPLE 8.
Figure 8:
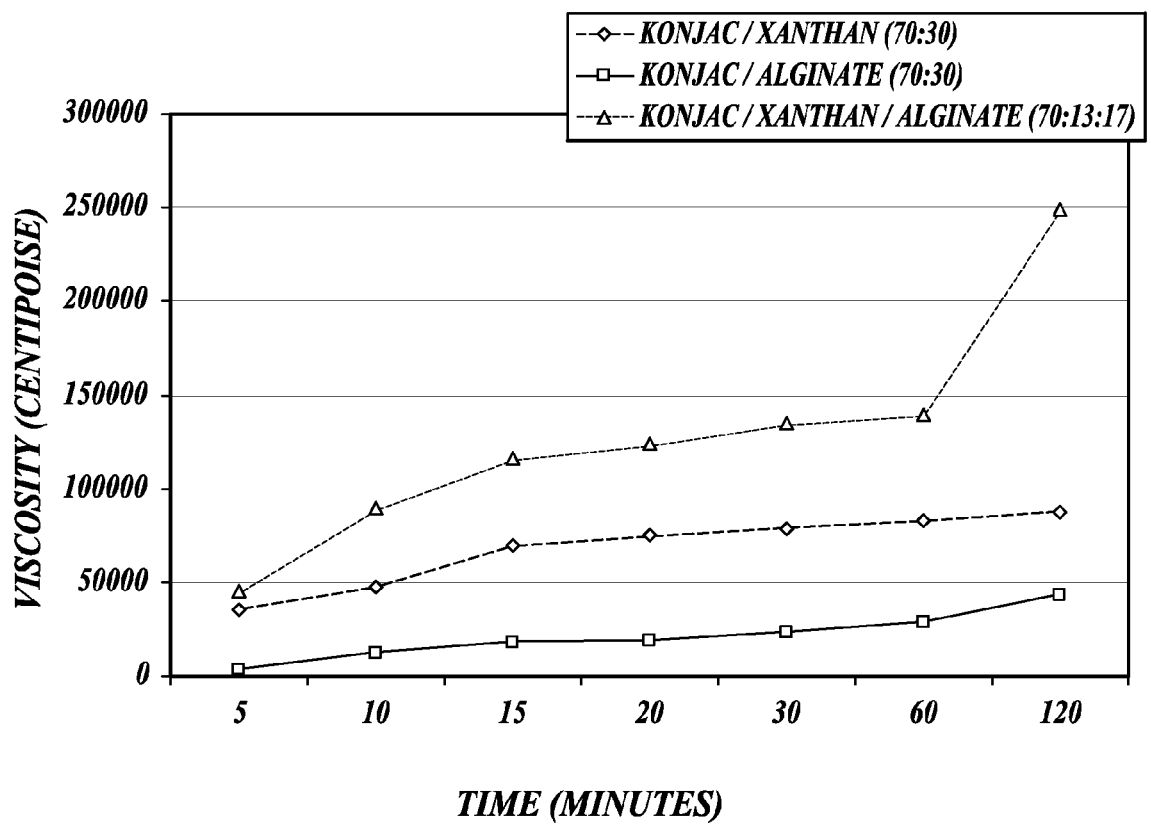
FIG. 8 graphically illustrates the viscosity profile of various fiber blends over time under gastric conditions, as described in EXAMPLE 8.

The final composition of VFB created was from 48%-90% glucomannan, from 5%-20% xanthan gum, and from 5%-30% alginate. When glucomannan, xanthan, and alginate are combined at these ratios to produce VFB, this composition exhibits unexpectedly high viscosity values after 120 minutes when blended with water, as shown in FIG. 7 and described in EXAMPLE 8. The VFB also produces unexpectedly high viscosity values after 10 minutes when blended with gastric juice, as shown in FIG. 8 and described in EXAMPLE 8.

At a lower glucomannan ratio, the product would not reach desired thickness. At a higher xanthan ratio, the product also did not reach the desired thickness. At a lower xanthan ratio, the fiber blend thickened too quickly. Alginate also had an important role in enhancing palatability by decreasing viscosity during the initial stages of the product.

In a preferred embodiment, VFB compositions were produced that contained 60%-80% glucomannan, 10%-20% xanthan gum, and 10%-20% alginate that had the desirable characteristics mentioned above. For example, a VFB composition was produced that contained 70% glucomannan, 13% xanthan gum, and 17% alginate with desirable characteristics as described herein. Another VFB composition was produced that contained 70% glucomannan, 17% xanthan gum, and 13% alginate with similar desirable properties.

The viscosity profile of VFB (70% glucomannan, 13% xanthan gum, and 17% alginate) in comparison to a competing commercial fiber is presented in TABLE 3.

TABLE 3

Viscosity Profile of VFB vs. Commercial Fiber Blend

| | Viscosity (centipoise) at Different Time Points(minutes) | | | | | | | | | |
|---|---|---|---|---|---|---|---|---|---|---|
| | 5 | 10 | 15 | 20 | 25 | 30 | 45 | 60 | 75 | 90 |
| VFB | 600 | 900 | 1,000 | 1100 | 1250 | 1300 | 1500 | 1650 | 1750 | 1850 |
| Commercial Fiber | 550 | 800 | 1,000 | 1100 | 1150 | | 1350 | 1550 | 1550 | 1750 |

The viscosity profile of VFB (70% glucomannan, 13% xanthan gum, and 17% alginate) in comparison to a competing commercial fiber in a smoothie is presented in TABLE 4. Five grams of fiber were added to a smoothie mix (see EXAMPLE 6 for composition of exemplary smoothie) and 350 g of distilled water was then added.

TABLE 4

Viscosity Profile of VFB vs. Commercial Fiber Blend in Smoothie

| | Viscosity (centipoise) at Different Time Points (minutes) | | | | | | | | |
|---|---|---|---|---|---|---|---|---|---|
| | 5 | 10 | 15 | 20 | 25 | 30 | 45 | 60 | 90 |
| VFB | 2575 | 3525 | 4100 | 4450 | 4815 | 5300 | 6000 | 6700 | 7350 |
| Commercial Fiber | 865 | 1050 | 1140 | 1290 | 1375 | 1400 | 1690 | 1725 | 2050 |

One of the differences between VFB and the commercial fiber is how they react under simulated digestive conditions. As shown in TABLES 5 and 6, VFB has the ability to increase in thickness under gastric conditions. TABLE 5 compares the viscosity profiles of VFB (70% glucomannan, 13% xanthan gum, and 17% alginate) and the commercial fiber when 2 g of fiber are added to 200 g of distilled water with 10 drops of phosphoric acid.

TABLE 5

Viscosity Comparison of VFB and Commercial Fiber Under Gastric Conditions

| | Viscosity (centipoise) at Different Time Points (minutes) | | | | | | |
|---|---|---|---|---|---|---|---|
| | 5 | 10 | 15 | 20 | 25 | 30 | 45 |
| VFB | 1000 | 2800 | 4100 | 5100 | 6150 | 6500 | 7150 |
| Commercial Fiber | 400 | 800 | | 2400 | 3500 | 4450 | 6750 |

TABLE 6 compares the viscosity profiles of VFB (70% glucomannan, 13% xanthan gum, and 17% alginate) and the commercial fiber in a smoothie product under gastric conditions. Five grams of commercial fiber or 4 g of VFB were added to a smoothie mix (see EXAMPLE 6 for composition of exemplary smoothie) and 350 g of gastric fluid was then added.

TABLE 6

Viscosity Comparison of VFB and Commercial Fiber in Smoothie Under Gastric Conditions

| | Viscosity (centipoise) at Different Time Points (minutes) | | | | | | | |
|---|---|---|---|---|---|---|---|---|
| | 5 | 10 | 15 | 20 | 25 | 30 | 45 | 60 |
| VFB | 1500 | 1850 | 2150 | 2450 | 2550 | 2600 | 2950 | 3600 |
| Commercial Fiber | 1550 | 1900 | 1950 | 2200 | 2300 | 2350 | 2700 | 3325 |

TABLE 7 compares the viscosity profile of VFB (70% glucomannan, 13% xanthan gum, and 17% alginate) compared with the commercial fiber under intestinal conditions. Two grams of fiber were added to 200 g of intestinal fluid. Intestinal fluid was made by dissolving 6.8 g of monobasic potassium phosphate in 250 mL of water, mixing, and adding 190 mL of 0.2 N NaOH and 400 mL of water. Ten grams of pancreatin was added, followed by mixing and adjusting the pH with 0.2 N NaOH to a pH of 7.5±0.1. The solution was diluted with water to 1,000 mL (United States Pharmacopoeia).

TABLE 7

Viscosity Profile Comparison of VFB and Commercial Fiber Under Intestinal Conditions

| | Viscosity (centipoise) at Different Time Points (minutes) | | | | | | | | |
|---|---|---|---|---|---|---|---|---|---|
| | 3 | 5 | 10 | 15 | 20 | 25 | 30 | 45 | 60 |
| VFB | 2600 | 6600 | 15000 | 3,5000 | 39250 | 41000 | 66500 | 69500 | 72000 |
| Commercial Fiber | 1150 | 1350 | 1700 | 2250 | 2600 | 3000 | 3000 | 5850 | 7900 |

TABLE 8 compares the viscosity profile of VFB (70% glucomannan, 13% xanthan gum, and 17% alginate) compared with the commercial fiber under intestinal conditions. Five grams of commercial fiber or 4 g of VFB were added to a smoothie mix (see EXAMPLE 6 for composition of exemplary smoothie) and 350 g of intestinal fluid was then added.

TABLE 8

Viscosity Profile Comparison of VFB and Commercial Fiber in Smoothie Under Intestinal Conditions

| | Viscosity (centipoise) at Different Time Points (minutes) | | | | | | | | |
|---|---|---|---|---|---|---|---|---|---|
| | 3 | 5 | 10 | 15 | 20 | 25 | 30 | 45 | 60 |
| VFB | 1250 | 2200 | 4200 | 5250 | | 6800 | 9000 | 15700 | 16600 |
| Commercial Fiber | 1150 | 1300 | 1450 | 1750 | 1900 | 2100 | 2250 | 2350 | 3350 |

These test results show that under simulated gastric and intestinal conditions, the VFB fiber blend thickened more than the commercial fiber blend, indicating that VFB has a higher viscosity than the commercial fibers in the stomach and may continue to thicken under intestinal conditions.

In order to create a product that is more appealing to the consumer, granulated VFB was used to further delay viscosity during the initial stages of ingestion. Granulation is achieved through addition of 30-60% (w/w) water to the VFB blend and then drying off the added water. This process is typically performed through mechanical granulators, fluid-bed granulator/dryers, mechanical agglomerators, or simple mixing followed by oven or vacuum drying.

Non-granulated VFB is quite fine and tends to clump when added with water. It absorbs moisture so quickly that the water actually encapsulates the powder. However, granulated VFB avoids this problem as the larger granules remain separated from each other when wet. Slowly the slurry thickens as the VFB granules gradually dissolve into water.

Determining the proper mesh size of VFB is important in the granulation process. Thirty mesh particles are about 600 microns in diameter, 40 mesh particles are about 400 microns in diameter, 50 mesh particles are about 300 microns in diameter, 60 mesh particles are about 250 microns in diameter, and 80 mesh particles are about 180 microns in diameter. Although it slows viscosity increase, the granulated VFB product still increases to the desirable thickness responsible for generating that full feeling and also regulating blood sugar levels by slowing down absorption of carbohydrates in the intestines. The larger the granulation (i.e., the smaller the mesh size), the more the increase in viscosity is delayed, as shown in TABLE 9.

TABLE 9

Viscosity Comparison of VFB Granulated Using Different Mesh Sizes

| | Viscosity (centipoise) at Different Time Points (minutes) | | | | | | |
|---|---|---|---|---|---|---|---|
| | 5 | 10 | 15 | 20 | 30 | 60 | 120 |
| Granulated VFB mesh size 30 (stirred) | 0 | 35 | 100 | 195 | 425 | 3760 | 45240 |
| Granulated VFB mesh size 40 (stirred) | 55 | 220 | 490 | 2095 | 6545 | 28780 | >90000 |
| Granulated VFB mesh size 60 (stirred) | 590 | 4295 | 12090 | 28755 | 53035 | 82630 | >90000 |
| Non-granulated VFB (blended) | 612.5 | 1126 | 2356 | 3367.5 | 7880 | 19400 | 48860 |
| Non-granulated VFB (stirred) | 190 | 620 | 5073 | 7150 | 15380 | 56990 | >90000 |
| Granulated VFB combined mesh size 30-60 | 95 | 315 | 1115 | 4330 | 11215 | 48800 | >90000 |

A combination of 30- to 60-mesh size granulated VFB product consisting of a 1:1:1 combination of 30-, 40-, and 60-mesh size granules is desirable. A larger proportion of the smaller mesh will delay the increase in viscosity even more.

Example 2

This example describes that consumption of an exemplary dietary fiber composition (VFB) of the invention results in improvements in insulin sensitivity and reductions in body fat.

A 5%-10% loss in body fat can decrease the risk factors associated with the metabolic syndrome (Krauss et al., *Circulation* I(18):2284-99 (2000)). Common weight loss strategies such as pharmacological treatments, hypocaloric diets, and fad diets do not target appetite, are difficult and costly to maintain, do not address many of the metabolic abnormalities associated with obesity and Type 2 diabetes, and result in weight regain and reestablishment of comorbidities once they are discontinued.

Prospective studies demonstrate that high dietary fiber is strongly and inversely related to body weight, satiety, and energy intake (Stevens et al., *Am. J. Clin. Nutr.* 46(5):812-7 (1987); Blundell & Burley, *Int. J. Obes.* 11 (Suppl. 1):9-25 (1987); Howarth et al., *Nutr. Rev.* 59(5):129-39 (2001)). Evidence also suggests that high soluble fiber intake is associated with improvements in insulin sensitivity and glycemia (Salmeron et al., *Diabetes Care* 20(4):545-50 (1997); Salmeron et al., *JAMA* 277(6):462-77 (1997); Jenkins et al., *Lancet* 2(7999):1251 (1967); Doi et al., *Lancet* 1(8123):987-8 (1979); Shima et al., *Nutr. Rep. Int.* 26:297-302 (1982)). Consumption of purified, highly viscous fibers (Brand et al., *Diabetes Care* 14(2):95-101 (1991); Wolever et al., *Diabet. Med.* 9(5):451-8 (1992)) such as guar gum (Jenkins et al., *Lancet* 2(8042):779-80 (1977); Aro et al., *Diabetologia* 21(1):29-33 (1981)) and glucomannan (Vuksan et al., *Diabetes Care* 23(1):9-14 (2000)) has resulted in improved insulin sensitivity in subjects with insulin resistance, Type 2 diabetes, and the metabolic syndrome (Chiasson et al., *Diabetes Care* 19(11):1190-3 (1996); Frost et al. *Metabolism* 47(10): 1245-51 (1998)).

It is thought that viscous fiber slows digestion and absorption and affects acute and long-term glycemic control and, thus, leads to appetite control (Meyer, *Ann. NY Acad. Sci.* 63:15-32 (1955); Penicaud et al., *Curr. Opin. Clin. Nutr. Metab. Care* 5(5):539-43 (2002)) and increased insulin sensitivity. Insulin is known to help regulate fat metabolism and also plays a key role in diabetes. Lowering insulin levels also makes people feel less hungry and this could also explain its link to weight loss.

The present study tested the hypothesis that a metabolically controlled low-fat diet that is supplemented with a blend of highly viscous dietary fibers would improve postprandial glycemic control and insulin secretion as a result of a decrease in body weight and percent body fat. According to the hypothesis, the highly viscous dietary fibers provide mechanical effects (for example, by affecting gastric distension, gastric emptying, gastrointestinal transit time, nutrient absorption rate, and nutrient contact with gastro-intestinal tract), as well as metabolic effects (for example, by affecting hormone secretion, glycemic and insulin responses, short-chain fatty acids, and fecal energy excretion).

Methods

1. Subjects

There were 11 participants in the study. The inclusion criteria are shown in TABLE 10, the baseline profile of the participants is shown in TABLE 11.

TABLE 10

Inclusion Criteria

| Risk Factor | Inclusion Criteria |
|---|---|
| Hypertension | Blood Pressure: 135/95 mm Hg = 145 |
| Hyperinsulinemia | Fasting Plasma Insulin: >53 pmol/L |
| Impaired Glucose Tolerance | 2 Hour Post Challenge (Blood) Glucose: 7.8-11.0 mmol/L |
| Overweight | Body Mass Index: <30 kg/m² |
| Dyslipidemia | High Density Lipoprotein: Men <0.9 mml/l, women <1.2 mm/l |
| | Triglycerides: 2.3-4.5 mmol/l |
| Other | Absence of coronary heart disease, visceral obesity, not taking medications for hyperglycemia, hyperlipidemia or hypertension, less than 2 alcoholic drinks/day, non-smokers |

TABLE 11

Participant Profile

| Parameter | Baseline Profile |
|---|---|
| Fasting Plasma Insulin | 98 ± 13 pmol/l |
| 2-Hour Postprandial Plasma Insulin | 439 ± 68 pmol/l |
| Serum Cholesterol | 5.2-6.7 mmol/l |
| Exercise | Sedentary |

TABLE 11-continued

Participant Profile

| Parameter | Baseline Profile |
|---|---|
| Mean Age | 55 ± 4 years (range: 46-61) |
| Body Mass Index | 28 ± 1.5 kg/m² |
| Waist to Hip Ratio | Men: 0.98 + 0.2 (waist: 96 ± 12 cm) |
| | Women: 0.91 ± 0.4 (waist: 87 ± 19 cm) |

2. Design

Randomized, double-blind, placebo-control, crossover design. During the 6-week run-in period, participants consumed the National Cholesterol Education Program Therapeutic Lifestyle Changes (TLC) diet. The experimental phase of the study consisted of two successive 3-week treatment periods, separated by a 2-week washout period (with the TLC diet). During the first treatment period, subjects were randomly assigned to either a TLC diet with the viscous fiber blend (VFB) or wheat bran (WB) alone control. For the second treatment period, participants were crossed over. At week 0 and week 3, participants came to the clinic and consumed a test or control breakfast, and postprandial glucose and insulin were assessed along with body weight and % body fat. At the beginning and end of each experimental period, participants were tested for glucose and insulin concentrations at 0, 30, 45, 60, 90, 120, and 180 minutes after a test or control breakfast. Insulin sensitivity was calculated as previously described (Matsuda & DeFronzo, *Diabetes Care* 22:1462-70 (1999)). Body fat was determined by infra-red interactance (Futrex-5000) at week 0 and week 3.

3. Test Breakfasts

In a crossover design, participants with reduced insulin sensitivity and the metabolic syndrome were assigned to consume a metabolically controlled diet enriched with either 0.5 g/100 kcal of highly viscous dietary fiber (VFB, test breakfast) or matched wheat bran control (control breakfast) over two 3-week periods, separated by a 2-week washout period. The control breakfast consisted of 49 g of wheat bran cookies, 52 g of bran flakes, 250 mL of 2% milk, and 8 g of butter. The test breakfast consisted of 58 g VFB cookies (containing approximately 10% VFB fibers, 25% sucrose, with a nutrient profile of about 6% protein, 14% fat, 60% available carbohydrates, 1.5% ash, and 2.8% moisture), 69 g bran flakes, 250 mL 2% milk, and 8 g of butter. The two breakfasts were isocaloric and identical in appearance and taste. The nutrient profile of the two breakfasts differed only in the type of fiber, as shown in TABLE 12.

TABLE 12

Nutrient Profile of Control and Test Breakfast

| | Control Breakfast | Test Breakfast |
|---|---|---|
| Energy | 673 Kcal | 678 Kcal |
| Protein | 10.3% | 11.2% |
| Total Fat | 29.0% | 28.6% |
| Available Carbohydrate | 61.1% | 59.2% |
| Total Fiber | 12.0 g | 11.4 g |
| Soluble Fiber | 1.2 g | 5.4 g |

Results

1. Rheology

Table 13 shows the viscosity of five different viscous soluble fiber sources compared to viscous fiber blend (VFB). Measurements of the samples were taken by a Brookfield viscometer (Middleboro, Mass.) on a 1% solution at 24-hours using an "F" spindle at a shear rate of 30 rotations per second. Data are the mean of three or more repetitions (cps=centipoises).

TABLE 13

Viscosity Comparison of Different Soluble Fiber Sources

| Soluble Fiber Source | Viscosity (centipoise) |
|---|---|
| Kappa C. | 2000 |
| Phyllium | 6000 |
| Xanthan | 12000 |
| Guar | 17000 |
| Konjac 98% | 41000 |
| VFB | 112000 |

2. Glycemic Response

FIG. 1 and TABLE 14 show the effects of administering 3 g of various sources of soluble fibers and VFB administered on the glycemic response to a 50 g oral glucose load. The control is a 50 g oral glucose load alone.

TABLE 14

Effects of Different Soluble Fiber Sources on Area Under the Curve Glucose Response

| Soluble Fiber Source | Under the Curve Glucose Response (mmol/L) |
|---|---|
| Control | 113 |
| Phyllium | 100 |
| Xanthan | 81 |
| Konjac 98% | 80 |
| VFB | 39 |

3. Appetite Control

Figure 2A:
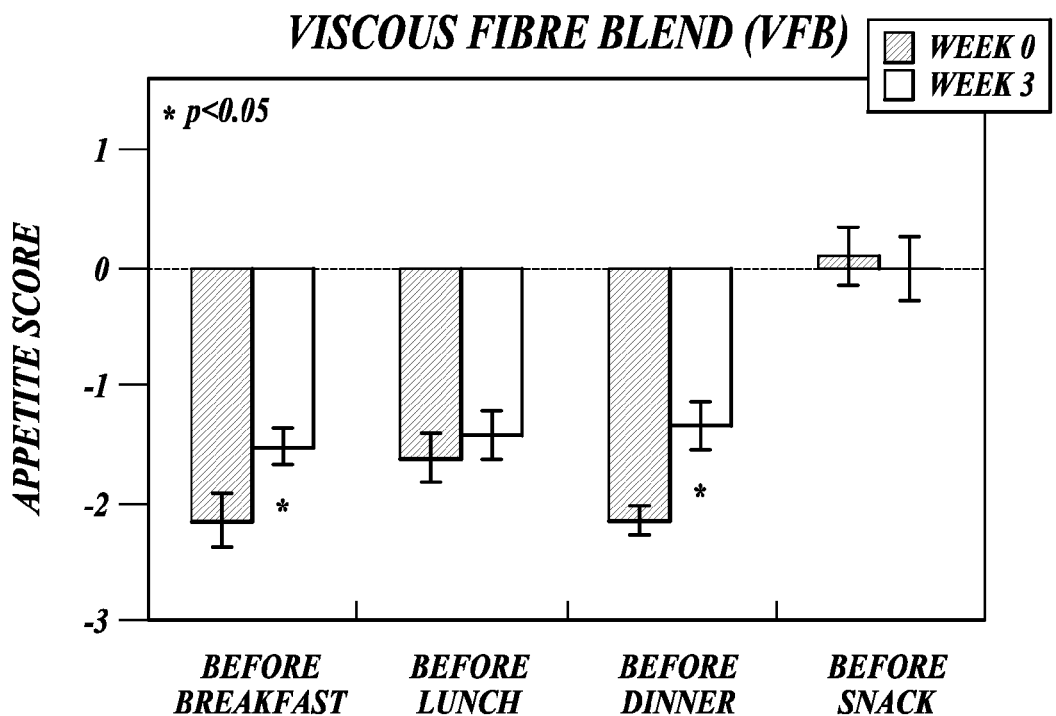
FIG. 2A provides a comparison of subjective appetite ratings before each meal and bedtime snack at week 0 and week 3 in subjects provided with test breakfasts containing VFB cookies, as described in EXAMPLE 2. Data are expressed as Means±SD. Significant differences at $p<0.05$ are indicated by an asterisk.
Figure 2B:
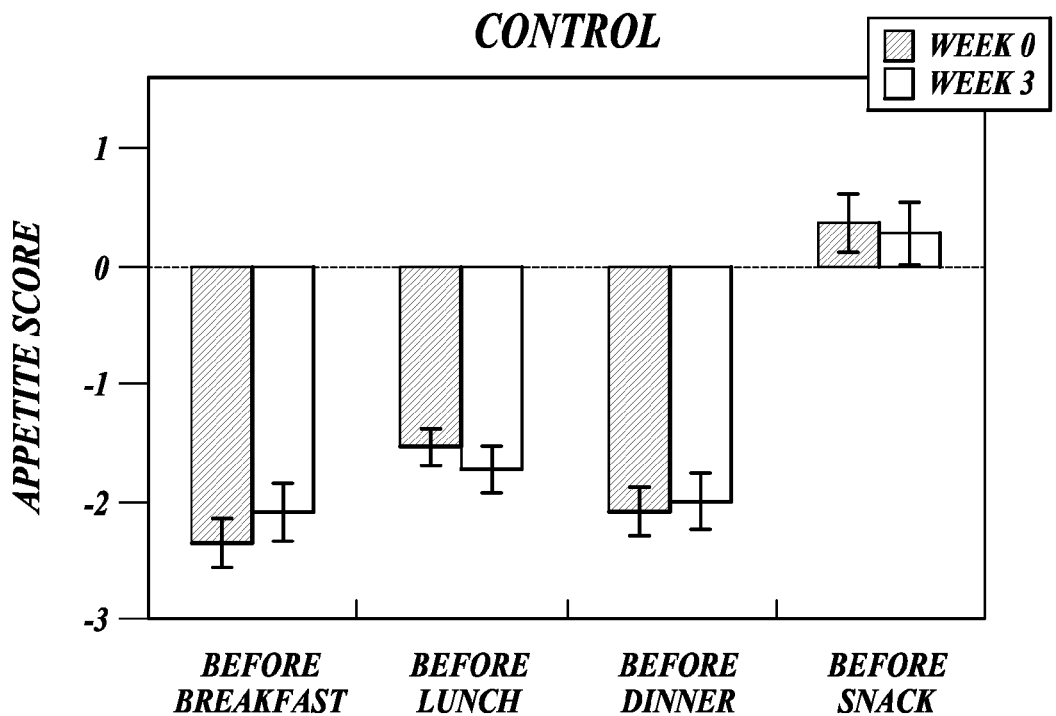
FIG. 2B provides a comparison of subjective appetite ratings before each meal and bedtime snack at week 0 and week 3 in subjects provided with control breakfasts, as described in EXAMPLE 2. Data are expressed as Means±SD. Significant differences at $p<0.05$ are indicated by an asterisk.

FIGS. 2A-B and Table 15 show a comparison of subjective appetite ratings before each meal and bedtime snack at week 0 and week 3 in subjects provided with test breakfasts with VFB (FIG. 2A) and control breakfasts (FIG. 2B). Data are expressed as Means±SD. Significant differences at $p<0.05$ are indicated by an asterisk.

TABLE 15

Comparison of Appetite Ratings in Subjects Provided With Test Breakfasts and Control Breakfasts

| | Appetite Score | | | | | | | |
|---|---|---|---|---|---|---|---|---|
| | Before Breakfast | | Before Lunch | | Before Dinner | | Before Snack | |
| | Week 0 | Week 3 | Week 0 | Week 3 | Week 0 | Week 3 | Week 0 | Week 3 |
| | VFB Treatment | | | | | | | |
| MEAN | −2.18 | −1.55 | −1.64 | −1.45 | −2.18 | −1.36 | 0.09 | 0.00 |
| SEM | 0.23 | 0.16 | 0.20 | 0.21 | 0.12 | 0.20 | 0.25 | 0.27 |
| | Control | | | | | | | |
| MEAN | −2.36 | −2.09 | −1.55 | −1.73 | −2.09 | −2.00 | 0.36 | 0.27 |
| SEM | 0.20 | 0.25 | 0.16 | 0.19 | 0.21 | 0.23 | 0.24 | 0.27 |

4, Glucose

Figure 3A:
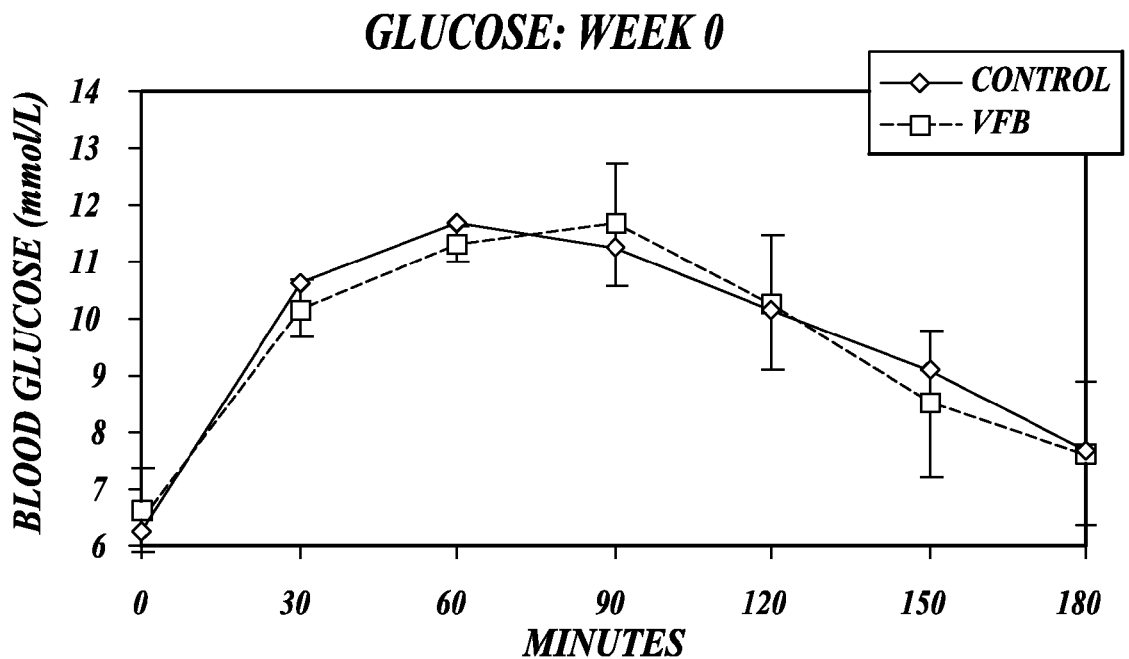
FIG. 3A graphically illustrates the acute postprandial glucose response in subjects provided with control and test breakfasts as measured at the beginning of the study, as described in EXAMPLE 2.
Figure 3B:
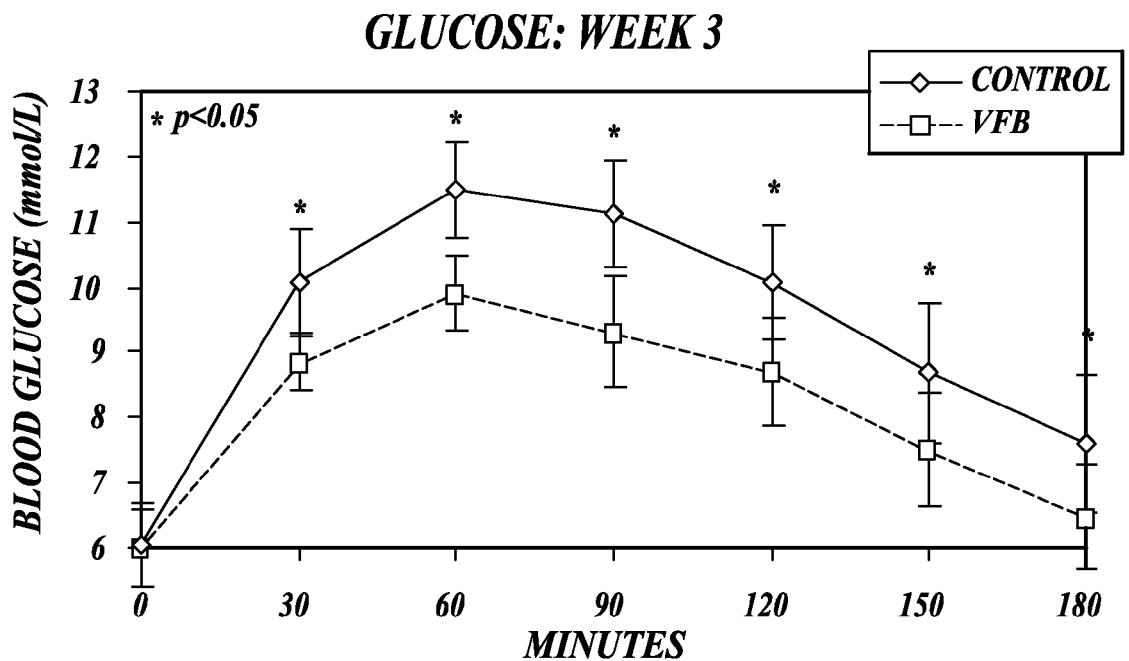
FIG. 3B graphically illustrates the acute postprandial glucose response in subjects provided with control and test breakfasts as measured during the third week of the study, as described in EXAMPLE 2.

FIGS. 3A-B and TABLE 16 show a comparison of the acute postprandial glucose response in subjects provided with control and test VFB breakfasts. Subjects were given either the control breakfast or the test breakfast everyday for three weeks. Their blood glucose response was measured at the beginning of the study (week 0) and at the end of the study (week 3). All data points are Means±SD. Significant differences at $p<0.05$ are indicated by an asterisk.

Figure 4:
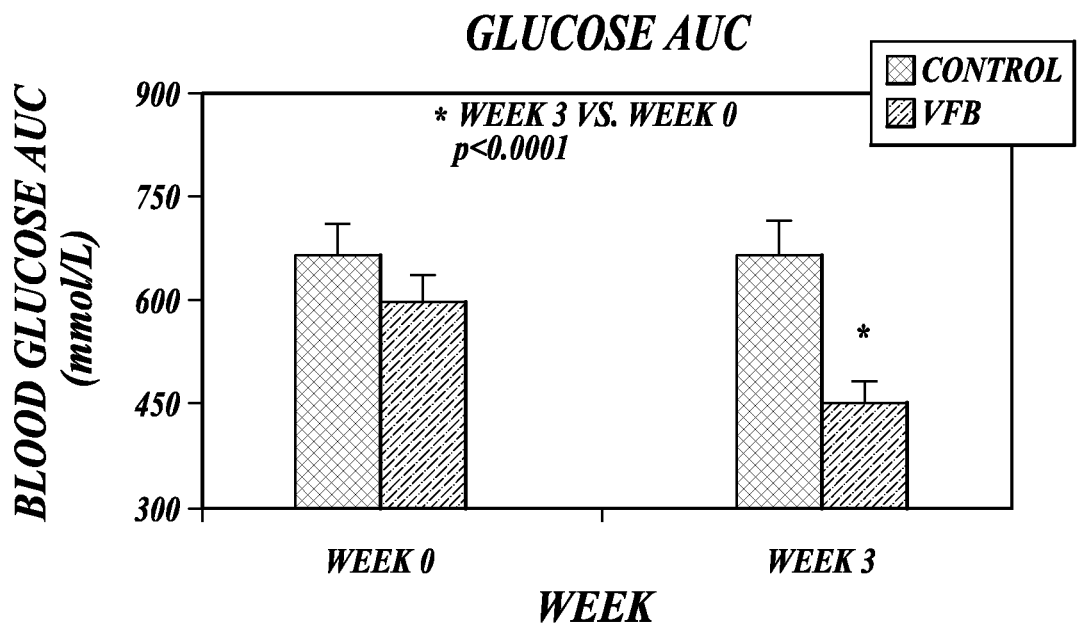
FIG. 4 shows the area under the curves for postprandial glucose responses at week 0 and week 3 for control and VFB, as described in EXAMPLE 2. All data points are Means±SD. Significant differences at $p<0.05$ are indicated by an asterisk.

FIG. 4 shows the area under the curve (AUC) for postprandial glucose response at week 0 and week 3 for control and VFB. All data points are Means±SD. Significant differences at $p<0.05$ are indicated by an asterisk.

TABLE 16

Comparison of Blood Glucose Levels in Subjects Provided With Control and Test Breakfasts

| | Blood Glucose (mmol/L) | | | | | | | |
|---|---|---|---|---|---|---|---|---|
| | 0 min | 30 min | 60 min | 90 min | 120 min | 150 min | 180 min | AUC |
| | Week 0: Control | | | | | | | |
| MEAN | 6.28 | 10.63 | 11.66 | 11.26 | 10.18 | 9.09 | 7.67 | 663.75 |
| SEM | 0.56 | 0.65 | 0.61 | 0.77 | 0.90 | 1.01 | 0.97 | 45.01 |
| | Week 0: VFB Treatment | | | | | | | |
| MEAN | 6.62 | 10.17 | 11.30 | 11.66 | 10.28 | 8.50 | 7.62 | 594.48 |
| SEM | 0.75 | 0.49 | 0.32 | 1.07 | 1.20 | 1.27 | 1.26 | 39.22 |

TABLE 16-continued

Comparison of Blood Glucose Levels in Subjects
Provided With Control and Test Breakfasts

| | Blood Glucose (mmol/L) | | | | | | |
|---|---|---|---|---|---|---|---|
| | 0 min | 30 min | 60 min | 90 min | 120 min | 150 min | 180 min | AUC |
| Week 3: Control | | | | | | | | |
| MEAN | 6.03 | 10.06 | 11.48 | 11.14 | 10.08 | 8.69 | 7.61 | 666.39 |
| SEM | 0.64 | 0.83 | 0.72 | 0.83 | 0.87 | 1.07 | 1.07 | 46.13 |
| Week 3: VFB Treatment | | | | | | | | |
| MEAN | 6.01 | 8.86 | 9.91 | 9.30 | 8.71 | 7.51 | 6.46 | 451.38 |
| SEM | 0.59 | 0.42 | 0.56 | 0.85 | 0.83 | 0.86 | 0.80 | 28.28 |

5. Insulin

Figure 3C:
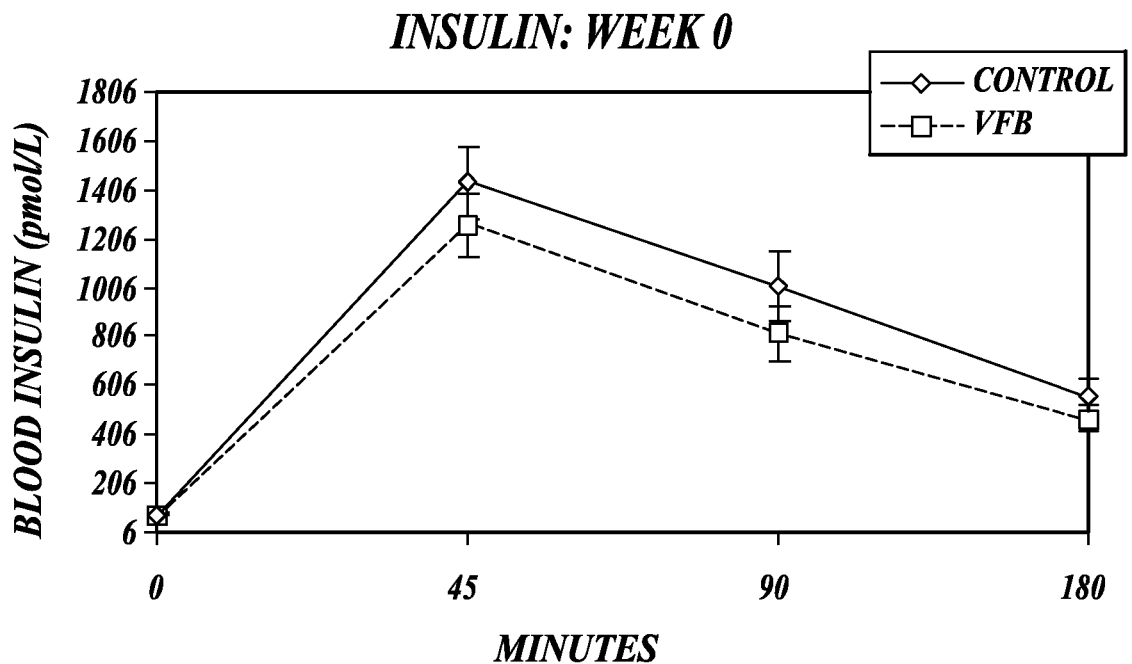
FIG. 3C graphically illustrates the postprandial insulin response in subjects provided with control and test breakfasts as measured at the beginning of the study, as described in EXAMPLE 2.
Figure 3D:
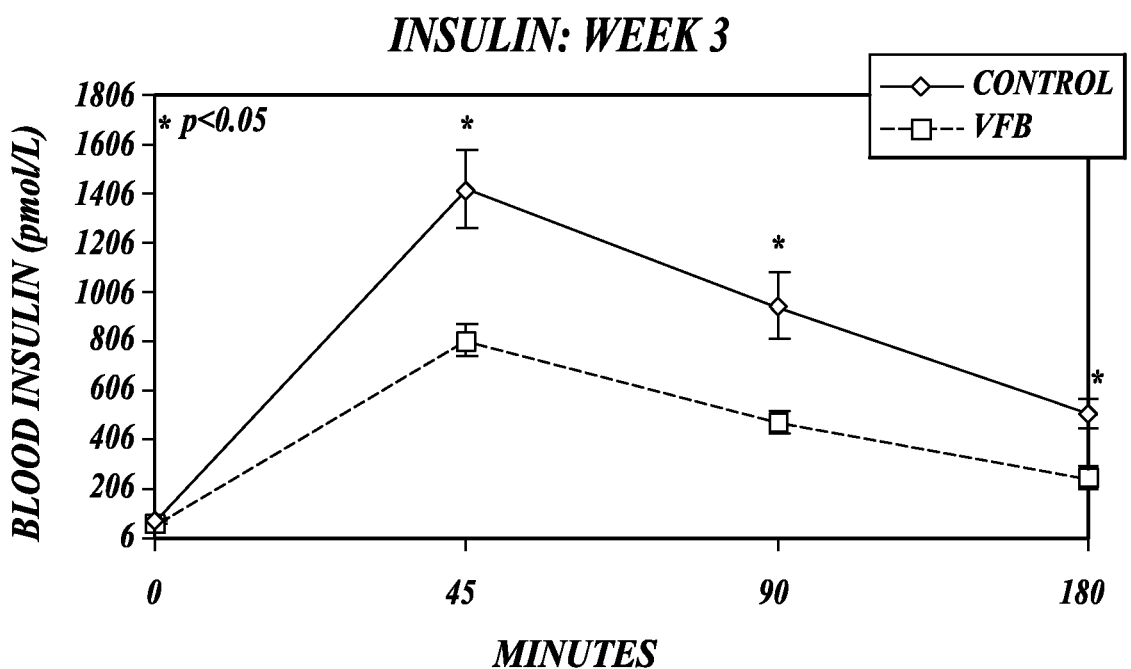
FIG. 3D graphically illustrates the postprandial insulin response in subjects provided with control and test breakfasts as measured during the third week of the study, as described in EXAMPLE 2.

FIGS. 3C-D and TABLE 17 show a comparison of the postprandial insulin response in subjects provided with control and test VFB breakfasts. Subjects were given either the control breakfast or the test breakfast everyday for three weeks. Their blood insulin response was measured at the beginning of the study (week 0) and at the end of the study (week 3). All data points are Means±SD. Significant differences at $p<0.05$ are indicated by an asterisk.

Figure 5:
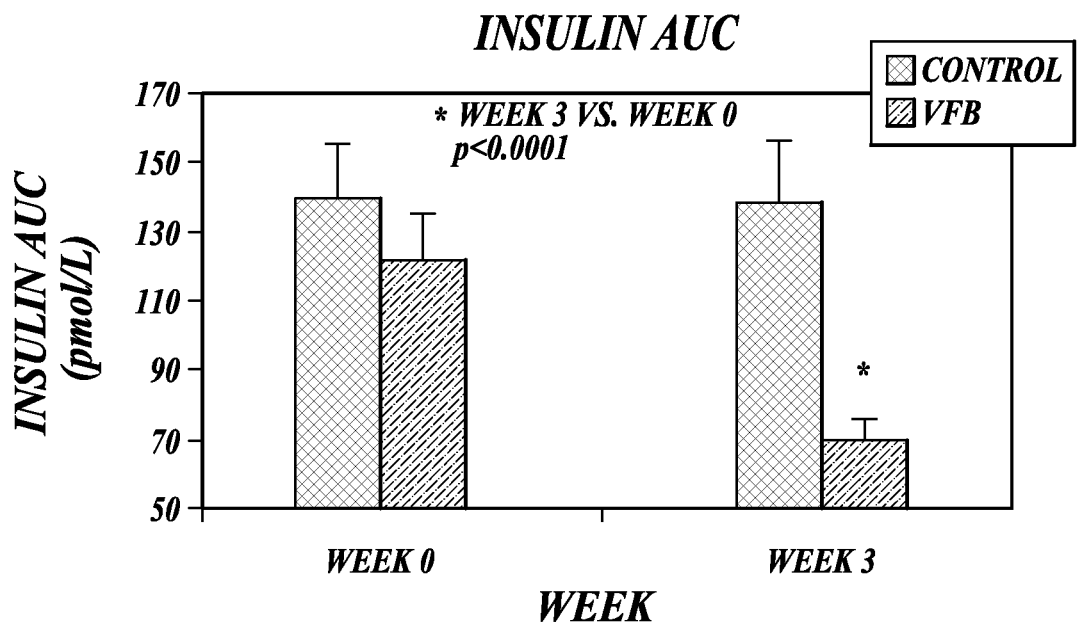
FIG. 5 shows the area under the curves for postprandial insulin responses at week 0 and week 3 for control and VFB, as described in EXAMPLE 2. All data points are Means±SD. Significant differences at $p<0.05$ are indicated by an asterisk.

FIG. 5 shows the area under the curve (AUC) for postprandial insulin response at week 0 and week 3 for control and VFB. All data points are Means±SD. Significant differences at $p<0.05$ are indicated by an asterisk.

TABLE 17

Comparison of Insulin Levels in Subjects
Provided With Control and Test Breakfasts

| | Blood Insulin (pmol/L) | | | | |
|---|---|---|---|---|---|
| | 0 min | 45 min | 90 min | 180 min | AUC |
| Week 0: Control | | | | | |
| MEAN | 78.58 | 1436.58 | 1015.08 | 567.50 | 139.68 |
| SEM | 5.32 | 149.03 | 142.08 | 61.65 | 16.05 |
| Week 0: VFB Treatment | | | | | |
| MEAN | 80.67 | 1263.25 | 820.00 | 472.92 | 121.61 |
| SEM | 5.91 | 126.49 | 110.81 | 48.37 | 13.94 |
| Week 3: Control | | | | | |
| MEAN | 78.33 | 1420.42 | 949.75 | 515.25 | 138.81 |
| SEM | 7.85 | 161.39 | 137.58 | 58.68 | 17.60 |
| Week 3: VFB Treatment | | | | | |
| MEAN | 70.00 | 808.75 | 479.75 | 256.25 | 69.46 |
| SEM | 6.25 | 65.72 | 44.71 | 46.63 | 6.85 |

6. Percent Body Fat

Figure 6:
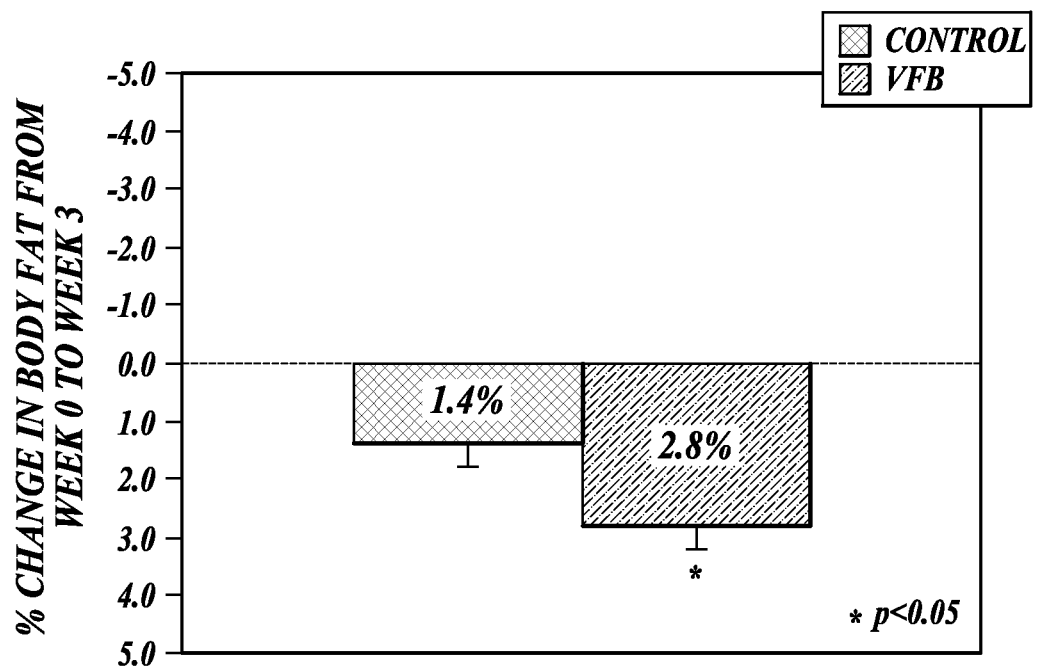
FIG. 6 graphically illustrates the change in percent body fat in subjects that consumed a test breakfast in comparison to subjects that consumed a control breakfast over a three-week period, as described in EXAMPLE 2.

An infrared interactance Futrex-5000® system (Futrex Inc., Gaithersburg, Md.) was used to assess body composition. FIG. 6 and TABLE 18 illustrate the change in percent body fat from week 0 to week 3 during the control in which participants consumed the control breakfast compared to the period in which participants consumed the test breakfast. Data are represented as means. Significant differences at $p<0.05$ are indicated by an asterisk.

TABLE 18

Change in Percent Body Fat in Subjects Provided
Control or Test (VFB) Breakfasts

| | Change in Percent Body Fat From Week 0 to Week 3 | |
|---|---|---|
| Breakfast | MEAN | SEM |
| Control | −1.4 | 0.7 |
| VFB treatment | −2.8* | 0.4 |

Conclusions

Areas under the curves for glycemia (−23.13.5% vs. 0.42.3%, P=0.000022) and insulinemia (−40.54.5% vs. 2.02.9%, p=0.000012) were significantly reduced with VFB, compared to control. These decreases translated into a significant increase in insulin sensitivity after consumption of VFB compared to control (55.99.2% vs. 9.74.5%, P=0.00056). In addition, body fat was reduced by 2.8% from baseline following the 3-week period with VFB, compared to the control group, which experienced 1.4% body fat reduction ($p<0.05$). We concluded that prolonged consumption of VFB reduces body fat in individuals with impaired insulin sensitivity in the metabolic syndrome. A possible explanation includes an improvement in insulin sensitivity.

Example 3

This example provides an exemplary embodiment of a meal replacement product comprising a dietary fiber composition of the invention.

An exemplary dietary fiber blend (VFB) was made by combining glucomannan (greater than 80% pure from Konjac root), Xanthan gum (commercially sourced extracellular heteropolysaccharide from *Xanthomonas* bacteria), and alginate (commercially sourced medium viscosity sodium alginate from *Ascophyllum nodosum*). The composition of an exemplary dietary fiber blend (VFB) is shown in TABLE 19.

TABLE 19

VFB Fiber Blend Composition

| Ingredient | Amount |
|---|---|
| Glucomannan | 3500 mg (70%) |
| Xanthan Gum | 850 mg (17%) |
| Alginate | 650 mg (13%) |
| Total | 5000 mg |

A meal replacement product was formulated with the VFB fiber blend as shown in TABLE 20.

TABLE 20

Meal Replacement Composition

| Ingredient | Amount |
|---|---|
| Whey protein | 44% |
| Fructose | 14% |
| VFB fiber blend | 9% |
| Xylitol | 8% |
| Flavor | 8% |
| Lecithin | 7% |
| Vitamins and Minerals | 6% |
| Medium chain triglycerides | 4% |

TABLE 21 shows the vitamin and mineral provided per serving of the meal replacement product (RE=retinol equivalent units, NE=niacin equivalent units, mcg=microgram, mg=milligram).

TABLE 21

Vitamin and Mineral Provided Per Serving

| Vitamin A | 630 | RE |
|---|---|---|
| Vitamin D | 2.5 | Mcg |
| Vitamin E | 4.4118 | Mg |
| Vitamin C | 20 | Mg |
| Thiamine | 750 | Mcg |
| Riboflavin | 800 | Mcg |
| Niacin | 12 | NE |
| Vitamin B6 | 750 | Mcg |
| Vitamin B12 | 0.75 | Mcg |
| Folacin | 120 | Mcg |
| Pantothenic acid | 2.5 | Mg |
| Biotin | 75 | Mcg |
| Calcium | 400.5736 | Mg |
| Phosphorus | 250 | Mg |
| Iron | 2.77324 | Mg |
| Iodide | 40 | Mcg |
| Magnesium | 120 | Mg |
| Copper | 0.5 | Mg |
| Zinc | 6 | Mg |
| Potassium | 399.6344 | Mg |
| Sodium | 354.3036 | Mg |
| Manganese | 1 | Mg |
| Selenium | 20 | Mcg |
| Chromium | 20 | Mcg |
| Molybdenum | 25 | Mcg |

The flavor of the meal replacement can include, but is not limited to, any of the following: chocolate, strawberry, vanilla, pineapple, mango, peach, orange, mocha, and cherry. This meal replacement is a powder form. Each serving is 57 grams, to be mixed with a glass of water. One serving is taken at breakfast and at lunch in place of a regular meal.

Example 4

This example illustrates the effects on volunteers of consuming a meal replacement product comprising the dietary fiber composition (VFB) of the invention.

A middle-aged male volunteer took the meal replacement product described in EXAMPLE 3 twice a day for a nine-month trial. At the start of the trial, the volunteer weighed 247.2 pounds, had a BMI of 36, a waist measurement of 45.25 inches, a hip measurement of 47.25 inches, and a body fat measurement of 27.7%. At the end of the nine-month trial, the volunteer weighed 223.75 pounds, has a waist measurement of 43 inches, a hip measurement of 45.5 inches, and a body fat measurement of 25.7%. The volunteer complained of stomachache, loose stools, and hunger in the evening when he did not take the meal replacement.

A middle-aged female volunteer took the meal replacement product described in EXAMPLE 3 twice a day for a nine-month trial. At the start of the trial, the volunteer weighed 170 pounds, had a BMI of 30.3, a waist measurement of 36.5 inches, a hip measurement of 43 inches, and a body fat measurement of 46.6%. At the end of the nine-month trial, the volunteer weighed 156 pounds, had a waist measurement of 33.5 inches, and a hip measurement of 41 inches. The volunteer complained of diarrhea during the first two days of the trial and found herself drinking more water due to thirst.

A middle-aged female volunteer took the meal replacement product described in EXAMPLE 3 twice a day for a nine-month trial. At the start of the trial, the volunteer weighed 162.5 pounds, had a BMI of 27.9, a waist measurement of 37 inches, a hip measurement of 43 inches, and a body fat measurement of 41.9%. At the end of the nine-month trial, the volunteer weighed 141 pounds, had a waist measurement of 34 inches, a hip measurement of 41 inches, and a body fat measurement of 35.3%. The volunteer complained of minor headache during the first two weeks of the trial.

A middle-aged female volunteer took the meal replacement product described in EXAMPLE 3 twice a day for a nine-month trial. At the start of the trial, the volunteer weighed 172 pounds, had a BMI of 27.7, a waist measurement of 35.75 inches, a hip measurement of 43 inches, and a body fat measurement of 41.6%. At the end of the nine-month trial, the volunteer weighed 143 pounds, had a waist measurement of 31 inches, and a hip measurement of 38.25 inches. The volunteer found the diet plan reasonable and flexible.

Example 5

This example provides an exemplary embodiment of a dietary fiber composition (VFB) of the invention formulated as gelatin capsules.

An exemplary dietary fiber composition was formulated as two-piece, hard-gelatin capsules, with each capsule containing 500 mg of the composition shown in TABLE 22.

TABLE 22

VFB Capsule Composition

| Ingredient | Amount |
|---|---|
| Glucomannan | 350 mg (47.62%) |
| Xanthan Gum | 85 mg (11.56%) |
| Alginate | 65 mg (8.84%) |
| Rice Flour | 228 mg (31.02%) |
| Magnesium Stearate | 7 mg (0.95%) |
| Total | 735 mg |

Example 6

This example provides an exemplary embodiment of a dietary fiber composition of the invention formulated as an appetite control powder.

An exemplary dietary fiber composition was formulated as an appetite control power. Each bottle contains 182 g, which represents 26 servings. The contents per serving of the appetite control powder are shown in TABLE 23.

TABLE 23

Contents per Serving of SlimStyles Appetite Control Powder

| Ingredient | Amount |
|---|---|
| Glucomannan | 3.5 mg (50%) |
| Xanthan Gum | 0.65002 mg (9.29%) |
| Alginate | 0.85001 mg (12.14%) |
| Xylitol | 0.72898 mg (10.41%) |
| Lecithin | 0.04998 mg (0.71%) |
| Medium Chain Triglycerides | 0.04998 mg (0.71%) |
| Natural Orange Juice Flavor | 0.72002 mg (10.29%) |
| Orange Flavor | 0.36001 mg (5.14%) |
| Stevia Powder | 0.07497 mg (1.07%) |
| Syloid Silica | 0.01603 mg (0.12%) |
| Total | 7 mg |

Example 7

This example provides an exemplary embodiment of a dietary fiber composition (VFB) of the invention formulated as a meal replacement smoothie.

An exemplary dietary fiber composition was formulated as a meal replacement smoothie. The contents per serving of the meal replacement smoothie are shown in TABLE 24.

TABLE 24

Contents per Serving of SlimStyles Meal Replacement Smoothie

| Ingredient | Amount |
|---|---|
| Whey protein | 24.5 g (42.87%) |
| Ca (from Ca citrate) | 77 mg (0.67%) |
| Total Ca | 400.5736 mg |
| Mg (from Mg citrate) | 120 mg (1.38%) |
| Iron (from Fe fumarate) | 2.5 mg (0.01%) |
| Zn (from Zn citrate) | 6 mg (0.03%) |
| Se (rice chelate) | 20 mcg (0.01%) |
| Cr (from Cr chelate) | 20 mcg (0.00%) |
| Cu (from Cu chelate) | 0.5 mg (0.01%) |
| Mo (from Mo citrate) | 25 mcg (0.01%) |
| Mn (from Mn citrate) | 1 mg (0.01%) |
| Potassium citrate | 20 mg (0.10%) |
| I (KI) | 40 mcg (0.00%) |
| P (Calcium phosphate dehydrate) | 250 mg (2.63%) |
| Na (sodium chloride) | 55 mg (0.24%) |
| Beta Carotene | 6300 iu (0.04%) |
| Vitamin D2 | 100 iu (0.00%) |
| Vitamin E (acetate) | 6 iu (0.01%) |
| B1 thiamin HCl | 0.75 mg (0.00%) |
| B2 riboflavin | 0.8 mg (0.00%) |
| B3 niacinamide | 12 mg (0.02%) |
| Pantothenic acid (Ca Panto) | 2.5 mg (0.01%) |
| Folic Acid | 0.12 mg (0.00%) |
| B6 pyridoxine HCl | 0.75 mg (0.00%) |
| B12 cyanocobalamin | 0.5 mg (0.00%) |
| Biotin | 75 mcg (0.01%) |
| Vitamin C | 20 mg (0.04%) |
| Glucomannan | 3.5 g (6.12%) |
| Xanthan Gum | 0.65 mg (1.14%) |
| Sodium Alginate | 0.85 g (1.5%) |
| Stevia | 150 mg (0.26%) |
| Fructose | 7 g (12.25%) |
| Xylitol | 0.72898 mg (10.41%) |

TABLE 24-continued

Contents per Serving of SlimStyles Meal Replacement Smoothie

| Ingredient | Amount |
|---|---|
| Chocolate Flavor | 1.3 g (2.27%) |
| Cocoa | 1 g (1.75%) |
| Coffee (Rich blend) | 2.3 g (4.02%) |
| Cream Flavor | 1.1 g (1.92%) |
| Lecithin | 4.4 g (7.70%) |
| Medium Chain Triglycerides | 2.4 g (4.20%) |
| Total | (100%) |

Example 8

This example describes a comparison of the viscosity profile of an exemplary fiber blend (VFB) to other fiber blends under various conditions.

Methods

A formulation of viscous fiber blend (VFB) was created which included 70% glucomannan (konjac), 13% xanthan and 17% alginate, as described in EXAMPLE 1. The VFB was compared with a konjac/xanthan (70:30) fiber blend and a konjac/alginate (70:30) fiber blend in distilled water, gastric conditions and intestinal conditions as follows.

Compositions Tested:

(1) VFB: konjac (70%)/xanthan (13%)/alginate (17%)

(2) KX: konjac (70%)/xanthan (30%)

(3) KA: Konjac (70%)/alginate (30%)

Viscosity Profile Experiments:

Five grams of test material was mixed with 350 g of fluid (either distilled water, gastric, or intestinal juice). The sample was blended for 30 seconds on low speed 2 on a Proctor/Silex blender. Viscosity readings were taken at 5, 10, 15, 20, 30, 45, 60, and 120 minutes. Gastric and intestinal fluids were prepared according to Universal Sample Preparation (USP) methodology.

Results

Figure 9:
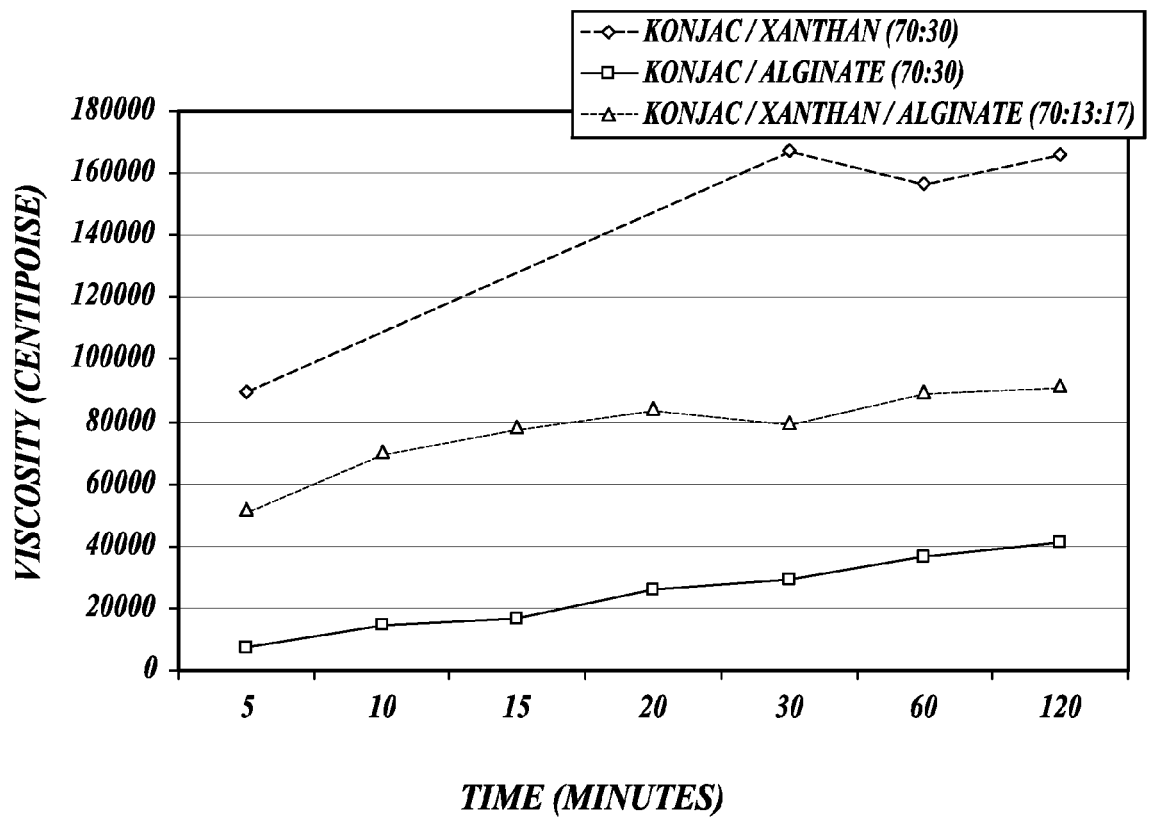
FIG. 9 graphically illustrates the viscosity profile of various fiber blends over time under intestinal conditions, as described in EXAMPLE 8.

TABLE 25 and FIG. 7 compare the viscosity profile of VFB compared with KX and KA under normal conditions (distilled water). TABLE 26 and FIG. 8 compare the viscosity profile of VFB compared with KX and KA under gastric conditions. TABLE 27 and FIG. 9 compare the viscosity profile of VFB compared with KX and KA under intestinal conditions. As shown in FIGS. 7, 8, and 9, the KA (konjac/alginate 70:30) fiber blend consistently has the lowest viscosity of the three fiber blends tested. Under neutral and gastric conditions the KX (konjac/xanthan 70:30) reaches maximum viscosity quickly (e.g., within about 15-20 minutes). The VFB blend (konjac (70%)/xanthan (13%)/alginate (17%)) starts at about the same viscosity as KA under neutral conditions, increases in viscosity over time under both gastric and intestinal conditions and eventually reaches a greater viscosity than KX under neutral and gastric conditions. This combination also produces unexpectedly high viscosity values after 10 minutes when blended with gastric juice. Therefore, the addition of alginate to the KX combination unexpectedly provides a decrease in viscosity of VFB at neutral conditions and results in a greater viscosity than KX alone over time.

TABLE 25

Viscosity Profile Comparison of VFB and Various Fiber Blends in Distilled Water

| Fiber Blend | 5 min | 10 min | 15 min | 20 min | 30 min | 60 min | 120 min | avg temp | pH |
|---|---|---|---|---|---|---|---|---|---|
| KX: konjac/xanthan (70:30) | 53380 | 49080 | 47870 | 43950 | 49810 | 49251 | 47440 | 20.2 | 6.05 |
| KA: konjac/alginate (70:30) | 3960 | 11470 | 16730 | 18420 | 25940 | 43530 | 78850 | 20.2 | 6.35 |
| VFB (konjac/xanthan/alginate (70:13:17)) | 4230 | 9230 | 16700 | 34970 | 43170 | 46010 | 90000 | 20.8 | 6.17 |

TABLE 26

Viscosity Profile Comparison of VFB and Various Fiber Blends Under Gastric Conditions

| Fiber Blend | 5 min | 10 min | 15 min | 20 min | 30 min | 60 min | 120 min | avg temp | pH |
|---|---|---|---|---|---|---|---|---|---|
| KX: konjac/xanthan (70:30) | 35500 | 48020 | 70150 | 75400 | 78720 | 83290 | 87680 | 20.3 | 1.46 |
| KA: konjac/alginate (70:30) | 3210 | 11820 | 17664 | 18820 | 23580 | 29130 | 43460 | 20.2 | 3.85 |
| VFB (konjac/xanthan/alginate (70:13:17)) | 44880 | 90000 | 116500 | 123600 | 135200 | 139600 | 249000 | 20.5 | 3.69 |

TABLE 27

Viscosity Profile Comparison of VFB and Various Fiber Blends Under Intestinal Conditions

| Fiber Blend | 5 min | 10 min | 15 min | 20 min | 30 min | 60 min | 120 min | avg temp | pH |
|---|---|---|---|---|---|---|---|---|---|
| KX: konjac/xanthan (70:30) | 90000 | nd | nd | nd | 167500 | 156800 | 166200 | 20.2 | 7.88 |
| KA: konjac/alginate (70:30) | 6990 | 14470 | 16350 | 26030 | 29110 | 36600 | 40900 | 20.1 | 7.89 |
| VFB (konjac/xanthan/alginate (70:13:17)) | 51490 | 70180 | 78640 | 84100 | 79480 | 90000 | 91900 | 20.5 | 7.92 |

Example 9

This example describes the preparation of soft gelatin (softgel) capsule containing Viscous Fiber Blend mixed with medium chain triglycerides.

Methods

Preparation of a Soft Gelatin Capsule Containing Viscous Fiber Blend:

Inner Filling

A soft gelatin capsule was prepared with an inner filling including Viscous Fiber Blend (konjac/xanthan/alginate (70:13:17)) and an oil (e.g., medium chain triglycerides (MCT) at a ratio of from 0.01:99.99 up to 80:20 (w/w VFB:MCT). An example of a ratio of VFB:MCT of 52.7:47.3 w/w is shown below in TABLE 28. The MCT can be substituted with any of the following oils: soy bean oil, palm kernel oil, fish oil, and canola oil.

TABLE 28

Exemplary Inner Filling Ingredients for Capsules

| Capsule weight (inner filling) | VFB (konjac/xanthan/alginate (70:13:17) | Medium chain triglycerides (MCT) |
|---|---|---|
| 100 mg | 52.7 mg | 47.3 mg |
| 1500 mg | 790 mg | 710 mg |
| 2,500 mg | 1320 mg | 1180 mg |

Outer Capsule Shell

The outer capsule shell includes a mixture of gelatin, glycerin, and water.

An exemplary softgel capsule was produced as follows:
Inner Filling:
790 mg VFB
710 mg MCT
Outer Capsule Shell:
2,130 mg of a mixture consisting of gelatin, glycerin and water was used.

The proportion of outer capsule shell to inner filling may be varied to accommodate various capsule sizes, as shown in TABLE 28.

The softgel capsule containing VFB mixed with medium chain triglycerides is effective to delay the VFB viscous effects in water, while allowing for maximum viscosity of the VFB under gastric conditions, as demonstrated in EXAMPLE 10.

Example 10

This example demonstrates that VFB encapsulated in an oil-based softgel capsule is effective to delay its viscous effects in water in order to reduce potential choking hazard, while at the same time quickly reaching maximum viscosity under gastric conditions.

Methods

The viscosity profile of VFB encapsulated in an oil-based softgel capsule was compared in distilled water and gastric juice.

Soft gelatin capsules containing VFB mixed with oil were prepared as described in EXAMPLE 9. Each capsule contained 790 mg VFB (konjac/xanthan/alginate (70:13:17)). Six capsules (a total of 4.74 g VFB) were dissolved in a total volume of either 331.8 distilled $H_2O$ or gastric juice (prepared according to USP guidelines) for a 5 g VFB:350 g $H_2O$ ratio.

The samples were placed in the liquid medium in a vessel placed in a 25° C. water bath. After 15 minutes in liquid, the softened capsules were broken open using a spoon. The mixture was then mixed manually for 5 minutes, then put into a blender and mixed mechanically at 4,000 rpm for 30 seconds, followed by mixing at 8,000 rpm for an additional 30 seconds. Viscosity readings were taken at time intervals over a 3-hour period.

Results:

The viscosity profile of VFB softgel capsules in distilled water is shown below in TABLE 29.

TABLE 29

Viscosity Profile of VFB (Koniac/Xanthan/Alginate (70:13:17)) Plus oil (710 mg MCT) Encapsulated in a Softgel Outer Capsule (2,130 mg of a Mixture Consisting of Gelatin, Glycerin, and water) as Measured in Distilled Water

| Time (a) (minutes elapsed after capsules were added to water) | Time (b) (minutes elapsed after capsules were blended in water) | Spindle: R3 viscosity (centipoise) | RPM |
|---|---|---|---|
| 25 | 5 | 3500 | 10 |
| 48 | 28 | 9350 | 5 |
| 63 | 43 | 19630 | 2.5 |
| 80 | 60 | 39660 | 1 |
| 108 | 88 | 48350 | 1 |
| 139 | 119 | 60180 | 1 |
| 180 | 160 | 63590 | 1 |

The viscosity profile of VFB softgel capsules in gastric juice is shown below in TABLE 30.

TABLE 30

Viscosity Profile of VFB (Konjac/Xanthan/Alginate (70:13:17)) Plus Oil (710 Mg Mct) Encapsulated in a Softgel Outer Capsule (2130 Mg of a Mixture Consisting of Gelatin, Glycerin, and Water) as Measured in Gastric Juice

| Time (a) (minutes elapsed after capsules were added to gastric juice) | Time (b) (minutes elapsed after capsules were blended in gastric juice) | Spindle: R3 Viscosity (centipoise) | RPM |
|---|---|---|---|
| 25 | 5 | >90000 | 1 |

TABLE 31

Comparison of Viscosity of VFB Softgel Capsules in Water and Gastric Juice

| Time (b) (minutes elapsed after capsules were blended (minutes) | Viscosity in Water | Viscosity in Gastric Juice |
|---|---|---|
| 5 | 3,500 | >90000 |
| 28 | 9350 | |
| 43 | 19630 | |
| 60 | 39660 | |
| 88 | 48350 | |
| 119 | 60180 | |
| 160 | 65590 | |

As shown in TABLES 30-31, under gastric conditions, the oil-based VFB delivered in softgel capsules thickened quickly (within 5 minutes) after blending, reaching a viscosity of greater than 90,000 centipoise. In contrast, as shown in TABLES 29 and 31, the oil-based VFB delivered in softgel capsules thickened slowly in distilled water, resulting in a viscosity level of 3,500 at five minutes after blending and gradually increasing to a maximum of 65,000 centipoise at 160 minutes after blending. As shown in TABLE 29, the VFB delivered in softgel capsules took 60 minutes to reach a viscosity of 19,630 cps in distilled water and it did not reach 90,000 cps even after over 3 hours. This result is significantly different from the behavior observed for VFB (non-granulated, without oil-based capsule) when stirred into water, which reached 90,000 cps at 120 minutes, as shown in EXAMPLE 1, TABLE 9 herein. In fact, it is noted that the time delay observed in reaching maximum viscosity for VFB delivered in softgel capsules is even more pronounced than that observed for granulated VFB mesh size 40 and mesh size 60, each of which reached 90,000 cps at 120 minutes (see TABLE 9 herein). These results indicate that the addition of oil to VFB is effective to delay its viscous effects when mixed with water. Therefore, the combination of VFB with oil may be used in order to avoid a potential choking hazard during administration of VFB to an individual, since it has been observed that VFB alone becomes viscous very quickly in water and could form large clumps.

Moreover, in contrast to the delayed viscosity observed in water, the VFB delivered in softgel capsules reached 90,000 cps within 5 minutes after contact with gastric conditions, as shown in TABLES 30 and 31. This high viscosity was maintained over time (data not shown). It was surprising that the combination of VFB with oil could reach 90,000 cps within such a short time under gastric conditions. It is important to note that this viscosity profile for VFB in softgel capsules was very different from that observed with VFB alone under gastric conditions (shown in TABLE 6 herein), which was not observed to reach such high viscosities even after 60 minutes. As shown in TABLE 6, VFB alone only reached 3,600 cps after 60 minutes.

Therefore, the results described in this example that were observed with VFB in softgel capsules, including the delay in viscosity in water, and the rapid high viscosity level reached under gastric conditions, demonstrate that the combination of VFB and oil may be used to produce the desired effect of a feeling of fullness in the stomach and reduce the sensation of hunger in an individual while reducing the risk of choking during ingestion.

While not wishing to be bound by theory, the beneficial results described in this example for the combination of VFB and oil may be due to the coating of oil over the fiber. With regard to the delayed viscosity observed in water, it is likely that the oil coats and separates the particles such that water does not cause the particles to clump together and limit their dispersion. However, under gastric conditions, the acidity and gastric enzymes would likely strip off at least a portion of the oil coating such that VFB fibers could quickly reach maximum viscosity. Moreover, in contrast to dispersion of VFB (without oil coating) in water, which yields some clumping, the combination of VFB with oil avoids the clumping in water, which leads to lower initial overall viscosity in water, and thereby allows for an eventual higher viscosity over time because of the ability of the VFB and oil combination to disperse more evenly to allow more fiber particles to react with water instead of forming clumps.

Example 11

This example describes the effect of various particle sizes of granulated viscous fiber blend administered in either solid or liquid meals on the postprandial glycemic response in healthy individuals.

Rationale

The objective of this study was to determine the glycemic index of two different granule sizes of the viscous fiber blend (konjac/xanthan/alginate (70:13:17), VFB100 (granulated to a smaller mesh size) and VFB300 (granulated to a larger mesh size) administered in solid form (white bread) or in liquid form (glucodex). The VFB100 contains only particles that are finer than 40 mesh. The VFB300 contains only particles that are finer than 20 mesh. Ungranulated VFB (konjac/xanthan/alginate (70:13:17)) has a mesh size of approximately 200 mesh.

Methods

In a random cross-over designed study, ten healthy individuals (five men and five women, x±SEM age: 21±2y) were included in this study. Subjects with any known health conditions, such as diabetes, hypertension, and obesity, were excluded from the study. Each study participant received a total of eight treatments in a randomized, double-blind cross-over design. To examine the effects of VFB100 and VFB300 in different food forms, white bread and glucose drink (glucodex) were prepared as follows. VFB100 and VFB300 were prepared as described in EXAMPLE 1. The five white bread treatments included either baked in VFB100, VFB300, or no VFB included as standardized controls. The three drink treatments included either mixed in VFB100, VFB300, or no VFB (control). All preparations and baking of the white bread with the various VFB granule sizes were done by one person in order to minimize variability between test samples. Study participants were blinded to the identity of the placebo and VFB treatments by coding and by the indistinguishable nature of the fiber in the bread or drinks. To ensure stability, the VFB100 and VFB300 were both stored in a cool, dry location over the course of the study.

Each subject was given eight treatments as follows:
  50 g of white bread control with no VFB, consumed with 300 ml water (solid food control was repeated 3 times by each subject)
  50 g of white bread with 3 grams of VFB100 consumed with 300 ml water
  50 g of white bread with 3 grams of VFB300 consumed with 300 ml water
  50 g of glucodex (liquid control) consumed with 300 ml water
  50 g of Glucodex diluted in 300 ml with 3 grams VFB100
  50 g of Glucodex diluted in 300 ml with 3 grams VFB300

Study participants were given eight treatments on eight separated mornings after a 10- to 12-hour overnight fast. The study was done over a two month period. To minimize carry-over effects, there were at least three days of separation between each treatment. Each participant was instructed to maintain the same dietary and exercise pattern the evening before each treatment and to consume at least 150 g of carbohydrates each day for three days before each treatment. To ensure that these instructions were followed, participants completed a questionnaire that detailed pre-session information about their diet and lifestyle patterns for each visit. No adverse effects were reported by any of the study participants.

At the start of each treatment, a blood sample was obtained from each participant using a 250 µL fasting finger prick capillary collected with a Monoejector Lancet Device (Owen Mumford Ltd., Woodstock, Oxon, England). One of the eight treatments was then administered over a period of 5 minutes. An additional finger-prick blood sample was obtained at 15, 30, 45, 60, 90, and 120 minutes after the start of treatment (t=0), for a total of seven collection tubes per participant per treatment.

Blood Glucose Analysis:

All blood samples were collected in tubes containing fluoride oxalate, frozen immediately at −20° C. pending analysis, and analyzed within three days of collection. The glucose concentration was determined by the glucose oxidate method with the use of a YSI 2300 Stat glucose/L-lactate analyzer, model 115 (Yellow springs, Ohio). The interassay CVs of this method for two sample pools were 3.3% (3.99±0.013 mmol/L; n=91) and 1.8% (14.35±-/26 mmol/L; n=89).

Statistical Analysis:

The postprandial serum blood glucose curves were plotted as the incremental change in blood glucose over time and the positive incremental area under the curve (AUC) was calculated geometrically for each participant. Blood glucose concentrations were used to control for fasting differences between the treatments. The Number Cruncher Statistical System (NCSS statistical software, Kaysville, Utah) was used for the statistical analysis purposes. The independent and interactive effect of treatment doses and meals on AUC was assessed by repeated measurements of two-way analysis of variance (ANOVA). Repeated measurements of two-way ANOVA assessed the interactive and independent effects of each pairing of each of the two factors; treatment×administration time, treatment×sampling time, and administration time×sampling time. If the interaction term was significant, then further two-way ANOVAs assessed the interactive and independent effect of treatment and administration time on incremental glycemia at each postprandial sampling point (15, 30, 45, 60, 90, 120 minutes) and on the AUCs. Adjustment with Tukey-Kramer test was done for contrasting means among both the treatment doses and the administration times to control for multiple comparisons. Repeated measurements of one-way ANOVA were used to measure the pair-wise differences between treatments in AUC and incremental glycemia at each time point in the test (15, 30, 45, 60, 90, and 120 minutes). The results are expressed as Mean±SD and $p<0.05$ is considered statistically significant.

Results

Two-way ANOVA showed a significant effect of treatment ($p<0.001$) and time ($p<0.001$) on incremental glycemia with a significant interaction ($p<0.0001$). Because the interaction terms for the two-way ANOVA were significant, the effect of treatments was assessed at each postprandial sampling time point and for the AUCs.

Solid Food (White Bread)

Figure 10A:
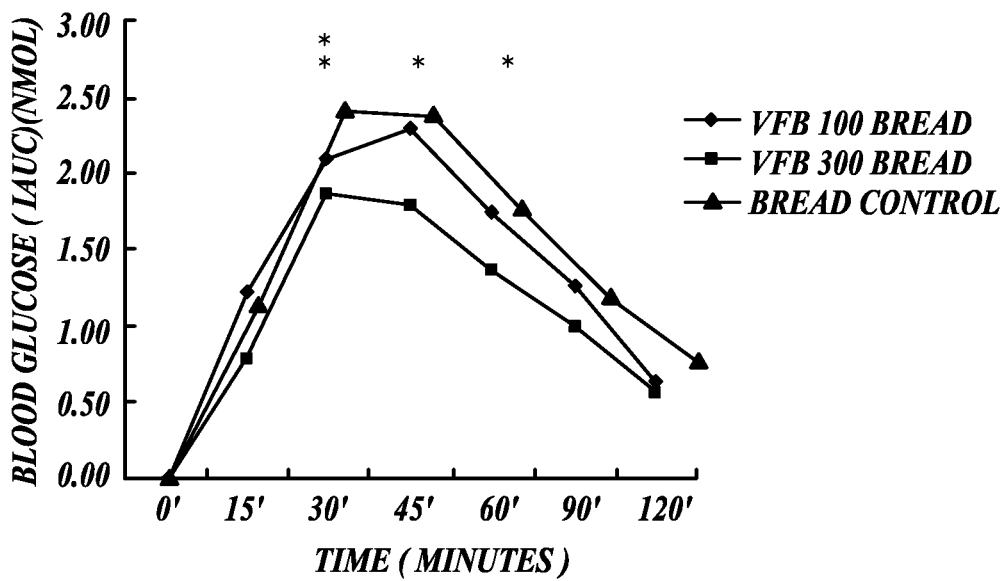
FIG. 10A graphically illustrates the incremental changes in blood glucose after treatment of a plurality of subjects with solid food (white bread), white bread plus VFB100 or white bread plus VFB300, as described in EXAMPLE 11.
Figure 10B:
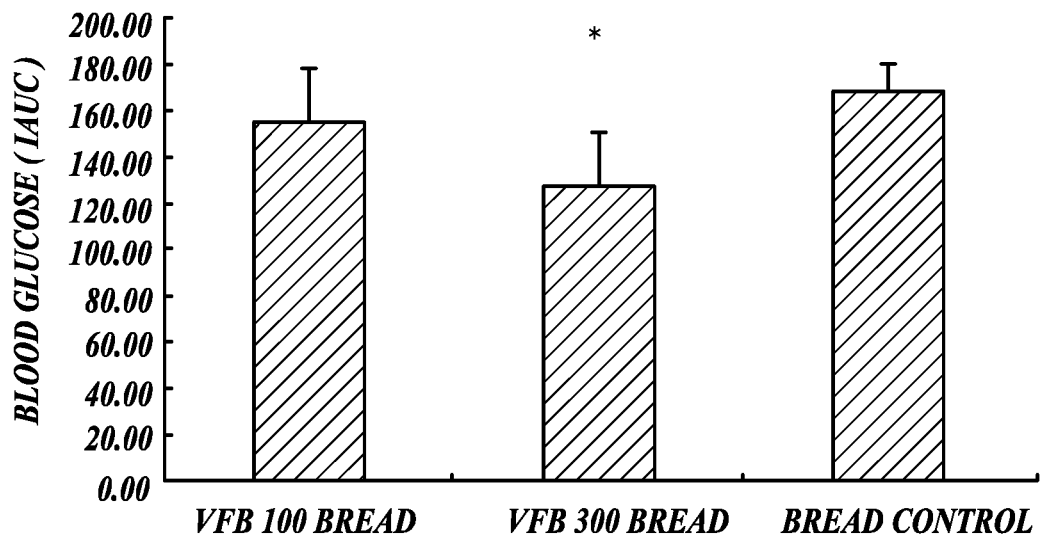
FIG. 10B graphically illustrates the incremental area under the curve (IAUC) in postprandial blood glucose after treatment of a plurality of subjects with the bread treatments shown in FIG. 10A, as described in EXAMPLE 11.

FIG. 10A graphically illustrates the incremental changes in blood glucose for each treatment with solid food (white bread), white bread plus VFB100 or white bread plus VFB300. Repeated measurements of two-way analysis of variance (ANOVA) applied to these data demonstrated a significant effect of time and treatment, as well as a significant interaction (p=0.0007). The "*" symbols in FIG. 10A represent a significant difference ($p<0.05$) in blood glucose levels between treatment and control at a particular time point. As shown in FIG. 10A, at 30, 45, and 60 minutes, the blood glucose levels in VFB300 were significantly lower than that in the control ($p<0.05$). There was no significant difference between VFB100 and VFB300 and the white bread control (w/o VFB) at 0, 90, and 120 time points. In addition, at 15-, 30-, 45- and 60-minute time points there were no significant differences between VFB100 and VFB300 bread treatments. At the 30-minute time points, both VFB100 and VFB300 bread treatments were significantly lower than the white bread control ($p<0.05$). FIG. 10B graphically illustrates the incremental area under the curve (IAUC) in postprandial blood glucose in a plurality of subjects after treatment with solid food (white bread), white bread plus VFB100 or white bread plus VFB300. The "*" symbol in FIG. 10B represents a significant difference (p<0.05) in blood glucose levels between treatment and control. As shown in FIG. 10B, the IAUC in VFB300 treatment is significantly lower when compared to the mean white bread controls (p<0.05), but the IAUC in VFB100 treatment and the white bread did not differ significantly. In addition, no significant difference was detected between the VFB100 and VFB300 treatments in bread.

Liquid (Glucose Drink)

Figure 11A:
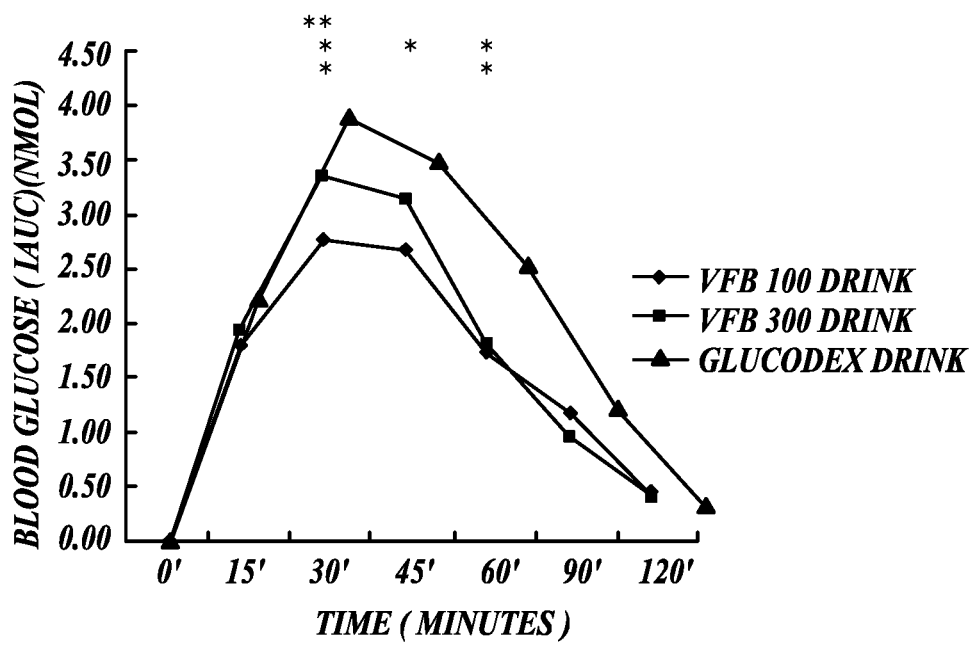
FIG. 11A graphically illustrates the incremental changes in blood glucose after treatment of a plurality of subjects with a glucose drink control, glucose drink plus VFB100, or glucose drink plus VFB300, as described in EXAMPLE 11.

The incremental changes in blood glucose for each treatment with glucose control drink, glucose drink plus VFB100, or glucose drink plus VFB300 are shown in FIG. 11A. The "*" symbols in FIG. 11A represent a significant difference (p<0.05) in blood glucose levels between treatment and control at a particular time point. As shown, repeated measures of two-way analysis of variance (ANOVA) found that there was a significant effect of time and treatments, as well as a significant interaction (p=0.0007). There was no significant difference observed between VFB100 and VFB300 and the glucose drink (glucodex) control at 0-, 90-, and 120-minutes points. At 30, 45, and 60 minutes, VFB100 was found to significantly lower blood glucose levels as compared to the control (p<0.05). At 15-, 45-, and 60-minute time points there was no significant difference observed between VFB100 and VFB300 drink treatments. At 15- and 60-minute time points, both VFB100 and VFB300 drink treatments were observed to significantly lower blood glucose as compared to the control (p<0.05). Also, at the 30-minute time point, the VFB100 drink was significantly lower than the VFB300 drink treatment (p=0.003). At the 45-minute time point, the VFB100 drink was significantly lower than the control (p=0.025); however at this time point there was no significant difference observed between VFB300 and the control.

Figure 11B:
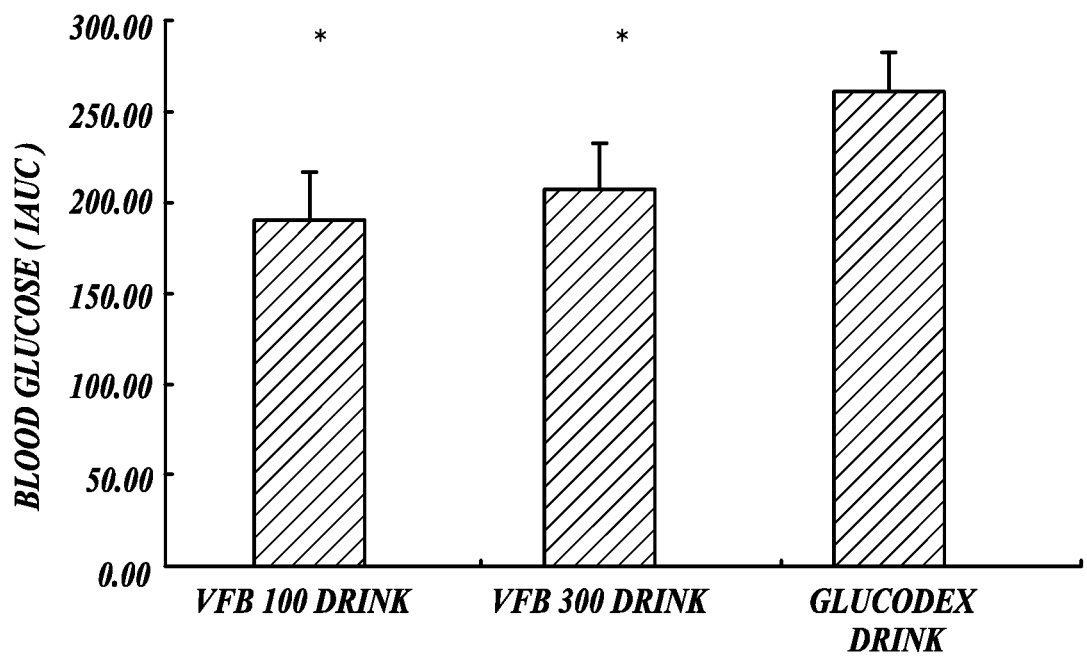
FIG. 11B graphically illustrates the incremental area under the curve (IAUC) in postprandial blood glucose after treatment of a plurality of subjects with the glucose drink treatments shown in FIG. 11A, as described in EXAMPLE 11.

FIG. 11B graphically illustrates the IAUC in postprandial blood glucose after treatment with the glucose control drink, glucose drink plus VFB100, or glucose drink plus VFB300. The "*" symbols in FIG. 11B represent a significant difference (p<0.05) in blood glucose levels between treatment and control. As shown in FIG. 11B, the IAUC in VFB100 treatment and in VFB300 treatment were significantly lower when compared to the control (p<0.05), but there was no significant difference observed between the IAUC in VFB100 drink treatment and the VFB300 drink treatment.

Summary and Conclusion:

In bread, both VFB100 and VFB300 were observed to lower plasma blood glucose. When compared to the bread control without VFB, a trend was observed wherein the larger VFB300 granules produced a greater effect on postprandial blood glucose than the finer VFB100 granules. While not wishing to be bound by theory, it is likely that the larger particles (VFB300) are less accessible to water molecules before the baking process of bread, and therefore more particles may be available for binding with water molecules after the consumption of bread, whereas the smaller particles (VFB100) are likely saturated with the binding of water molecules during the baking process and before consumption. Hence, a larger particle size (e.g., 300) of VFB displays a more viscous gelling and performs better than a smaller particle size (e.g., 100) of VFB in trapping glucose in the GI tract when consumed with white bread.

When mixed into drinks, both the VFB100 and VFB300 generated a greater postprandial glycemic response in comparison to the control than that observed in the breads, likely due to the direct absorption of glucose when drinks were consumed as compared to breads. However, the smaller particle size (VFB100) resulted in a greater reduction of blood glucose in drinks as compared to the larger size (VFB300). While not wishing to be bound by theory, it is likely that the faster absorption rate of glucose in drinks contributes to this result, since smaller particles are able to bind to water molecules more easily, which leads to better gel formation. This mechanism is likely different from that in bread because the VFB in drinks does not undergo any processing and can directly interact with water molecules and trap glucose.

Conclusion:

These results indicate that the administration of a smaller particle size of VFB (e.g., VFB100) in the drink form is best for healthy subjects to improve their glycemic response. The administration of a larger particle size of VFB (e.g., VFB300) in the solid food form (e.g., bread) is best for healthy subjects to improve their glycemic response.

Example 12

This example describes a dose response study to determine the glycemic index lowering potential of various doses of VFB added to liquid and solid food formulations before consumption.

Methods:

The glycemic index reducing potential of VFB100 and VFB300 was determined when added to liquid (glucose drinks) and solid (white bread plus margarine) food formulations. Three different doses were administered and the glycemic index was calculated for each dose. Healthy subjects underwent treatments of separate days, with each subject performing up to two tests per week with at least one day between tests. On each test day, subjects arrived to the test site in the morning after a 10- to 14-hour overnight fast. After being weighed and after a fasting sample was obtained by finger prick, the subject then consumed a test meal within 10 minutes and further blood samples were obtained at 15, 30, 45, 60, 90, and 120 minutes after the start of the test meal. Subjects were also given a choice of one to two cups of either water, tea, or coffee, with or without milk. The beverage consumed by each subject remained the same on each test day.

Glucose Series

Subjects

The glucose series was tested in ten healthy subjects including five males and five females, age 35.6±13.2 years; body mass index 24.6±2.1 kg/m2, as shown below in TABLE 32.

TABLE 32

Subject Details Glucose Series

| ID | Sex | Ethnicity | Age (yrs) | Height (cm) | Weight (kg) | BMI (kg/m2) |
|---|---|---|---|---|---|---|
| 247 | F | Caucasian | 56 | 167.0 | 70.0 | 25.1 |
| 249 | M | Caucasian | 61 | 182.0 | 79.1 | 23.9 |
| 174 | M | Caucasian | 29 | 185.2 | 92.0 | 26.8 |
| 124 | F | Caucasian | 29 | 162.5 | 54.0 | 20.4 |
| 161 | F | Caucasian | 40 | 157.0 | 56.7 | 23.0 |
| 208 | M | Caucasian | 34 | 175.0 | 79.0 | 25.8 |
| 126 | F | Caucasian | 20 | 157.4 | 62.5 | 25.2 |
| 253 | M | East Asian | 25 | 167.0 | 76.4 | 27.4 |
| 313 | M | Caucasian | 33 | 175.0 | 71.5 | 23.3 |
| 311 | F | Caucasian | 29 | 158.0 | 63.6 | 25.5 |
| | | Mean ± SD | 35 ± 10.3 | 168 ± 10.3 | 70.5 ± 11.6 | 24.6 ± 2.1 |

Test Meals (Glucose Series)

The test meals in the glucose series consisted of 50 g of glucose mixed with 200 ml of water to which the VFB was added using a small hand mixer. In addition to the test foods, each subject in the glucose series was also given a standard glucose control matched for carbohydrate content on three separate occasions.

TABLE 33

Nutrient Content of Glucose Series

| Test Meal | Abbrev | Amount (g) | Protein (g) | Fat (g) | Total CHO (g) | Dietary fiber (g) | Available CHO (g) |
|---|---|---|---|---|---|---|---|
| Glucose | Gluc | 50 | 0 | 0 | 50 | 0 | 50 |
| Glucose + 2.5 g VFB | VFB2.5 | 52.5 | 0 | 0 | 52.5 | 2.5 | 50 |
| Glucose + 5.0 g VFB | VFB5.0 | 55 | 0 | 0 | 55 | 5.0 | 50 |
| Glucose + 7.5 g VFB | VFB7.5 | 57.5 | 0 | 0 | 57.5 | 7.5 | 50 |

*weight may vary slightly between batches, depending on moisture content, CHO = carbohydrate.

White Bread Series

Subjects

The white bread series was tested in ten healthy subjects including three males and seven females, age 33.5±11.1 years, body mass index 26.3±5.2 kg/m2, as shown below in TABLE 34.

TABLE 34

Subject Details White Bread Series

| ID | Sex | Ethnicity | Age (yrs) | Height (cm) | Weight (kg) | BMI (kg/m2) |
|---|---|---|---|---|---|---|
| 141 | F | Caucasian | 26 | 144.0 | 50.0 | 24.11 |
| 12 | M | Caucasian | 42 | 174.0 | 80.0 | 26.40 |
| 308 | F | Caucasian | 21 | 158.0 | 50.0 | 20.03 |
| 303 | F | Caucasian | 19 | 167.0 | 89.8 | 32.20 |
| 316 | F | Caucasian | 36 | 163.0 | 69.7 | 26.20 |
| 290 | F | Caucasian | 20 | 159.0 | 50.8 | 20.09 |
| 207 | M | Caucasian | 50 | 168.0 | 76.1 | 26.96 |
| 199 | M | Caucasian | 41 | 179.0 | 116.0 | 36.20 |
| 210 | F | Caucasian | 41 | 153.0 | 67.3 | 28.75 |
| 93 | F | Caucasian | 39 | 162.0 | 58.0 | 22.10 |
| | | Mean ± SD | 33.5± 11.1 | 162.7 ± 10.1 | 70.8± 21.0 | 26.3 ± 5.2 |

Test Meals (White Bread Series)

The white bread series consisted of portions of white bread containing 50 g available carbohydrate (defined as total carbohydrate minus dietary fiber). The white bread was baked in a bread maker in loaves containing 250 g available carbohydrate. The ingredients for each loaf (250 ml warm water, 340 g all purpose flour, 7 g sugar, 4 g salt, and 6.5 g dry yeast) were placed into the bread maker according to instructions and the machine turned on. After the loaf had been made, it was allowed to cool for an hour, and then weighed and after discarding the crust ends, the remainder was divided into portion sizes containing 50 g available carbohydrate. These portions were frozen prior to use, and reheated in the microwave prior to consumption.

To avoid loss of VFB and increase palatability, 10 g of Becel margarine was added to the white breads that had VFB sprinkled on it. To control for any effect the margarine may have had on the glucose tolerance, an extra white bread with margarine only was also consumed. All test meals were given in random order. An extra test meal of white bread with margarine was also given in the white bread series to match the margarine given with the VFB.

TABLE 35

Nutrient Content of White Bread Series

| Test Meal | Abbrev | Amount (g) | Protein (g) | Fat (g) | Total CHO (g) | Dietary fiber (g) | Available CHO (g) |
|---|---|---|---|---|---|---|---|
| White Bread | WB | 104* | 7.6 | 1.6 | 52.8 | 2.8 | 50 |
| White Bread + Margarine | WB + M | 114 | 1.1 | 9.6 | 52.8 | 2.8 | 50 |
| White Bread + Margarine + VFB2.5 g | VFB2.5 | 114 | 1.1 | 9.6 | 55.3 | 5.3 | 50 |
| White Bread + Margarine + VFB5.0 g | VFB5.0 | 114 | 1.1 | 9.6 | 57.8 | 7.8 | 50 |
| White Bread + Margarine + VFB7.5 g | VFB7.5 | 114 | 1.1 | 9.6 | 60.3 | 10.3 | 50 |

*weight may vary slightly between batches, depending on moisture content, CHO = carbohydrate.

Assay Methods:

Blood glucose was measured after fasting and at 15, 30, 45, 60, 90, and 120 minutes after eating the test meal. Incremental areas under the blood glucose response curves (IAUC) were calculated using the trapezoid rule and ignoring area beneath the baseline. Each subject's IAUC after consumption of each test food was expressed as a percentage of the mean IAUC of the three white bread controls taken by the same subject.

The glycemic index was calculated by expressing each subject's glucose IAUC for the test food as a percentage of the same subject's average response after reference white bread. The mean of the resulting values was the food GI based on the glucose scale (i.e., GI of glucose=100). The blood glucose concentrations at each time and the IAUC values were subjected to repeated measures analysis of variance (ANOVA) examining for the effect of the test meal.

After demonstration of significant heterogeneity, the significance of the differences between individual means was assessed using Tukey's test to adjust for multiple comparisons. In addition, the significance of the differences between blood glucose concentrations and increments for each test food and white bread were assessed by paired t-test. To estimate the GI-lowering potential of 1 g of VFB, the GI change for each individual dose was averaged and calculated per gram of VFB.

Within-Subject Variation:

The incremental areas under the blood glucose response curves (IAUC) after the three tests of white bread control were calculated (data not shown). Although the difference in the IAUC between subjects was highly significant, there was no effect of order using the ANOVA statistical method. The mean within-subject coefficients of variation (CV) for IAUC for the glucose and white bread series were 21.7±4.9% and 26.5±5.2%, respectively, which is average for normal subjects. Values less than 30% were considered to be satisfactory in the study.

Palatability was rated on a 100 mm visual analogue scale anchored at very "unpalatable" at one end and "very palatable" at the other end. Therefore, a higher number corresponds to a subject's perception of a more palatable product.

Results

Blood Glucose Response for Glucose Test Meal

The results of the glucose test meal study are summarized below in TABLE 36. The "*" symbol indicates a statistically significant difference between the test condition and glucose control at the indicated time point.

TABLE 36

Summary of Blood Glucose Response for Glucose Test Meal

| Test Condition | 0 min (mean) | 15 min | 30 min | 45 min | 60 min | 90 min | 120 min | AUC |
|---|---|---|---|---|---|---|---|---|
| Glucose Control (50 g) | 4.36 ± 0.13 | 6.5 ± 0.22 | 7.86 ± 0.49 | 7.83 ± 0.64 | 6.87 ± 0.64 | 4.9 ± 0.45 | 3.76 ± 0.30 | 216.4 ± 28.4 |
| Glucose + VFB 2.5 g | 4.44 ± 0.15 | 5.72 ± 0.28* | 7.19 ± 0.45 | 7.27 ± 0.68 | 6.97 ± 0.71 | 5.32 ± 0.45 | 4.31 ± 0.38 | 190.1 ± 36.4 |
| Glucose + VFB 5.0 g | 4.35 ± 0.15 | 5.64 ± 0.26* | 6.75 ± 0.34* | 6.87 ± 0.48* | 6.28 ± 0.57 | 5.26 ± 0.42 | 4.57 ± 0.26 | 170.1 ± 29.6 |
| Glucose + VFB 7.5 g | 4.48 ± 0.15 | 5.67 ± 0.33* | 6.71 ± 0.27* | 6.66 ± 0.38* | 6.31 ± 0.44 | 5.37 ± 0.29 | 4.77 ± 0.26* | 156.7 ± 23.5 |

As shown above in TABLE 36, Glucose+VFB 2.5 g as compared to glucose control showed a statistically significant decrease in blood glucose level at the 15-minute time point (p=0.0001). Glucose+VFB 5.0 g as compared to glucose control showed a statistically significant decrease in blood glucose levels at 15 minutes (p=0.026), at 30 minutes (p=0.009), at 45 minutes (p=0.023), and at 120 minutes (p=0.014) after test meal consumption. Glucose+VFB 7.5 g as compared to glucose control showed a statistically significant decrease in blood glucose levels at 15 minutes (p=0.016), 30 minutes (p=0.010), 45 minutes (p=0.011), and at 120 minutes (p=0.003).

Blood Glucose Response for White Bread Test Meal

The results of the white bread test meal are summarized below in TABLE 37. The "*" symbol indicates a statistically significant difference between the test condition and glucose control at the indicated time point.

TABLE 37

Summary of Blood Glucose Response for White Bread Test Meal

| Test Conditions | 0 min (mean) | 15 min | 30 min | 45 min | 60 min | 90 min | 120 min | AUC |
|---|---|---|---|---|---|---|---|---|
| White Bread Control | 4.21 ± 0.07 | 4.79 ± 0.12 | 6.30 ± 0.16 | 6.67 ± 0.14 | 6.28 ± 0.22 | 5.54 ± 0.16 | 4.86 ± 0.13 | 174.2 ± 13.5 |
| White Bread + Margarine Control | 4.17 ± 0.08 | 4.81 ± 0.13 | 6.22 ± 0.17 | 6.45 ± 0.22 | 6.09 ± 0.35 | 5.37 ± 0.26 | 4.89 ± 0.20 | 164.7 ± 16.9 |
| White Bread + VFB2.5 g | 4.40 ± 0.07 | 4.66 ± 0.11 | 5.73 ± 0.21* | 5.75 ± 0.27* | 5.69 ± 0.34* | 5.54 ± 0.30 | 5.18 ± 0.23 | 121.1 ± 21.0 |
| White Bread + VFB5.0 g | 4.26 ± 0.12 | 4.34 ± 0.12* | 5.28 ± 0.17* | 5.66 ± 0.23* | 5.33 ± 0.24* | 5.13 ± 0.16 | 4.83 ± 0.15 | 96.6 ± 20.1 |
| White Bread + VFB7.5 g | 4.15 ± 0.12 | 4.4 ± 0.14* | 5.25 ± 0.17* | 5.35 ± 0.16* | 5.15 ± 0.14* | 4.71 ± 0.13* | 4.59 ± 0.12 | 85.1 ± 12.3 |

As shown above in TABLE 37, there was no significant difference observed in blood glucose concentrations after consumption of the white bread alone control as compared to the white bread plus margarine control. However, white bread plus margarine plus VFB 2.5 g as compared to white bread control showed a statistically significant difference at 30 minutes (p=0.008), 45 minutes (p=0.002), and 60 minutes (p=0.018) after consumption of the test meal. White bread plus margarine plus VFB 5.0 g as compared to white bread control showed a statistically significant difference at 15 minutes (p=0.006), 30 minutes (p=0.0001), 45 minutes (p=0.001), 60 minutes (p=0.001), and 90 minutes (p=0.0001). White bread plus margarine plus VFB 7.5 g as compared to white bread control showed a statistically significant difference at 15 minutes (p=0.029), 30 minutes (p=0.0001), 45 minutes (p=0.0001), 60 minutes (p=0.0001), and 90 minutes (p=0.001).

Palatability and Glycemic Index

The palatability scores and GI values for the glucose and bread series were calculated as described above and are shown below in TABLE 38. With regard to palatability, all test meals were well tolerated, however, the palatability scores of the glucose with VFB for all three doses was significantly lower when compared to the control glucose, likely because gelling of the glucose (after addition of VFB) took place before all was consumed.

TABLE 38

Glucose Drink Series: Palatability and Glycemic Index

| Test Meal | Abbrev | Palatability (mm) | Glycemic Index |
|---|---|---|---|
| Glucose | Gluc | 53.7 ± 6.4[a] | 100[a] |
| Glucose + 2.5 g VFB | VFB2.5 | 35.6 ± 10.4[b] | 83.7 ± 9.0[ab] |
| Glucose + 5.0 gVFB | VFB5.0 | 34.0 ± 9.6[b] | 77.7 ± 8.2[ab] |
| Glucose + 7.5 gVFB | VFB7.5 | 26.2 ± 8.8[b] | 71.5 ± 5.9[b] |

Values with different letters in the superscript are significantly different (p<0.001)

TABLE 39

White Bread Series: Palatability and Glycemic Index

| Test Meal | Abbrev | Palatability (mm) | Glycemic Index |
|---|---|---|---|
| White Bread | WB | 65.7 ± 7.8 | 71[a] |
| White Bread + Margarine | WB + M | 72.7 ± 8.2 | 66.8 ± 3.6[a] |
| White Bread + Margarine + VFB2.5 g | VFB2.5 | 75.6 ± 3.2 | 47.5 ± 5.9[b] |
| White Bread + Margarine + VFB5.0 g | VFB5.0 | 73.8 ± 5.7 | 37.3 ± 5.9[b] |
| White Bread + Margarine + VFB7.5 g | VFB7.5 | 64.9 ± 6.3 | 33.9 ± 3.6[b] |

With regard to glycemic index, in the glucose series the GI value of the 7.5 g VFB was significantly lower than the control glucose test meal (see TABLE 38), while in the bread series, all three doses of VFB (2.5, 5.0, 7.5 g) were significantly lower than both the white bread and the white bread and margarine control (see TABLE 39).

The glycemic index reducing potential of VFB was then determined when added to liquid (glucose) and solid (white bread plus margarine) food formulations. The glycemic index was calculated for each dose of VFB (2.5, 5.0, 7.5 g). Incremental areas under the blood glucose response curves (IAUC) were calculated as described above. Each subject's IAUC after consumption of each test food was expressed as a percentage of the mean IAUC of the three white bread controls taken by the same subject. The mean of the resulting values was the food GI based on the glucose scale (i.e., GI of glucose=100). In addition, the glycemic index lowering potential of each formulation was estimated. The glycemic index and change in glycemic index per gram of VFB (ΔGI/gVFB) are provided below in TABLE 40 for the glucose drink test meals, and are provided below in TABLE 41 for the white bread test meals.

TABLE 40

Average change in Glycemic Index when VFB is added to glucose drink

| Test Meal | GI | ΔGI/gVFB |
|---|---|---|
| 50 g Glucose Control | 100[a] | |
| 50 g Glucose + 2.5 g VFB | 83.7 ± 9.0[a,b] | −6.5 |
| 50 g Glucose + 5.0 g VFB | 77.7 ± 8.2[a,b] | −4.5 |
| 50 g Glucose + 7.5 g VFB | 72.5 ± 5.9[b] | −3.7 |
| | Average change in GI per gram of VFB | −4.9 ± 0.9 |

Numbers with different letters in the superscript are statistically different (p<0.05).

TABLE 41

Average Change in Glycemic Index When VFB is Added to White Bread

| Test Meal | GI | ΔGI/gVFB |
|---|---|---|
| White Bread Control | 71[a] | |
| White Bread + Margarine | 66.8 ± 3.6[a] | |
| White Bread + Margarine + 2.5 g VFB | 47.5 ± 5.9[b] | −9.4 |
| White Bread + Margarine + 5.0 g VFB | 37.3 ± 5.9[b] | −6.7 |
| White Bread + Margarine + 7.5 g VFB | 33.9 ± 3.6[b] | −5.0 |
| | Average change in GI per gram of VFB | −7.0 ± 1.3 |

Numbers with different letters in the superscript are statistically different (p<0.05).

Summary and Conclusions

Figure 12:
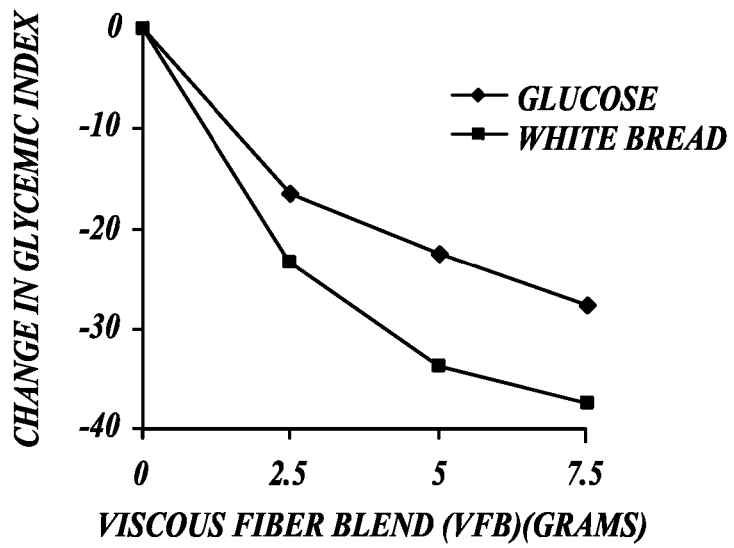
FIG. 12 graphically illustrates the change in glycemic index (GI) after consumption with a glucose drink or white bread containing increasing doses (2.5, 5.0, 7.5 g) of VFB, as described in EXAMPLE 12.

The results in this example demonstrate that the addition of VFB reduced the glycemic index of all of the meals, irrespective of the type of meal it was added to. FIG. 12 graphically illustrates the change in glycemic index after consumption with a glucose drink or white bread containing increasing doses of VFB. As shown in FIG. 12, increasing the dose of VFB causes a corresponding decrease in GI values, although the relationship is not linear.

To obtain an estimate of the GI lowering potential of VFB, the mean of the reduction observed per gram of VFB at each dose level was calculated and the results are shown above in TABLE 40 and TABLE 41. As shown in TABLE 40, the glycemic index lowering potential of VFB when added to a liquid meal (glucose drink) is −4.9±0.9 in the glucose series. As shown in TABLE 41, the glycemic index lowering potential of VFB when added to a solid meal (white bread plus margarine) is −7.0±1.3 in the white bread series. As there was no significant change in GI observed with the addition of margarine (see TABLE 37), the GI lowering potential for the white bread series was calculated using the control white bread GI value. Therefore, the addition of VFB to a liquid in the dose range of 2.5-7.5 g will result in a reduction of GI of the food product by approximately five GI units for a liquid food product, and seven GI units when added to a solid food product.

Example 13

This example demonstrates that the addition of VFB to various foods is effective to reduce the glycemic index of the food to which it was added.

Methods

Subjects

Ten healthy subjects (four male and six female), aged 37.3±3.6 years with a body mass index of 23.8±1.3 kg/m2 were studied. The individual details are shown below in TABLE 42.

TABLE 42

Subject Details

| ID | Sex | Ethnicity | Age (yrs) | Height (cm) | Weight (kg) | BMI (kg/m2) |
|---|---|---|---|---|---|---|
| 93 | F | Caucasian | 39 | 163.0 | 56.9 | 21.4 |
| 190 | F | Caucasian | 24 | 167.0 | 58.0 | 20.8 |
| 201 | M | Asian | 28 | 171.0 | 71.0 | 24.3 |
| 209 | M | Asian | 41 | 167.0 | 66.5 | 23.8 |
| 233 | F | Caucasian | 47 | 158.0 | 53.1 | 21.3 |
| 254 | F | Caucasian | 46 | 170.0 | 77.4 | 26.8 |
| 258 | F | Asian | 40 | 153.0 | 49.5 | 21.1 |
| 281 | M | Caucasian | 23 | 186.5 | 84.7 | 24.4 |
| 312 | F | Caucasian | 58 | 178.0 | 86.3 | 27.2 |
| 318 | M | Caucasian | 23 | 186.5 | 84.7 | 24.4 |
| | | Mean ± SD | 37.3 ± 3.6 | 169.8 ± 3.4 | 69.3 ± 4.7 | 23.8 ± 1.3 |

Test Meals

The following food types were included in this study:

Study 1: Corn flakes, Rice, Roast Turkey, Yogurt, White bread,

Study 2: Granola 1B, 1C, 2B, 3B, Slimfast

All test meals consisted of portions of each food containing 50 g available carbohydrate (defined as total carbohydrate minus dietary fiber). Five grams of VFB300 (granulated (konjac/xanthan/alginate (70:13:17)) was sprinkled onto the portion of cornflakes, rice, roast turkey dinner, or yogurt immediately prior to consumption. The cornflakes were consumed with 125 ml of milk.

To control for any effect the milk may have had on the glucose tolerance, an extra white bread with milk was also consumed. The white bread was baked in a bread maker in loaves containing 250 g available carbohydrate. The ingredients for each loaf (250 ml warm water, 340 g all purpose flour, 7 g sugar, 4 g salt, and 6.5 g dry yeast) were placed into the bread maker according to instructions and the machine turned on. After the loaf had been made, it was allowed to cool for an hour, and then weighed and after discarding the crust ends, the remainder was divided into portion sizes containing 50 g available carbohydrate. These portions were frozen prior to use and reheated in the microwave prior to consumption.

TABLE 43

Nutrient Content of Test Foods

| Test Meal | Abbrev | Amount (g) | Protein (g) | Fat (g) | Total CHO (g) | Dietary Fiber (g) | Available CHO (g) |
|---|---|---|---|---|---|---|---|
| White Bread | WB | 104* | 7.6 | 1.6 | 52.8 | 2.8 | 50 |
| White Bread + 125 ml 2% milk | WB + M | 104 + 125 ml | 8.1 | 4.1 | 58.8 | 2.8 | 56 |
| Cornflakes + 125 ml 2% milk | CF | 60 + 125 ml | 8.3 | 2.5 | 56 | 0 | 56 |
| Cornflakes + 125 ml milk + VFB (5 g) | CF + VFB | 60 + 125 ml + 5 g | 8.3 | 2.5 | 61 | 5 | 56 |
| Rice | Rice | 62.5 | 4.2 | 0 | 50.0 | 0 | 50 |
| Rice + VFB (5 g) | Rice + VFB | 62.5 + 5 | 4.2 | 0 | 55 | 5 | 50 |
| Turkey Dinner | Rturk | 422 | 21.6 | 11.3 | 55.4 | 5.6 | 50 |
| Turkey Dinner + VFB (5 g) | RT + VFB | 422 + 5 | 21.6 | 11.3 | 60.4 | 10.3 | 50 |
| yogurt | yogurt | 250 | 8 | 4 | 50 | 0 | 50 |
| yogurt + VFB (5 g) | Yog + VFB | 250 + 5 | 8 | 4 | 55 | 5 | 50 |

Assay Methods

Each subject underwent treatments on separate days, with each subject performing up to two tests per week with at least one day between tests. On each test day, subjects arrived in the morning after a 10- to 14-hour overnight fast. After being weighed and having a fasting blood sample obtained by finger prick, the subject then consumed a test meal within ten minutes and further blood samples were obtained at 15, 30, 45, 60, 90, and 120 minutes after the start of the test meal. Subjects were given a choice of one to two cups of water, tea, or coffee, with or without milk. The beverage consumed by each subject remained the same on each test day.

Blood samples were collected into 5 ml polypropylene tubes containing a small amount of sodium fluoride/potassium oxalate, mixed by rotating the tube vigorously, and placed into a refrigerator. After the last blood sample, tubes were stored at −20° C. prior to analysis of glucose using an automatic analyzer (Model 2300 STAT, Yellow Springs Instruments, Madison, Wis.). All blood samples were analyzed within one week of collection. Blood glucose was measured after fasting and at 15, 30, 45, 60, 90, and 120 minutes after eating the test meal. Incremental areas under the plasma glucose curves (IAUC) were calculated using the trapezoid rule and ignoring area beneath the baseline. The glycemic index was calculated by expressing each subject's glucose IAUC for the test food as a percentage of the same subject's average response after the reference white bread. The mean of the resulting values was the food glycemic index (GI) based on the glucose scale (i.e., GI of glucose=100). The blood glucose concentrations at each time point and the IAUC values were subjected to repeated measures analysis of variance (ANOVA) examining for the effect of the test meal. After demonstration of significant heterogeneity, the significance of the differences between individual means was assessed using Tukey's test to adjust for multiple comparisons. In addition, the significance of the differences between blood glucose concentrations and increments for each test food and white bread were assessed by paired t-test. The percent reduction in GI was calculated for each meal with VFB was also calculated.

Palatability was rated on a 100 mm visual analogue scale anchored at very "unpalatable" at one end and "very palatable" at the other end. The higher the number, the higher the perceived palatability of the test food.

Results

The results of the blood glucose tests for the various test foods are summarized below in TABLE 44. The "*" symbol indicates a statistically significant difference between the test condition and the white bread control at the indicated time point.

TABLE 44

Summary of Blood Glucose Responses for Test Foods

| Test Condition | 0 min (mean) | 15 min | 30 min | 45 min | 60 min | 90 min | 120 min | AUC |
|---|---|---|---|---|---|---|---|---|
| Cornflakes | 4.37 ± 0.13 | 5.14 ± 0.19 | 7.12 ± 0.30 | 7.64 ± 0.52 | 6.80 ± 0.55 | 5.13 ± 0.23 | 4.38 ± 0.27 | 184.9 ± 28.5 |
| Cornflakes + VFB | 4.41 ± 0.13 | 4.90 ± 0.25 | 6.33 ± 0.41 | 6.58 ± 0.40* | 6.15 ± 0.39 | 5.01 ± 0.23 | 4.72 ± 0.11 | 132.7 ± 23.5 |
| Rice | 4.41 ± 0.12 | 5.43 ± 0.23 | 7.23 ± 0.27 | 7.08 ± 0.44 | 6.38 ± 0.50 | 5.71 ± 0.26 | 4.63 ± 0.13 | 185.6 ± 31.7 |
| Rice + VFB | 4.44 ± 0.13 | 4.86 ± 0.13 | 5.84 ± 0.23* | 5.75 ± 0.29* | 5.44 ± 0.31* | 5.16 ± 0.11 | 4.86 ± 0.11 | 98.8 ± 17.1 |
| Roast Turkey | 4.39 ± 0.08 | 5.44 ± 0.21 | 7.34 ± 0.35* | 6.68 ± 0.54* | 5.64 ± 0.49* | 4.29 ± 0.08* | 4.04 ± 0.13* | 126.8 ± 22.5 |
| Roast Turkey + VFB | 4.43 ± 0.11 | 5.29 ± 0.25 | 6.51 ± 0.29 | 5.98 ± 0.36* | 5.06 ± 0.26* | 4.50 ± 0.10* | 4.41 ± 0.11 | 89.1 ± 12.0 |
| Yogurt | 4.43 ± 0.11 | 5.60 ± 0.26 | 6.92 ± 0.25 | 5.90 ± 0.36* | 4.72 ± 0.26* | 3.97 ± 0.09* | 3.85 ± 0.07 | 92.4 ± 11.8 |
| Yogurt + VFB | 4.41 ± 0.14 | 5.54 ± 0.31 | 6.52 ± 0.34 | 5.71 ± 0.42* | 4.82 ± 0.33* | 4.20 ± 0.13* | 4.08 ± 0.14* | 84.9 ± 14.5 |

TABLE 44-continued

Summary of Blood Glucose Responses for Test Foods

| Test Condition | 0 min (mean) | 15 min | 30 min | 45 min | 60 min | 90 min | 120 min | AUC |
|---|---|---|---|---|---|---|---|---|
| White Bread | 4.37 ± 0.12 | 5.12 ± 0.32 | 6.54 ± 0.40 | 6.73 ± 0.40 | 6.36 ± 0.37 | 5.26 ± 0.25 | 4.77 ± 0.12 | 158.9 ± 20.7 |

As shown above in TABLE 44, the blood glucose concentration after consumption of cornflakes was higher than the white bread control, with a statistical difference observed at 45 minutes (p=0.001). The blood glucose concentration after consumption with cornflakes plus VFB was reduced as compared to cornflakes alone and was very similar to that observed after consumption with the white bread control.

As shown in TABLE 44, the blood glucose concentration after consumption of rice was very similar to that observed after consumption of the white bread control. However, after consumption of rice plus VFB, the blood glucose concentration was reduced at statistically significant lower levels at 30 minutes (p=0.049), 45 minutes (p=0.005), and 60 minutes (p=0.002) after test meal consumption as compared to the white bread control.

As shown in TABLE 44, the blood glucose concentration after consumption of roast turkey was initially higher than that observed for the white bread control with a significantly higher level observed at 30 minutes (p=0.025) then trended lower, with a statistically significant lower level observed at 60 minutes (p=0.037), 90 minutes (p=0.001), and 120 minutes (0.011). After consumption of roast turkey with VFB, the initial blood glucose levels were similar to the white bread control, then trended lower than those observed for white bread, with a statistically significant lower level observed at 45 minutes (p=0.006), 60 minutes (p=0.001), and 90 minutes (p=0.012) as compared to the white bread control.

Finally, as further shown in TABLE 44, the blood glucose concentration after consumption of yogurt was initially higher than that observed for the white bread control, then trended lower with a statistically significant lower level observed at 45 minutes (p=0.021), at 60 minutes (p=0.00), and at 90 minutes (p=0.001) as compared to the white bread control. After consumption of yogurt with VFB, the blood glucose concentration was initially the same as the white bread control, then trended lower with a statistically significant lower level observed at 45 minutes (p=0.007), 60 minutes (p=0.00), 90 minutes (p=0.00), and 120 minutes (p=0.00) as compared to the white bread control.

Palatability and Glycemic Index

The palatability scores and glycemic values for the test meals are shown below in TABLE 45.

TABLE 45

Palatability and Glycemic Index

| Test Meal | Abbrev | Palatability (mm) | Glycemic Index (GI) | Glycemic Index Category[1] |
|---|---|---|---|---|
| Cornflakes + 125 ml 2% milk | CF | 66.5 ± 4.5 | 83.4 ± 8.0 | High |
| Cornflakes + 125 ml 2% milk + VFB | CF + VFB | 58.8 ± 5.2 | 58.0 ± 6.9 | Medium |
| Rice | Rice | 42.0 ± 4.4 | 82.0 ± 7.5 | High |
| Rice + VFB | Rice + VFB | 41.4 ± 6.5 | 44.7 ± 4.4 | Low |
| Roast Turkey | RT | 78.1 ± 5.5 | 55.2 ± 4.7 | Low |
| Roast Turkey + VFB | RT + VFB | 75.5 ± 6.4 | 41.1 ± 3.5 | Low |
| Yogurt | Yog | 75.1 ± 8.3 | 44.2 ± 4.1 | Low |
| Yogurt + VFB | Yog + VFB | 77.0 ± 5.5 | 37.5 ± 2.9 | Low |
| White Bread | WB | 71.3 ± 5.0 | 71.0 ± 0.0 | High |
| White Bread + 125 ml 2% milk | WB + M | 67.2 ± 4.6 | 83.7 ± 9.0 | High |

[1]The Glycemic Index Category is defined as follows: GI ≤ 55 is categorized as "Low"; 56 < GI < 69 is categorized as "Medium"; GI ≥ 70 is categorized as "High" (See the Canadian Diabetes Association website, www.diabetes.ca/SectionAbout glycemic.asp, accessed Jul. 26, 2007).

As shown above in TABLE 45, the addition of VFB reduced the glycemic index (GI) of all of the test meals irrespective of the type of meal to which it was added. In particular, it is noted that the addition of VFB to cornflakes reduced the GI of the cornflakes from the high GI category to the medium category, and the addition of VFB to rice reduced the GI of the rice from the high GI category to the low GI category.

Figure 13:
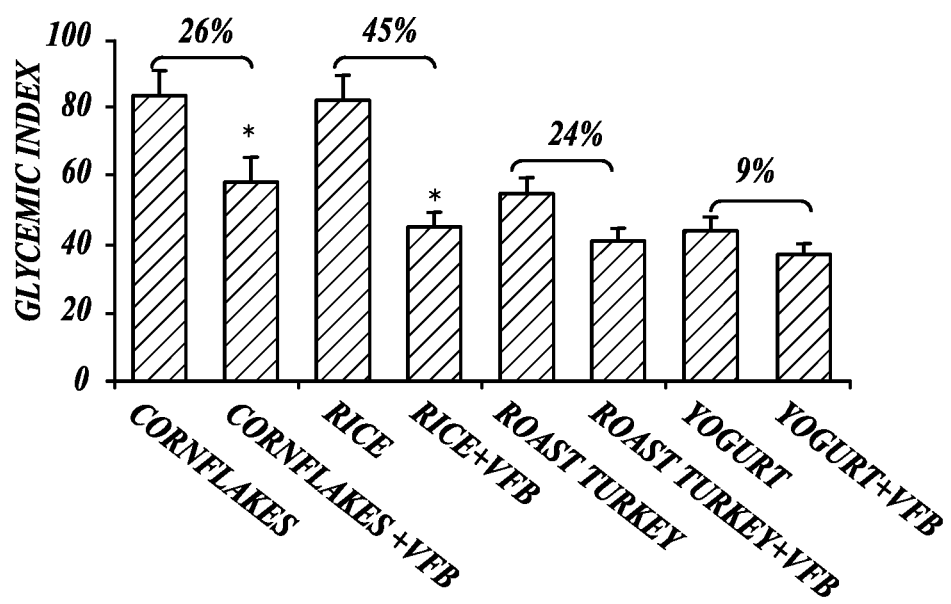
FIG. 13 graphically illustrates the glycemic index for each test meal with or without 5.0 g of VFB per approximately 50 g available carbohydrates, expressed as the Mean±SEM.

FIG. 13 graphically illustrates the glycemic index for each test meal with or without 5.0 g of VFB per approximately 50 g available carbohydrates, expressed as the Mean±SEM. As shown in FIG. 13, addition of VFB to cornflakes, rice, turkey dinner or yogurt resulted in a 26%, 45%, 24%, and 9% reduction in meal GI, respectively. The percent reductions observed in the GI for cornflakes and rice meals when adding VFB were statistically significant (p<0.00001).

With regard to palatability, all test meals were well tolerated. It is noted that the addition of VFB to the various food types did not significantly reduce the palatability of the particular food product. Therefore, these results demonstrate that the addition of VFB reduced the GI of all of the test meals irrespective of the type of meal to which it was added and did not significantly affect the palatability of the test meals.

Example 14

This example demonstrates that the addition of VFB to various types of granola is effective to reduce the glycemic index of the granola to which it was added.

Methods

Subjects

Ten healthy subjects (four male and six female), aged 37.3±3.6 years with a body mass index of 23.8±1.3 kg/m2 were studied. The individual details of the subjects that participated in this study are described in TABLE 42 of EXAMPLE 13.

Test Meals

All test meals consisted of portions of each food containing 50 g available carbohydrate (defined as total carbohydrate minus dietary fiber). The white bread control was generated as described in EXAMPLE 13. VFB may be incorporated into granola by blending selective dry and liquid granola ingredients with VFB (konjac/xanthan/alginate (70:13:17)) and then processing the overall mixture through baking or other drying methods. The following test granola meals were prepared by baking the VFB into the granola:

Granola 1C=Cranberry Granola with 2.5 g VFB per 60 g serving (50 g available CHO)

Granola 1B=Blueberry Granola with 2.5 g VFB per 60 g serving (50 g available CHO)

Granola 2B=Blueberry Granola with 5.0 g VFB per 60 g serving (50 g available CHO)

Granola 3B=Blueberry Granola control (no VFB) 60 g serving (50 g available CHO)

TABLE 46

Nutrient Content of Test Foods

| Test Meal | Abbrev | Amount (g) | Protein (g) | Fat (g) | Total CHO (g) | Dietary Fiber (g) | Available CHO (g) |
|---|---|---|---|---|---|---|---|
| Blueberry Granola (control) | Gran3B | 92 | 9.3 | 14.6 | 62.3 | 12.3 | 50 |
| Cranberry Granola + 2.5 g VFB | Gran1C | 93 | 10.3 | 14.7 | 61.9 | 11.8 | 50 |
| Blueberry Granola + 2.5 g VFB | Gran1B | 92 | 10.0 | 14.3 | 61.4 | 11.4 | 50 |
| Blueberry Granola + 5 g VFB | Gran2B | 98 | 10.4 | 15.2 | 65.8 | 15.8 | 50 |
| Slimfast | Slimfast | 470 ml | | | | | 50 |
| White Bread | WB | 104* | 7.6 | 1.6 | 52.8 | 2.8 | 50 |

Assay Methods

Each subject underwent treatments on separate days, with each subject performing up to two tests per week with at least one day between tests. On each test day, subjects arrived in the morning after a 10- to 14-hour overnight fast. After being weighed and having a fasting blood sample obtained by finger prick, the subject then consumed a test meal within ten minutes and further blood samples were obtained at 15, 30, 45, 60, 90, and 120 minutes after the start of the test meal. Subjects were given a choice of one to two cups of water, tea, or coffee, with or without milk. The beverage consumed by each subject remained the same on each test day.

Blood glucose was measured after fasting and at 15, 30, 45, 60, 90, and 120 minutes after eating the test meal using the methods described in EXAMPLE 13. Palatability was measured using the methods described in EXAMPLE 13.

Results

The results of the blood glucose tests for the various granola test meals and controls are summarized below in TABLE 47. The "*" symbol indicates a statistically significant difference between the test condition and the white bread control at the indicated time point.

TABLE 47

Summary of Blood Glucose Responses for Test Foods

| Test Conditions | 0 min (mean) | 15 min | 30 min | 45 min | 60 min | 90 min | 120 min | AUC |
|---|---|---|---|---|---|---|---|---|
| Gran1B | 4.49 ± 0.14 | 4.96 ± 0.24 | 6.16 ± 0.29 | 5.61 ± 0.25* | 4.86 ± 0.27* | 4.77 ± 0.15 | 4.68 ± 0.09 | 73.1 ± 16.2 |
| Gran1C | 4.38 ± 0.13 | 4.79 ± 0.21 | 5.85 ± 0.33* | 5.81 ± 0.33* | 5.36 ± 0.30* | 4.69 ± 0.17* | 4.51 ± 0.14 | 86.6 ± 15.3 |
| Gran2B | 4.49 ± 0.14 | 4.82 ± 0.15 | 5.47 ± 0.20* | 5.26 ± 0.21* | 4.86 ± 0.22* | 4.68 ± 0.17* | 4.56 ± 0.11 | 50.3 ± 10.1 |
| Gran3B | 4.44 ± 0.12 | 5.36 ± 0.22 | 6.93 ± 0.33* | 6.76 ± 0.53 | 6.40 ± 0.51 | 4.88 ± 0.27 | 4.28 ± 0.13 | 147.7 ± 25.7 |
| Slimfast | 4.45 ± 0.12 | 5.40 ± 0.21 | 6.09 ± 0.34 | 5.11 ± 0.27 | 4.41 ± 0.24 | 4.22 ± 0.16 | 4.12 ± 0.15 | 59.8 ± 8.8 |
| WB | 4.37 ± 0.12 | 5.12 ± 0.32 | 6.54 ± 0.40 | 6.73 ± 0.40 | 6.36 ± 0.37 | 5.26 ± 0.25 | 4.77 ± 0.12 | 158.9 ± 20.7 |

As shown above in TABLE 47, the blood glucose concentration after consumption of granola 3B (control) was similar to the glucose concentration after consumption of white bread, with a statistically significant decrease observed at 30 minutes (p=0.034) after test meal consumption. The blood glucose concentration after consumption of granola 1B (with 2.5 g VFB) was significantly lower than that observed for the white bread control, with a statistically significant difference observed at 45 minutes (p=0.001) and 60 minutes (p=0.0001) after test meal consumption. The blood glucose concentration after consumption of granola 2B (with 5.0 g VFB) was further reduced as compared to the white bread control, with a statistically significant reduction observed at 30 minutes (p=0.002), 45 minutes (p=0.0001), 60 minutes (p=0.0001), and 90 minutes (p=0.036) after test meal consumption. The blood glucose concentration after consumption of granola 1C (with 2.5 g VFB) was also significantly lower than that observed for the white bread control, with a statistically significant reduction observed at 30 minutes (p=0.034), 45 minutes (0.001), 60 minutes (0.001), and 90 minutes (0.022) after test meal consumption.

Palatability and Glycemic Index

The palatability and glycemic index was analyzed as described above in EXAMPLE 13. The results are shown below in TABLE 48. With regard to palatability, all test meals were well tolerated; however the palatability score of the blueberry granola with 5 g VFB (Gran2B) was significantly lower when compared to the white bread control.

TABLE 48

Palatability and glycemic Index

| Test Meal | Abbrev | Palatability | Glycemic Index | GI Category1 |
|---|---|---|---|---|
| White Bread | WB | 71.3 ± 5.0 | 71.0 ± 0.0 | High |
| Blueberry Granola (control) | Gran3B | 52.7 ± 8.7 | 63.8 ± 6.3 | Medium |
| Blueberry Granola + 2.5 g VFB | Gran1B | 45.2 ± 8.1 | 32.6 ± 4.8 | Low |

TABLE 48-continued

Palatability and glycemic Index

| Test Meal | Abbrev | Palat-ability | Glycemic Index | GI Category1 |
|---|---|---|---|---|
| Cranberry Granola + 2.5 g VFB | Gran1C | 45.2 ± 8.9 | 38.4 ± 4.0 | Low |
| Blueberry Granola + 5 g VFB | Gran2B | 40.8 ± 8.6 | 21.6 ± 3.0 | Low |
| Slimfast | Slimfast | 43.0 ± 8.6 | 30.4 ± 5.4 | Low |

Figure 14:
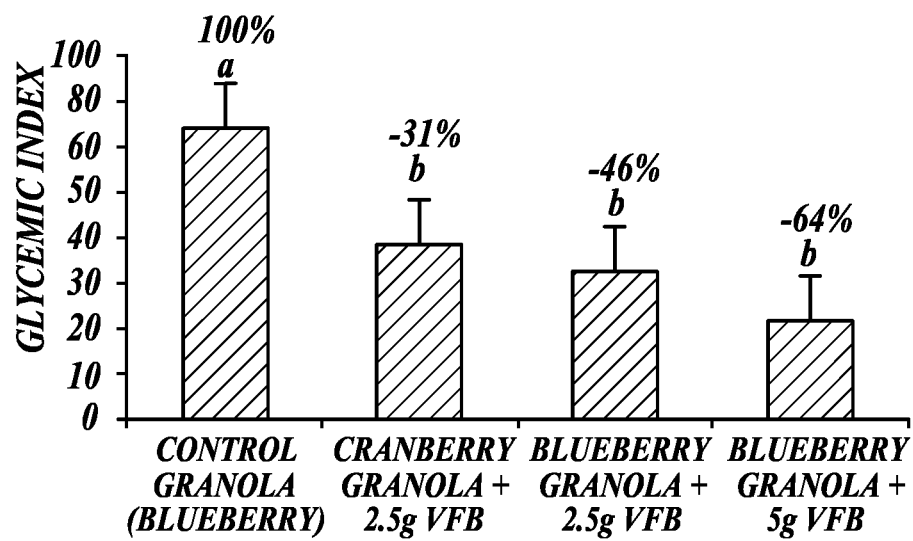
FIG. 14 graphically illustrates the glycemic index for each test meal with or without VFB, expressed as the Mean±SEM.

With regard to the Glycemic Index, all of the granolas containing VFB were significantly lower that the white bread control or the granola control. FIG. 14 graphically illustrates the glycemic index for each test meal with or without VFB, expressed as the Mean±SEM. As shown in FIG. 14, addition of VFB reduced the glycemic index of all the granolas, with statistically significant reductions observed irrespective of the type of granola used ($p<0.0001$). As compared to the control granola (blueberry), the cranberry granola (2.5 g VFB), blueberry granola (2.5 g VFB) and blueberry granola (5.0 g VFB) reduced the GI by 31%, 45%, and 64%, respectively.

This study demonstrates that VFB can be incorporated into granola and other foods as an effective and palatable method to moderate the spike in blood glucose levels after ingesting foods with medium or high glycemic indices. Not only did the addition of VFB reduce the GI in a dose-dependent fashion, it also lowered the glycemic index category of the granola from medium to low. The addition of VFB to other medium or high glycemic index category foods can be expected to have similar effects.

Example 15

This Example describes a 14-week study with overweight and obese human subjects demonstrating that Viscous Fiber Blend (VFB) is effective to reduce weight, lower cholesterol levels, and decrease fasting glucose when administered daily.

Rationale:

The purpose of this observational retrospective clinical analysis was to examine the efficacy of VFB micro-granules (VFB100) (granulated konjac/xanthan/alginate (70:13:17)) on weight loss, body mass index, waist circumference, waist-hip ratio, plus laboratory measurements including total and LDL cholesterol, triglycerides, fasting insulin, fasting glucose and 2 hour glucose tolerance test for 14 weeks in overweight and obese adults.

Subjects:

A total of 29 sedentary adults (23 women; 6 men in generally good health), aged 20 to 65 years with a body mass index (BMI) range of approximately 23 $kg/m^2$ to 36 $kg/m^2$ were invited to participate through a series of advertisements placed in local newspapers. Subjects gave their written consent for participation in the program and were required to attend group lectures on general health, diet, and exercise, every two weeks given by one of the study directors for a maximum of 14 weeks.

Methods:

Screening and evaluation of the subjects were performed by a medical doctor or naturopathic physician for height (inches), weight (pounds), and waist-hip measurements on a bi-weekly basis. Percent body fat was determined using bio-electrical impedance testing at baseline and every two weeks thereafter. A computerized analysis (RJR Systems) was further employed on all subjects in order to determine BMI and percent body fat. While all subjects enrolled in the program were initially evaluated for HDL, LDL, total cholesterol, triglycerides, fasting glucose, fasting insulin, 2 hour fasting insulin, and 75 gram glucose tolerance test at baseline, only those with aberrant risk factors were re-tested using the latter laboratory parameters at week 14. During this time frame, volunteers were required to take up to 10 grams of VFB micro-granules (VFB100) with 12 to 16 oz of water in divided doses throughout the day.

Significance was determined using the paired T-test analysis with assistance from the Short Term Consulting Service, Department of Statistics, University of British Columbia.

Results:

Weight Loss and Other Parameters:

During the 14 weeks of VFB use, there were significant reductions in group weight (−12.78±7.84 pounds), waist measurements (−4.75±2.19 inches), % body fat (−2.43±2.39%), and BMI (−2.26±1.24 $kg/m^2$). Similarly and in concert with these latter outcomes, both sexes individually demonstrated significant reductions in the tested weight loss variables as noted in the following tables:

TABLE 49

Group 1: Men and Women Combined

| Test | Sample size | Week 0 mean | SD | Week 14 mean | SD | Change | SD | % Change |
|---|---|---|---|---|---|---|---|---|
| *Weight | 29 | 198.38" | ±31.82 | 185.6 | ±30.52 | −12.78 | ±7.84 | −6.44 |
| *Waist | 29 | 40.78"" | ±5.03 | 36.03 | ±5.10 | −4.75 | ±2.19 | −11.65 |
| *Hip | 29 | 45.79"" | ±3.02 | 42.06 | ±2.93 | −3.73 | ±1.62 | −8.14 |
| *% fat | 29 | 40.30 | ±8.28 | 37.87 | ±8.88 | −2.43 | ±2.39 | −6.02 |

*$p < 0.05$ from week 0
"weight is in pounds
""waist and hip is in inches

TABLE 50

Group 1: Men (n = 6)

| Test | Week 0 mean | SD | Week 14 mean | SD | Change | SD | % Change |
|---|---|---|---|---|---|---|---|
| *Weight | 246.50 | ±20.10 | 228.20 | ±28.78 | −18.32 | ±6.15 | −7.43 |
| *Waist | 47.69 | ±3.80 | 41.98 | ±4.05 | −5.71 | ±1.81 | −12.00 |

TABLE 50-continued

| | Group 1: Men (n = 6) | | | | | | |
|---|---|---|---|---|---|---|---|
| Test | Week 0 mean | SD | Week 14 mean | SD | Change | SD | % Change |
| *Hip | 47.47 | ±3.00 | 43.45 | ±2.91 | −4.02 | ±1.43 | −8.00 |
| *% Fat | 26.58 | ±3.01 | 24.62 | ±2.97 | −1.97 | ±1.15 | −7.00 |

*p < 0.05 from week 0

TABLE 51

| | Group 2: Women (n = 23) | | | | | | |
|---|---|---|---|---|---|---|---|
| Test | Week 0 mean | SD | Week 14 mean | SD | Change | SD | % Change |
| *Weight | 185.83 | ±17.31 | 174.49 | ±19.33 | −11.34 | ±7.69 | −6.00 |
| *Waist | 38.97 | ±3.54 | 34.47 | ±4.16 | −4.50 | ±2.25 | −12.00 |
| *Hip | 45.35 | ±2.65 | 41.70 | ±2.89 | −3.65 | ±1.69 | −8.00 |
| *% Fat | 43.88 | ±4.52 | 41.33 | ±6.15 | −2.55 | ±2.63 | −6.00 |

*p < 0.05 from week 0

TABLE 52

| | BMI for all the Groups Combined | | | | | | |
|---|---|---|---|---|---|---|---|
| Gender | Sample size | Week 0 mean | SD | Week 14 mean | SD | Change | SD | % Change |
| *Male | 6 | 35.03" | ±4.09 | 32.47 | ±3.78 | −2.56 | ±1.22 | −7.31 |
| *Female | 23 | 33.45" | ±7.57 | 31.27 | ±8.17 | −2.18 | ±1.26 | −6.52 |
| *All | 29 | 33.78" | ±6.96 | 31.52 | ±7.43 | −2.26 | ±1.24 | −6.70 |

*p < 0.05 from week 0
"BMI in kg/m$^2$

Lipid Levels:

Compared to baseline values, those subjects employing VFB micro-granules for the 14-week study period had a significant reduction of 19.26% (n=17; p<0.05) and 25.51% (n=16; p<0.05) in total and LDL cholesterol values respectively. Although there was a trend towards a reduction in triglyceride and an increase in HDL cholesterol values, the resulting changes were not statistically significant.

Fasting Insulin and Glucose:

As a group and by the end of the study period, those participants employing VFB experienced a 6.96% reduction in fasting glucose (n=20; p<0.05), a 12.05% decline in 2 hour glucose tolerance (n=21; p<0.05), and 27.26% (n=17; p<0.05) reduction in fasting insulin levels compared to baseline (see graph 2). Although there was a trend towards a reduction in 2 hour fasting insulin levels, the results were not statistically significant.

TABLE 53 is a summary of the overall laboratory data obtained during the 14-week trial with VFB micro-granules:

TABLE 53

| | Laboratory Data Analysis Group Results: | | | | | | |
|---|---|---|---|---|---|---|---|
| Test | Sample size | Week 0 mean | SD | Week 14 mean | SD | Change | SD | % Change |
| *Total cholesterol (mmol/L) | 17 | 5.69 | ±1.07 | 4.60 | ±0.82 | −1.09 | ±0.63 | −19.26 |
| Triglycerides (mmol/L) | 17 | 1.92 | ±0.98 | 1.52 | ±0.56 | −0.40 | ±0.89 | −20.97 |
| HDL (mmol/L) | 17 | 1.48 | ±0.53 | 1.53 | ±0.77 | 0.05 | ±0.67 | 3.33 |
| *LDL (mmol/L) | 16 | 3.40 | ±0.96 | 2.53 | ±0.64 | −0.87 | ±0.56 | −25.51 |
| *Fasting glucose (mmol/L) | 20 | 5.75 | ±0.78 | 5.34 | ±0.49 | −0.40 | ±0.65 | −6.96 |
| *2 hr Glucose (mmol/L) | 21 | 6.09 | ±2.10 | 5.35 | ±1.81 | −0.73 | ±1.43 | −12.05 |
| *Insulin Fasting (pmol/L) | 17 | 89.41 | ±44.84 | 65.04 | ±33.21 | −24.37 | ±36.29 | −27.26 |
| 2 hr Insulin (pmol/L) | 17 | 433.53 | ±270.32 | 355.76 | ±332.44 | −77.76 | ±196.51 | −17.94 |

*p < 0.05 from baseline

Analysis of Efficacy Using Self-Reporting Scales:

In a self-reporting scale completed by the participants at the end of the study, 97.7% of the VFB users noted that they had a positive response to the product both in curbing food cravings and hunger.

Side Effects of the Test Preparation:

VFB was generally well tolerated by the participants with gastrointestinal (GI) symptoms comprising the majority of all the reported complaints. Symptoms such as gas, bloating, bowel cramping, constipation, and diarrhea were noted by the volunteers. Sixty-eight percent noted that their GI symptoms resolved within approximately 3 weeks of beginning VFB. A full 32% of the participants found that they had mild GI side effects throughout the study but that these were not sufficient in severity for them to discontinue use.

Discussion:

The results of this retrospective analysis clearly demonstrate that the use of VFB micro-granules (VFB100) along with general changes in diet and physical activity, over a 14-week time period, is of benefit in modifying the metabolic and cardiovascular risk factors in those who are overweight and/or obese. Overall, there was a significant reduction in group weight (−12.78±7.84 pounds), waist measurements (−4.75±2.19 inches) and percent body fat (−2.43%±2.39%). Moreover, these latter changes were paralleled by a significant decrease in fasting LDL (−25.51%), fasting glucose (−6.96%), and fasting insulin (−27.26%) levels over a relatively short time span of 14 weeks. This wide range of clinical benefits provided by VFB micro-granules is reflective of its unique physiological advantages in improving metabolic control.

Consuming 5 to 10 grams of foods rich in viscous soluble fiber has been reported to decrease serum LDL cholesterol and subsequent CVD events by 10% to 15% (Shamliyan, et al., *J. Fam. Pract.* 55:761-9 (2006)). Based on the results obtained from this study, VFB has been shown to be more effective in reducing LDL cholesterol by 25.1%. In comparison, research has shown that those who employ a "portfolio" of cholesterol-lowering foodstuffs for a minimum of 3 months have a stable reduction in LDL cholesterol by approximately 14% (p<0.001) (Jenkins, et al., *Am. J. Clin. Nutr.* 83:582-91 (2006)).

Moreover, the reduction in LDL cholesterol values seen in the current investigation is noteworthy as the percent decrease obtained with VFB falls within the range of effectiveness (20% to 55%) reported for statin-type medication (Ritishauser, *Swiss Med. Wkly* 136:41-9 (2006)).

The results of this study demonstrate that VFB is effective in promoting short-term weight loss over a 14-week time period. The results obtained (−12.78 pounds; 5.81 kg) are similar to those who have taken the anti-obesity medication orlistat. In a controlled study, overweight (BMI>25 kg/m$^2$) Type 2 diabetic patients who employed the drug orlistat at a dose of 120 mg tid over a 12-week time period lost 2.5 kg compared to 0.4 kg in the placebo group (p<0.05) (Kuo, et al., *Int. J. Clin. Pract.* 60(8):906-10 (2006)). Extended use (12 months) of prescription weight loss medications including sibutramine and orlistat has resulted in a mean weight loss of 4.5 kg and 2.9 kg, respectively, compared to a placebo (Dixon, *Australian Fam. Phys.* 35:576-79 (2006)).

It is interesting to note that in the current 14-week investigation, men lost more weight on average (−18.32±6.15 pounds) than the women (−11.34±7.69 pounds). This change could be ascribed to the basic sex differences seen in resting energy expenditure. A study by Dr. Robert Ferraro and his associates has shown that the sedentary 24-hour energy expenditure is approximately 5% to 10% lower in women compared to men after statistical adjustments for age, activity, and body composition (Ferraro, et al., *J. Clin. Invest.* 90:780-784 (1992)).

In this study, through the use of a portable indirect calorimeter (MedGem device by HealtheTech), it was determined that women had a lower average resting/basal metabolic rate (1841.18 kilocalories) score compared to men (2346.67 calories) at the outset of the study.

This study also demonstrated that in tandem with the reduction in weight, BMI scores were also lowered in significant fashion by 2.26±1.24% from baseline (p<0.05) in subjects that consumed VFB. BMI is a commonly employed measure to assess the degree of overweight/obesity and its overall impact on health risk (usda.gov/cnpp/Insights/Insight16b.pdf). For example, both genders with a BMI of greater than or equal to 30 have a higher mortality risk than those who are classified as being overweight (BMI from 25 kg/m$^2$ to 29.9 kg/m$^2$) (Villareal, et al. *Am. J. Clin. Nutr.* 82:923-34 (2005)).

In addition to modifying weight and cholesterol levels, the results of this study show that VFB significantly decreased fasting glucose, 2-hour glucose and fasting insulin levels, demonstrating that VFB is of great value in improving glycemic control. In particular, the results of the current study show that overall fasting insulin levels decreased from 89.41±44.84 pmol/L to 65.04±33.21 pmol/L during the 14-week investigation. This latter finding confirms that in those individuals who are overweight or obese, baseline and 4 hours postprandial rates of insulin secretion are higher than those with normal weight. This result is consistent with another study that measured 24-hour profiles of insulin secretion in normal and obese subjects (Polansky, et al., *J. Clin. Investig.* 28(suppl 2):3-6 (1998)).

Moreover, these results also suggests that lifestyle modifications along with VFB granules would be helpful in treating insulin resistance. Obesity plays a key role in insulin resistance, and an increase or decrease in insulin resistance is linked to weight gain or loss, respectively (Lamounier-Zepter, et al., *Best Pract. Res. Clin. Endocrin. Metabol.* 20:355-367 (2006)).

These latter outcomes together suggest that the therapeutic use of VFB is of practical benefit to those suffering with excess weight, obesity and/or metabolic syndrome.

Example 16

This Example describes a study with obese non-diabetic and diabetic human subjects exhibiting glycemic volatility demonstrating that the administration of Viscous Fiber Blend (VFB) to these subjects is effective to reduce their glycemic volatility.

Rationale:

12 non-diabetic obese subjects and several diabetic subjects were studied using a continuous glucose monitoring system (MiniMed® CGMS, Medtronic Inc.) and compared to normal weight control subjects. The CGMS is a portable electronic device worn for up to one week that is connected to a microelectronic sensor inserted by a physician into the abdominal adipose tissue. This device is FDA approved for monitoring blood sugar in insulin-dependent diabetics and it is typically used in diabetes specialty centers to obtain a more accurate and around-the-clock look at the diabetic's blood sugar to allow for more precise adjustments of their insulin. Rather than sampling blood sugar a few times per day, as with finger stick glucose monitors, the CGMS samples blood sugar several hundred times per day. After several days, the patient returns to the physician and the blood sugar data is downloaded into the physician's computer. The data can then be displayed graphically and can be quantitatively analyzed to assess such parameters as frequency of hypoglycemic episodes, as well as mean and peak blood sugar values. To our knowledge, as well as the knowledge of the device manufacturer, we are the first group to use the CGMS in the assessment of non-diabetic, obese individuals. We refer to the collective of increased frequency of blood sugar excursions, the rapid nature of the rise and fall of blood sugar, and the amount of time spent above an ideal blood sugar level as increased glycemic volatility.

Methods:

The glycemic volatility for the 12 obese non-diabetic subjects and several diabetic subjects was assessed at baseline and again after the five-week study using a continuous glucose monitoring system (CGMS MiniMed, Medtronic, Inc.). During the five-week study, each subject consumed from 10-15 g of VFB (konjac/xanthan/alginate (70:13:17)) per day. Subjects were also evaluated for subjective hunger and food cravings during the study period.

In a second study, several obese non-diabetic subjects were treated with a low glycemic index diet (without VFB) for a period of six months, and the glycemic volatility was assessed at baseline before the low glycemic index diet, and again after the six month diet.

In a third study, several diabetic subjects undergoing insulin treatment were treated with 10-15 g of VFB (konjac/xanthan/alginate (70:13:17)) per day for four weeks. The subjects were assessed at baseline and again after the four week study using a continuous glucose monitoring system (CGMS MiniMed, Medtronic, Inc.).

Results:

Normal Subjects:

FIG. 15 shows a representative continuous glucose monitoring system (CGMS) graph measuring normal glycemic volatility in a non-obese, non-diabetic subject over a 24-hour period. As shown in FIG. 15, the blood glucose levels of the normal subject are between the ideal value of 70 to 120 mmol/dL, and the glycemic volatility shows very modest and infrequent excursions from the average blood glucose level of approximately 100 mmol/dl over the 24-hour period, resulting in a fairly flat overall glycemic volatility. The data shown in FIG. 15 is representative of several normal subjects tested.

Obese, Non-Diabetic Subjects (before and after VFB Treatment):

In contrast to the results obtained in the normal subject, it was discovered that obese individuals had rapidly fluctuating blood sugar levels and typically exhibited highly frequent hyperglycemic and hypoglycemic blood sugar excursions as compared to age matched controls, as described in more detail below.

FIG. 16A shows a CGMS graph for an obese, non-diabetic subject (ID:10) measured over a 24-hour period prior to treatment with VFB (baseline). The results shown in FIG. 16A are representative of the results measured over 5 consecutive 24-hour time periods in this subject prior to treatment with VFB. As shown in FIG. 16A, the subject (ID: 10) had increased glycemic volatility in comparison to the normal subject (FIG. 15), with peak blood glucose levels exceeding 180 mg/dL, along with frequent blood glucose excursions, resulting in an overall increased glycemic volatility as compared to a normal individual (see FIG. 15). FIG. 16B shows a CGMS graph for the same subject ID:10 shown in FIG. 16A after 5 weeks of consumption of VFB (10-15 g/day). As shown in FIG. 16B, a dramatic decrease in glycemic volatility was observed in the subject ID:10 after treatment with VFB, with an average blood glucose level of approximately 100 mmol/dL maintained over the 24-hour period, similar to that observed in the normal subject (FIG. 15).

FIG. 17A shows a CGMS graph for a second obese, non-diabetic subject (ID:90) measured over a 24-hour period prior to treatment with VFB (baseline). The results shown in FIG. 17A are representative of the results measured over 5 consecutive 24-hour time periods in this subject prior to treatment with VFB. As shown in FIG. 17A, the subject (ID:90) had increased glycemic volatility in comparison to the normal subject (FIG. 15), with frequent blood glucose excursions, resulting in an overall increased glycemic volatility as compared to a normal individual (see FIG. 15). FIG. 17B shows a CGMS graph for the same subject ID:90 shown in FIG. 17A after 5 weeks of consumption of VFB (10-15 g/day). As shown in FIG. 17B, a dramatic decrease in glycemic volatility was observed in the subject ID:90 after treatment with VFB, with an average blood glucose level of approximately 100 mmol/dL maintained over the 24-hour period, similar to that observed in the normal subject (FIG. 15). The results shown in FIG. 17B are representative of the results measured over 5 consecutive 24-hour time periods in this subject after treatment with VFB.

FIG. 18A shows a CGMS graph for a third obese, non-diabetic subject (ID:20) measured over a 24-hour period prior to treatment with VFB (baseline). The results shown in FIG. 18A are representative of the results measured over 5 consecutive 24-hour time periods in this subject prior to treatment with VFB. As shown in FIG. 18A, the subject (ID:20) had increased glycemic volatility in comparison to the normal subject (FIG. 15), with frequent blood glucose excursions, resulting in an overall increased glycemic volatility as compared to a normal individual (see FIG. 15). FIG. 18B shows a CGMS graph for the same subject ID:20 shown in FIG. 18A after 5 weeks of consumption of VFB (10-15 g/day). As shown in FIG. 18B, a dramatic decrease in glycemic volatility was observed in the subject ID:20 after treatment with VFB, with an average blood glucose level of approximately 100 mmol/dL maintained over the 24-hour period, similar to that observed in the normal subject (FIG. 15). The results shown in FIG. 18B are representative of the results measured over 5 consecutive 24-hour time periods in this subject after treatment with VFB.

The results of the three subjects (ID:10, 20, 90) described above were representative of the other subjects included in this study (data not shown). These results demonstrate that VFB was effective to significantly reduce the glycemic volatility observed in obese subjects. In addition, it was noted that the obese, non-diabetic subjects in this study reported a significant decrease in subjective hunger and food cravings over the course of the five-week study.

Figure 19A:
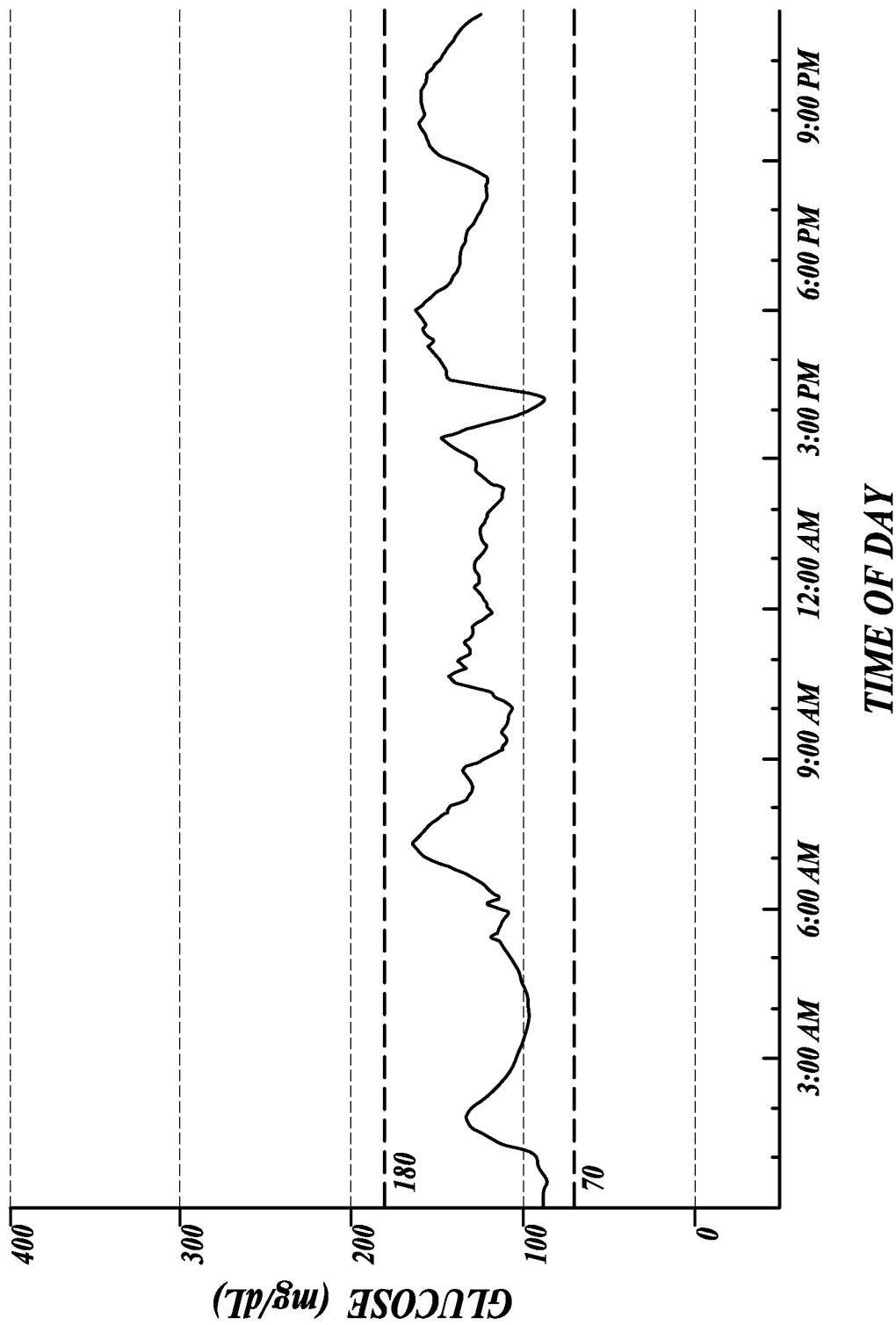
FIG. 19A shows a CGMS graph over a 24-hour period of an obese non-diabetic subject (ID:1098) prior to treatment with a low glycemic index diet (baseline)
Figure 19B:
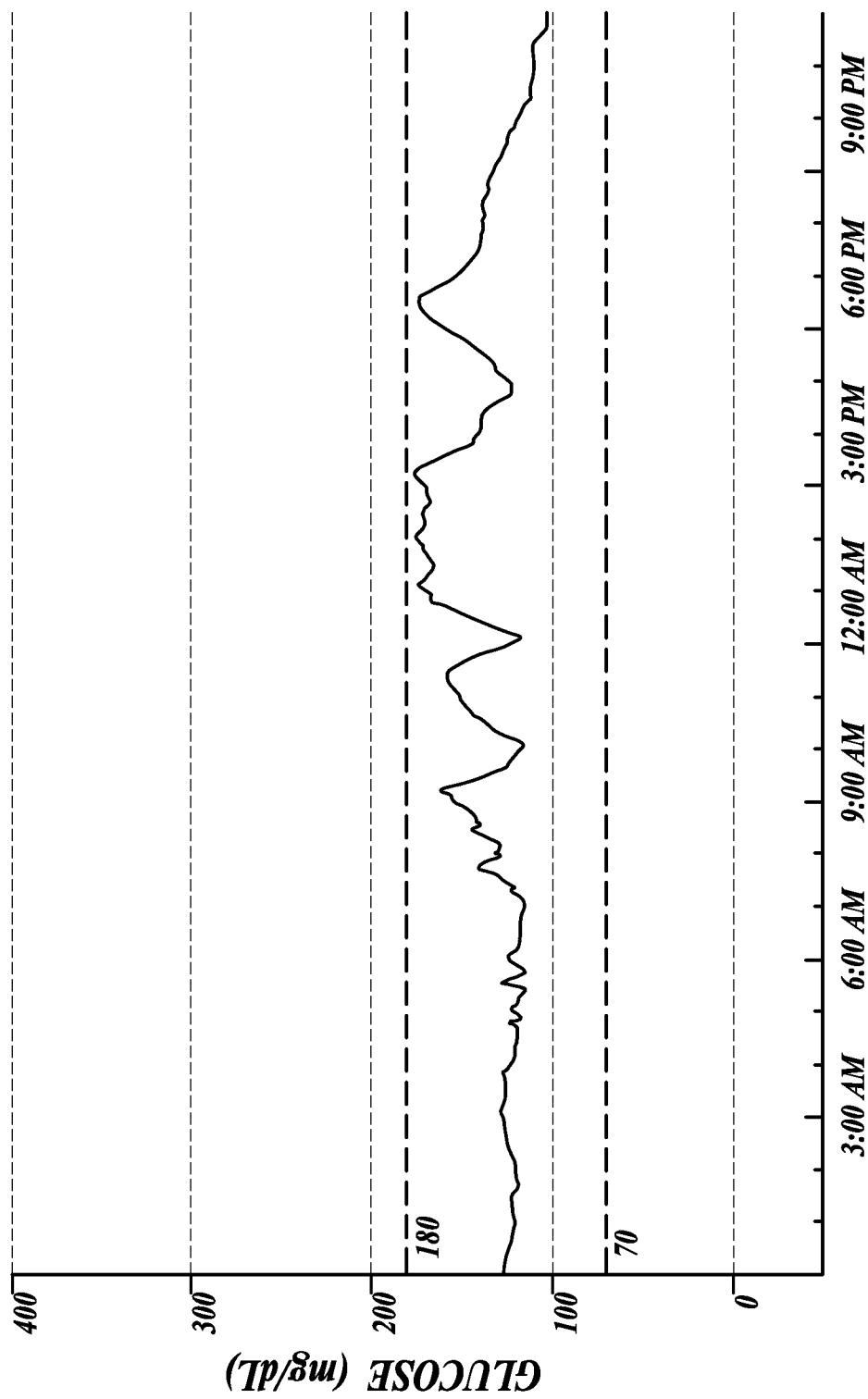
FIG. 19B shows a CGMS graph over a 24-hour period (from the same obese non-diabetic subject shown in FIG. 19A), after a six month low glycemic index diet.
Figure 19D:
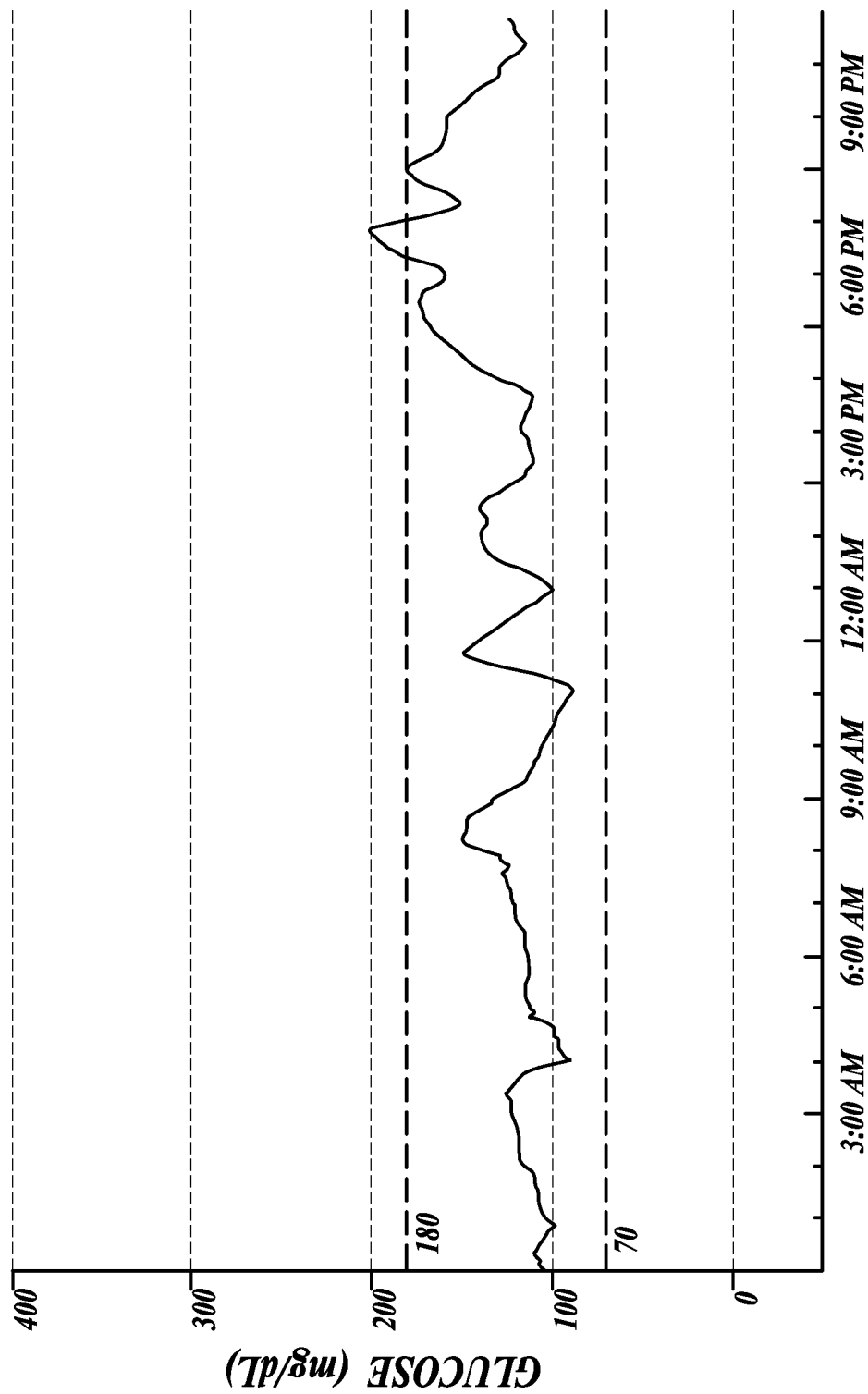
FIG. 19D shows a CGMS graph over a 24-hour period (from the same obese non-diabetic subject shown in FIG. 19C), after a six month low glycemic index diet.

Obese, Non-Diabetic Subjects (before and after Low Glycemic Index Diet):

CGMS data was obtained from several obese, non-diabetic subjects before and after treatment with a low glycemic index diet (without VFB). Importantly, in contrast to the results observed with VFB, it was observed that the low glycemic index diet did not significantly reduce glycemic volatility in these subjects. FIG. 19A shows a CGMS graph over a 24-hour period of an obese non-diabetic subject (ID: 1098) prior to treatment with a low glycemic index diet (baseline). FIG. 19B shows a CGMS graph over a 24-hour period (from the same obese non-diabetic subject shown in FIG. 19A), after a six-month low glycemic index diet. As shown, the glycemic volatility exhibited in the subject prior to the diet (FIG. 19A) was not significantly reduced by the low glycemic index diet (FIG. 19B). As another example, FIG. 19C shows a CGMS graph over a 24-hour period of a second obese, non-diabetic subject (ID: 1146) prior to treatment with a low glycemic index diet (baseline). FIG. 19D shows a CGMS graph over a 24-hour period (from the same obese non-diabetic subject shown in FIG. 19C), after a six-month low glycemic index diet. As shown, the glycemic volatility exhibited in the subject prior to the diet (FIG. 19C) was not significantly reduced by the low glycemic index diet (FIG. 19D). Therefore, these results demonstrate that a low glycemic index diet was not effective to reduce the glycemic volatility observed in obese subjects.

Diabetic Subjects (before and after VFB Treatment)

CGMS data was obtained from several diabetic subjects undergoing insulin treatment before and after treatment with VFB (10-15 g/day over a four-week period). FIG. 20A shows a CGMS graph over a 24-hour period from an obese diabetic subject on insulin (ID:60) prior to treatment with VFB (baseline). As shown in FIG. 20A, the blood sugar is poorly controlled in this subject, with peak blood glucose levels exceeding 300 mg/dL and low blood glucose levels below 70 mg/dL, along with frequent blood glucose excursions, resulting in an overall increased glycemic volatility as compared to a normal individual. The results shown in FIG. 20A are representative of the results measured over 5 consecutive 24-hour time periods in this subject prior to treatment with VFB.

Figure 20A:
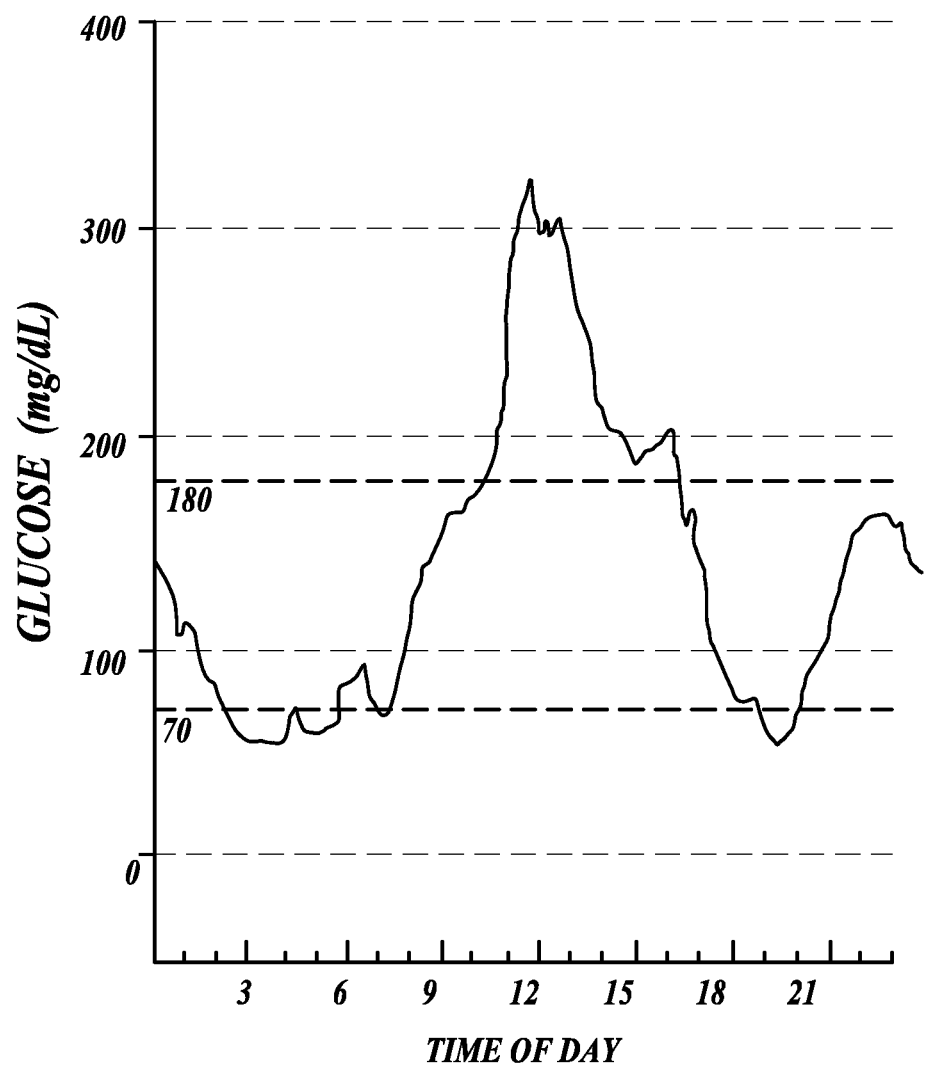
FIG. 20A shows a CGMS graph over a 24-hour period from an obese diabetic subject on insulin (ID:60) prior to treatment with VFB (baseline)
Figure 20B:
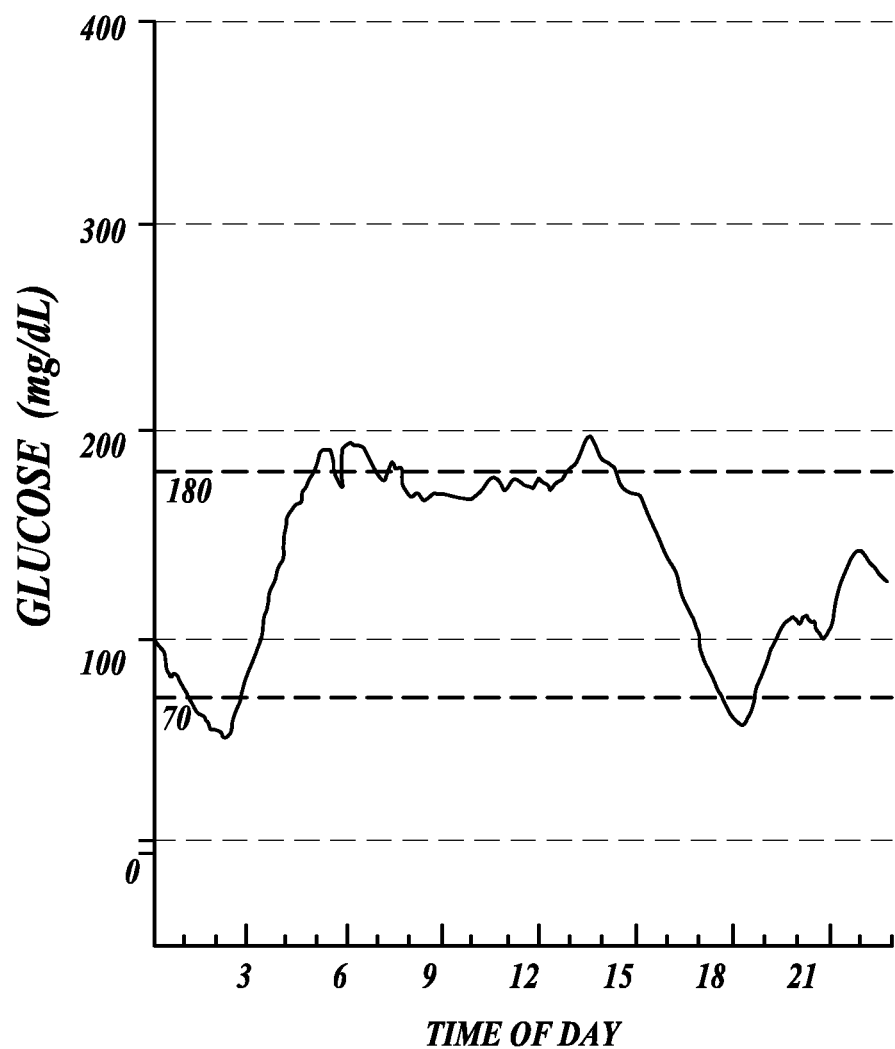
FIG. 20B shows a CGMS graph over a 24-hour period from the same diabetic subject as shown in FIG. 20A after treatment with VFB (10-15 g/day) for 4 weeks.

FIG. 20B shows a CGMS graph over a 24-hour period from the same diabetic subject as shown in FIG. 20A after treatment with VFB (10-15 g/day) for 4 weeks. As shown in FIG. 20B, the blood sugar levels are much better controlled with VFB treatment, and importantly, the insulin requirements were less than ½ the dose previously required before VFB treatment. The results shown in FIG. 20A are representative of the results measured over 5 consecutive 24-hour time periods in this subject after treatment with VFB. Similar effects have been observed in other diabetic subjects.

Conclusions:

In summary, these results demonstrate the significant and unexpected impact of VFB treatment on glycemic volatility and the superiority of VFB treatment to treatment with a low glycemic index diet alone in obese non-diabetic subjects. All the obese non-diabetic subjects analyzed in this study were observed to have increased glycemic volatility when measured over a 24-hour period prior to the initiation of the study (baseline) in comparison to normal control subjects which was markedly reduced after treatment with VFB. In addition, it was demonstrated that VFB treatment is effective to significantly improve blood sugar regulation in obese, insulin dependent diabetic subjects.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A food product comprising from 2.5 g to 7.5 g of a granulated dietary fiber composition per 50 g available carbohydrate of the food product, wherein the granulated dietary fiber composition comprises granules, wherein each granule comprises from about 60% to about 80% (w/w) glucomannan, from about 10% to about 20% (w/w) xanthan gum, and from about 5% to about 20% (w/w) alginate.

2. The food product of claim 1, wherein the food product is a solid food.

3. The food product of claim 2, wherein the food product comprises grain.

4. The food product of claim 3, wherein the food product is selected from the group consisting of rice, cereal, granola, oatmeal, baked goods, and pasta.

5. The food product of claim 2, wherein the food product comprises meat.

6. The food product of claim 1, wherein the food product is a dairy product selected from the group consisting of milk, yogurt, cheese, butter, and ice cream.

7. The food product of claim 1, wherein the food product is a liquid or semi-liquid selected from the group consisting of a meal replacement drink; a smoothie, a dietary supplement, a soup, and a juice.

8. The food product of claim 1, wherein the granulated dietary fiber composition comprises granules, wherein each granule comprises from about 70% to about 80% (w/w) glucomannan, from about 10% to about 20% (w/w) xanthan gum, and from about 10% to about 20% (w/w) alginate.

9. The food product of claim 1, wherein the granulated dietary fiber composition comprises granules, wherein each granule comprises about 70% (w/w) glucomannan, from about 13% to about 17% (w/w) xanthan gum, and from about 13% to about 17% (w/w) alginate.

10. The food product of claim 1, wherein the alginate is a medium viscosity alginate.

11. The food product of claim 1, wherein the food product is margarine.

12. The method of claim 5, wherein the meat is selected from the group consisting of poultry, beef, pork, and fish.

13. A method for reducing the glycemic index of a food product, the method comprising adding to the food product prior to consumption a granulated dietary fiber composition in an amount effective to reduce the glycemic index of the food product by at least 5 glycemic index units, wherein the granulated dietary fiber composition comprises granules, wherein each granule comprises from about 60% to about 80% (w/w) glucomannan, from about 10% to about 20% (w/w) xanthan gum, and from about 5% to about 20% (w/w) alginate.

14. The method of claim 13, wherein the granulated dietary fiber composition is baked into the food product.

15. The method of claim 13, wherein the granulated dietary fiber composition is mixed with the food product prior to consumption.

16. The method of claim 13, wherein the granulated dietary fiber composition is sprinkled onto the food product prior to consumption.

17. The method of claim 13, wherein the food product is a solid food product selected from the group consisting of rice, cereal, granola, baked goods, pasta and meat.

18. The method of claim 13, wherein the food product is a dairy product selected from the group consisting of milk, yogurt, cheese, butter, and ice cream.

19. The method of claim 13, wherein the amount of granulated dietary fiber composition added to the food product is in the range of 2.5 g to 7.5 g of fiber composition per 50 g available carbohydrate of the food product.

20. The method of claim 13, wherein the alginate is a medium viscosity alginate.

21. The method of claim 13, wherein the food product is margarine.

22. A method of reducing the glycemic volatility in a subject in need thereof, comprising administering to the subject in need thereof a granulated dietary fiber composition comprising granules, wherein each granule comprises from about 60% to about 80% (w/w) glucomannan, from about 10% to about 20% (w/w) xanthan gum, and from about 5% to about 20% (w/w) alginate.

23. The method of claim 22, wherein the granulated dietary fiber composition is administered to the subject in an amount from 5.0 g to 15.0 g per day.

24. The method of claim 22, wherein the granulated dietary fiber composition is administered to the subject for at least 4 weeks.

25. The method of claim 22, wherein the subject in need thereof is a human subject selected from the group consisting of an overweight subject, an obese non-diabetic subject and a type II diabetic subject.

26. The method of claim 22, wherein the granulated dietary fiber composition comprises granules, wherein each granule comprises from about 70% to about 80% (w/w) glucomannan, from about 10% to about 20% (w/w) xanthan gum, and from about 10% to about 20% (w/w) alginate.

27. The method of claim 22, wherein the granulated dietary fiber composition comprises granules, wherein each granule comprises about 70% (w/w) glucomannan, from about 13% to about 17% (w/w) xanthan gum, and from about 13% to about 17% (w/w) alginate.

28. The method of claim 22, wherein the granulated dietary fiber composition further comprises at least one lipid or blend thereof, wherein the lipid or blend thereof comprises at least 20% w/w of the total composition.

29. The method of claim 22, wherein the alginate is a medium viscosity alginate.

30. A method of reducing glycemic volatility in a subject comprising:
  (a) measuring a subject with a continuous glucose monitoring system for a designated time period to determine the baseline glycemic volatility of the subject; and
  (b) administering a effective dosage of a granulated dietary fiber composition to the subject, the granulated dietary fiber composition comprising granules, wherein each granule comprises from about 60% to about 80% (w/w) glucomannan, from about 10% to about 20% (w/w) xanthan gum, and from about 5% to about 20% (w/w) alginate for a time period effective to reduce the glycemic volatility of the subject as compared to the baseline glycemic volatility measured in step (a).

31. The method of claim 30, wherein the subject is measured with a continuous glucose monitoring system for at least 24-hours.

32. The method of claim 30, wherein the subject is treated with a dosage of granulated dietary fiber composition from 5.0 g to 15.0 g per day for at least 4 weeks.

33. The method of claim 30, wherein the subject is a non-diabetic overweight or obese subject having a baseline glycemic volatility with peak glucose levels exceeding 120 mmol/L and wherein treatment with the granulated dietary fiber composition reduces the glycemic volatility to a peak glucose level below 120 mmol/L.

34. The method of claim 30, wherein the subject is a diabetic obese subject having a baseline glycemic volatility with peak glucose levels exceeding 220 mmol/L and wherein treatment with the granulated dietary fiber composition reduces the glycemic volatility to a peak glucose level below 220 mmol/L.

35. The method of claim 30, wherein the alginate is a medium viscosity alginate.

* * * * *